US011596439B2

(12) United States Patent
Coe et al.

(10) Patent No.: US 11,596,439 B2
(45) Date of Patent: Mar. 7, 2023

(54) METHODS AND APPARATUS FOR PREVENTION OF SURGICAL SITE INFECTION

(71) Applicant: Prescient Surgical, Inc., San Carlos, CA (US)

(72) Inventors: Jonathan Coe, Menlo Park, CA (US); Jeremy Koehler, Menlo Park, CA (US); Nicholas Spinelli, San Carlos, CA (US); Edward Ruppel, III, Saratoga, CA (US); Kevin McDermott, San Francisco, CA (US)

(73) Assignee: Prescient Surgical, Inc., San Carlos, CA (US)

(*) Notice: Subject to any disclaimer, the term of this patent is extended or adjusted under 35 U.S.C. 154(b) by 163 days.

(21) Appl. No.: 16/868,623

(22) Filed: May 7, 2020

(65) Prior Publication Data

US 2021/0000501 A1 Jan. 7, 2021

Related U.S. Application Data

(63) Continuation of application No. PCT/US2018/059675, filed on Nov. 7, 2018.
(Continued)

(51) Int. Cl.
*A61B 17/34* (2006.01)
*A61B 17/02* (2006.01)

(52) U.S. Cl.
CPC ...... *A61B 17/3423* (2013.01); *A61B 17/0293* (2013.01); *A61B 2217/005* (2013.01); *A61B 2217/007* (2013.01)

(58) Field of Classification Search
CPC . A61B 17/3421; A61B 21/3423; A61B 17/02; A61B 17/0293
See application file for complete search history.

(56) References Cited

U.S. PATENT DOCUMENTS 1,157,202 A   10/1915 Uri et al.
1,255,182 A   2/1918  Krupski
(Continued)

FOREIGN PATENT DOCUMENTS

CA   2183064 A1   8/1995
CN   102935261 A  2/2013
(Continued)

OTHER PUBLICATIONS

Bennett-Guerrero, E., et al., Gentamicin-Collagen Sponge for Infection Prophylaxis in Colorectal Surgery, N. Engl. J. Med. 363(11):1038-1049, 2010.
(Continued)

*Primary Examiner* — Si Ming Ku
(74) *Attorney, Agent, or Firm* — Wilson Sonsini Goodrich & Rosati

(57) ABSTRACT

A surgical access device and methods for facilitating access through an incision or wound to a surgical site in a patient's body comprising an inferior retention member, a superior retention member, and a pliable membrane therebetween. The pliable membrane includes a base layer, a permeable membrane attached to the base layer, and a fluid delivery region disposed between the layers. The fluid delivery region is fluidly coupled to a fluid source. The fluid is delivered to the surgical site via the permeable membrane. The inferior retention member provides for fluid removal from the surgical site. Methods are provided for use of the surgical access device to retract tissue and deliver fluid to the tissue from the pliable membrane.

7 Claims, 30 Drawing Sheets

Related U.S. Application Data

(60) Provisional application No. 62/582,765, filed on Nov. 7, 2017.

(56) References Cited

U.S. PATENT DOCUMENTS

| | | |
|---|---|---|
| 1,810,466 A | 6/1931 | Deutsch |
| 1,862,725 A | 6/1932 | Robert et al. |
| 1,947,649 A | 2/1934 | Kadavy |
| 1,963,173 A | 6/1934 | Paul et al. |
| 2,083,573 A | 6/1937 | Morgan |
| 2,305,289 A | 12/1942 | Coburg |
| 2,313,164 A | 3/1943 | Nelson |
| 2,812,758 A | 11/1957 | Blumenschein |
| 3,038,467 A | 6/1962 | Sovatkin |
| 3,111,943 A | 11/1963 | Orndorff |
| 3,332,417 A | 7/1967 | Blanford et al. |
| 3,347,226 A | 10/1967 | Harrower |
| 3,347,227 A | 10/1967 | Harrower |
| 3,347,277 A | 10/1967 | Gwinn, Jr. |
| 3,397,692 A | 8/1968 | Creager, Jr. et al. |
| 3,402,710 A | 9/1968 | Paleschuck |
| 3,416,520 A | 12/1968 | Creager, Jr. |
| 3,496,687 A | 2/1970 | Greenberg et al. |
| 3,672,104 A | 6/1972 | Luckey |
| 3,782,370 A | 1/1974 | McDonald |
| 3,789,852 A | 2/1974 | Kim et al. |
| 3,807,393 A | 4/1974 | Mc Donald |
| 3,939,727 A | 2/1976 | Asquith |
| 4,024,872 A | 5/1977 | Muldoon |
| 4,034,746 A | 7/1977 | Williams |
| 4,043,332 A | 8/1977 | Metcalf |
| 4,130,113 A | 12/1978 | Graham |
| 4,188,945 A | 2/1980 | Wenander |
| 4,239,036 A | 12/1980 | Krieger |
| 4,254,763 A | 3/1981 | McCready et al. |
| 4,537,680 A | 8/1985 | Barth |
| 4,553,537 A | 11/1985 | Rosenberg |
| 4,777,943 A | 10/1988 | Chvapil |
| 4,889,107 A | 12/1989 | Kaufman |
| 4,942,700 A | 7/1990 | Hoberman |
| 4,984,564 A | 1/1991 | Yuen |
| 5,024,031 A | 6/1991 | Hoberman |
| 5,038,532 A | 8/1991 | Shahinpoor |
| 5,105,983 A | 4/1992 | Sancoff et al. |
| 5,146,916 A | 9/1992 | Catalani |
| 5,159,921 A | 11/1992 | Hoover |
| 5,263,922 A | 11/1993 | Sova et al. |
| 5,284,481 A | 2/1994 | Soika et al. |
| 5,352,201 A | 10/1994 | Jemmott |
| 5,358,494 A | 10/1994 | Svedman |
| 5,364,356 A | 11/1994 | Hoefling |
| 5,366,478 A | 11/1994 | Brinkerhoff et al. |
| 5,437,683 A | 8/1995 | Neumann et al. |
| 5,466,231 A | 11/1995 | Cercone et al. |
| 5,486,183 A | 1/1996 | Middleman et al. |
| 5,520,610 A | 5/1996 | Giglio et al. |
| 5,522,791 A | 6/1996 | Leyva |
| 5,524,464 A | 6/1996 | Asada et al. |
| 5,524,644 A | 6/1996 | Crook |
| 5,562,690 A | 10/1996 | Green et al. |
| 5,616,121 A | 4/1997 | McKay |
| 5,632,284 A | 5/1997 | Graether |
| 5,643,178 A | 7/1997 | Moll et al. |
| 5,649,550 A | 7/1997 | Crook |
| 5,697,946 A | 12/1997 | Hopper et al. |
| 5,738,629 A | 4/1998 | Moll et al. |
| 5,741,298 A | 4/1998 | Macleod |
| 5,755,661 A | 5/1998 | Schwartzman |
| 5,761,871 A | 6/1998 | Atake |
| 5,779,629 A | 7/1998 | Hohlen |
| 5,800,420 A | 9/1998 | Gross et al. |
| 5,803,921 A | 9/1998 | Bonadio |
| 5,810,721 A | 9/1998 | Mueller et al. |
| 5,832,925 A | 11/1998 | Rothrum |
| 5,842,971 A | 12/1998 | Yoon |
| 5,853,395 A | 12/1998 | Crook et al. |
| 5,865,728 A | 2/1999 | Moll et al. |
| 5,871,474 A | 2/1999 | Hermann et al. |
| 5,899,208 A | 5/1999 | Bonadio |
| 5,902,266 A | 5/1999 | Leone et al. |
| 5,906,577 A | 5/1999 | Beane et al. |
| 5,947,922 A | 9/1999 | Macleod |
| 5,951,588 A | 9/1999 | Moenning |
| 5,964,781 A | 10/1999 | Mollenauer et al. |
| 5,984,943 A | 11/1999 | Young |
| 6,010,494 A | 1/2000 | Schaefer et al. |
| 6,033,426 A | 3/2000 | Kaji |
| 6,033,428 A | 3/2000 | Sardella |
| 6,045,535 A | 4/2000 | Ben Nun |
| 6,048,309 A | 4/2000 | Flom et al. |
| 6,077,288 A | 6/2000 | Shimomura et al. |
| 6,086,603 A | 7/2000 | Termin et al. |
| 6,090,043 A | 7/2000 | Austin et al. |
| 6,142,935 A | 11/2000 | Flom et al. |
| 6,142,936 A | 11/2000 | Beane et al. |
| 6,149,642 A | 11/2000 | Gerhart et al. |
| 6,150,608 A | 11/2000 | Wambeke et al. |
| 6,162,172 A | 12/2000 | Cosgrove et al. |
| 6,219,974 B1 | 4/2001 | Hoberman |
| 6,254,533 B1 | 7/2001 | Fadem et al. |
| 6,254,534 B1 | 7/2001 | Butler et al. |
| 6,331,850 B1 | 12/2001 | Olodort et al. |
| 6,354,995 B1 | 3/2002 | Hoftman et al. |
| 6,371,968 B1 | 4/2002 | Kogasaka et al. |
| 6,382,211 B1 | 5/2002 | Crook |
| 6,383,162 B1 | 5/2002 | Sugarbaker |
| 6,440,063 B1 | 8/2002 | Beane et al. |
| 6,442,413 B1 | 8/2002 | Silver |
| 6,450,983 B1 | 9/2002 | Rambo |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,613,952 B2 | 9/2003 | Rambo |
| 6,623,426 B2 | 9/2003 | Bonadio et al. |
| 6,695,824 B2 | 2/2004 | Howard et al. |
| 6,723,044 B2 | 4/2004 | Pulford et al. |
| 6,730,020 B2 | 5/2004 | Peng et al. |
| 6,739,098 B2 | 5/2004 | Hoberman |
| 6,814,078 B2 | 11/2004 | Crook |
| 6,814,700 B1 | 11/2004 | Mueller et al. |
| 6,846,287 B2 | 1/2005 | Bonadio et al. |
| 6,899,889 B1 | 5/2005 | Hnojewyj et al. |
| 6,908,430 B2 | 6/2005 | Caldwell et al. |
| 6,918,312 B2 | 7/2005 | Elwood et al. |
| 6,939,296 B2 | 9/2005 | Ewers et al. |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 7,008,377 B2 | 3/2006 | Beane et al. |
| 7,033,319 B2 | 4/2006 | Pulford et al. |
| 7,052,454 B2 | 5/2006 | Taylor |
| 7,081,089 B2 | 7/2006 | Bonadio et al. |
| 7,100,333 B2 | 9/2006 | Hoberman |
| 7,163,510 B2 | 1/2007 | Kahle et al. |
| 7,195,590 B2 | 3/2007 | Butler et al. |
| 7,214,185 B1 | 5/2007 | Rosney et al. |
| 7,235,062 B2 | 6/2007 | Brustad |
| 7,238,154 B2 | 7/2007 | Ewers et al. |
| 7,247,314 B2 | 7/2007 | Hnojewyj et al. |
| 7,279,208 B1 | 10/2007 | Goffena et al. |
| 7,297,106 B2 | 11/2007 | Yamada et al. |
| 7,300,399 B2 | 11/2007 | Bonadio et al. |
| 7,377,898 B2 | 5/2008 | Ewers et al. |
| 7,393,322 B2 | 7/2008 | Wenchell |
| 7,445,597 B2 | 11/2008 | Butler et al. |
| 7,473,221 B2 | 1/2009 | Ewers et al. |
| 7,481,765 B2 | 1/2009 | Ewers et al. |
| 7,537,564 B2 | 5/2009 | Bonadio et al. |
| 7,540,215 B2 | 6/2009 | Hoberman et al. |
| 7,540,839 B2 | 6/2009 | Butler et al. |
| 7,559,893 B2 | 7/2009 | Bonadio et al. |
| 7,644,721 B2 | 1/2010 | Hoberman et al. |
| 7,650,887 B2 | 1/2010 | Nguyen et al. |
| 7,666,718 B2 | 2/2010 | Suzawa et al. |

(56) References Cited

U.S. PATENT DOCUMENTS

| | | |
|---|---|---|
| 7,704,207 B2 | 4/2010 | Albrecht et al. |
| 7,717,847 B2 | 5/2010 | Smith |
| 7,727,146 B2 | 6/2010 | Albrecht et al. |
| 7,736,306 B2 | 6/2010 | Brustad et al. |
| 7,758,500 B2 | 7/2010 | Boyd et al. |
| 7,815,567 B2 | 10/2010 | Albrecht et al. |
| 7,833,156 B2 | 11/2010 | Williams et al. |
| 7,867,164 B2 | 1/2011 | Butler et al. |
| 7,878,974 B2 | 2/2011 | Brustad et al. |
| 7,883,461 B2 | 2/2011 | Albrecht et al. |
| 7,892,172 B2 | 2/2011 | Albrecht et al. |
| 7,909,760 B2 | 3/2011 | Albrecht et al. |
| 7,909,761 B2 | 3/2011 | Banchieri et al. |
| 7,913,697 B2 | 3/2011 | Nguyen et al. |
| 7,928,281 B2 | 4/2011 | Augustine et al. |
| 7,951,076 B2 | 5/2011 | Hart et al. |
| 7,967,748 B2 | 6/2011 | Kistler et al. |
| 7,998,068 B2 | 8/2011 | Bonadio et al. |
| 8,012,088 B2 | 9/2011 | Butler et al. |
| 8,016,755 B2 | 9/2011 | Ewers et al. |
| 8,021,296 B2 | 9/2011 | Bonadio et al. |
| 8,033,995 B2 | 10/2011 | Cropper et al. |
| 8,034,367 B2 | 10/2011 | Hnojewyj |
| 8,070,676 B2 | 12/2011 | Ewers et al. |
| 8,075,482 B2 | 12/2011 | Beckman et al. |
| 8,105,234 B2 | 1/2012 | Ewers et al. |
| 8,109,873 B2 | 2/2012 | Albrecht et al. |
| 8,142,354 B1 | 3/2012 | Larson et al. |
| 8,182,647 B2 | 5/2012 | Smith et al. |
| 8,226,552 B2 | 7/2012 | Albrecht et al. |
| 8,227,657 B2 | 7/2012 | Aali |
| 8,241,260 B2 | 8/2012 | Livne et al. |
| 8,282,545 B1 | 10/2012 | Bodenstein |
| 8,291,781 B2 | 10/2012 | Guerrero et al. |
| 8,357,188 B2 | 1/2013 | Boynton et al. |
| 8,383,144 B2 | 2/2013 | Hnojewyj |
| 8,409,605 B2 | 4/2013 | Hnojewyj et al. |
| 8,454,502 B2 | 6/2013 | Kleyman |
| 8,518,024 B2 | 8/2013 | Williams et al. |
| 8,574,155 B2 | 11/2013 | O'Prey et al. |
| 8,733,453 B2 | 5/2014 | Guerrero et al. |
| 8,758,236 B2 | 6/2014 | Albrecht et al. |
| 8,814,788 B2 | 8/2014 | Gan |
| 8,857,440 B2 | 10/2014 | Gundlapalli et al. |
| 9,017,253 B2 | 4/2015 | Guralnik et al. |
| 9,041,538 B2 | 5/2015 | Peeters |
| 9,084,594 B2 | 7/2015 | Suh et al. |
| 9,220,837 B2 | 12/2015 | Pesach et al. |
| 9,393,005 B2 | 7/2016 | Suh et al. |
| 9,402,612 B2 | 8/2016 | Koehler et al. |
| 9,402,973 B2 | 8/2016 | Phillips et al. |
| 9,610,096 B2 | 7/2017 | Koehler et al. |
| 9,788,823 B2 | 10/2017 | Suh et al. |
| 9,974,564 B2 | 5/2018 | Koehler et al. |
| 10,085,734 B2 | 10/2018 | Suh et al. |
| 10,085,735 B2 | 10/2018 | Ferragamo et al. |
| 10,327,751 B2 | 6/2019 | Coe et al. |
| 10,637,099 B2 | 4/2020 | Zhang et al. |
| 10,993,709 B2 | 5/2021 | Suh et al. |
| 2002/0002324 A1 | 1/2002 | McManus |
| 2002/0013542 A1 | 1/2002 | Bonadio et al. |
| 2003/0168068 A1 | 9/2003 | Poole et al. |
| 2003/0187376 A1 | 10/2003 | Rambo |
| 2003/0192553 A1 | 10/2003 | Rambo |
| 2004/0030304 A1 | 2/2004 | Hunt et al. |
| 2004/0054353 A1 | 3/2004 | Taylor |
| 2004/0154624 A1 | 8/2004 | Bonadio et al. |
| 2004/0225193 A1 | 11/2004 | Krebs |
| 2004/0267096 A1 | 12/2004 | Caldwell et al. |
| 2005/0020884 A1 | 1/2005 | Hart et al. |
| 2005/0119613 A1 | 6/2005 | Moenning et al. |
| 2005/0148823 A1 | 7/2005 | Vaugh et al. |
| 2005/0155611 A1 | 7/2005 | Vaugh et al. |
| 2005/0209510 A1 | 9/2005 | Bonadio et al. |
| 2005/0215863 A1 | 9/2005 | Ravikumar et al. |
| 2005/0222582 A1 | 10/2005 | Wenchell |
| 2005/0261720 A1 | 11/2005 | Caldwell et al. |
| 2005/0273131 A1 | 12/2005 | Shluzas et al. |
| 2005/0283050 A1 | 12/2005 | Gundlapalli et al. |
| 2006/0004261 A1 | 1/2006 | Douglas et al. |
| 2006/0025749 A1 | 2/2006 | Moenning |
| 2006/0074278 A1 | 4/2006 | Petit et al. |
| 2006/0095020 A1 | 5/2006 | Casas et al. |
| 2006/0149137 A1 | 7/2006 | Pingleton et al. |
| 2006/0149306 A1 | 7/2006 | Hart et al. |
| 2006/0161050 A1 | 7/2006 | Butler et al. |
| 2006/0217596 A1 | 9/2006 | Williams |
| 2006/0247500 A1 | 11/2006 | Voegele et al. |
| 2006/0270911 A1 | 11/2006 | Voegele et al. |
| 2007/0010716 A1 | 1/2007 | Malandain et al. |
| 2007/0060884 A1 | 3/2007 | Hayek |
| 2007/0062948 A1 | 3/2007 | Albrecht et al. |
| 2007/0073110 A1 | 3/2007 | Larson et al. |
| 2007/0259147 A1 | 11/2007 | Boudry et al. |
| 2007/0261548 A1 | 11/2007 | Vrzalik et al. |
| 2008/0081951 A1 | 4/2008 | Frasier et al. |
| 2008/0208222 A1 | 8/2008 | Beckman et al. |
| 2008/0255519 A1 | 10/2008 | Piskun et al. |
| 2008/0275408 A1 | 11/2008 | Boynton et al. |
| 2008/0281162 A1 | 11/2008 | Albrecht et al. |
| 2008/0281297 A1 | 11/2008 | Pesach et al. |
| 2008/0294127 A1 | 11/2008 | Blott et al. |
| 2008/0319268 A1 | 12/2008 | Michaeli et al. |
| 2009/0054803 A1 | 2/2009 | Saadat et al. |
| 2009/0093752 A1 | 4/2009 | Richard et al. |
| 2009/0118587 A1 | 5/2009 | Voegele et al. |
| 2009/0137984 A1 | 5/2009 | Minnelli |
| 2009/0158674 A1 | 6/2009 | Guerrero et al. |
| 2009/0192360 A1 | 7/2009 | Riess et al. |
| 2009/0287060 A1 | 11/2009 | Pell et al. |
| 2010/0063375 A1 | 3/2010 | Kassab et al. |
| 2010/0081880 A1 | 4/2010 | Widenhouse et al. |
| 2010/0094227 A1 | 4/2010 | Albrecht et al. |
| 2010/0100043 A1 | 4/2010 | Racenet |
| 2010/0130958 A1 | 5/2010 | Kang et al. |
| 2010/0145152 A1* | 6/2010 | Smith ............... A61B 17/0218 600/201 |
| 2010/0198329 A1 | 8/2010 | Kassab et al. |
| 2010/0234794 A1 | 9/2010 | Weadock et al. |
| 2010/0249516 A1 | 9/2010 | Shelton, IV et al. |
| 2010/0261972 A1 | 10/2010 | Widenhouse et al. |
| 2010/0261974 A1 | 10/2010 | Shelton, IV et al. |
| 2010/0280326 A1 | 11/2010 | Hess et al. |
| 2010/0312064 A1 | 12/2010 | Weisenburgh, II et al. |
| 2010/0312066 A1 | 12/2010 | Cropper et al. |
| 2010/0312253 A1 | 12/2010 | Nevyas-Wallace et al. |
| 2010/0324375 A1 | 12/2010 | Piskun |
| 2011/0021879 A1 | 1/2011 | Hart et al. |
| 2011/0034888 A1 | 2/2011 | Aali |
| 2011/0054260 A1 | 3/2011 | Albrecht et al. |
| 2011/0118551 A1 | 5/2011 | Ciporen et al. |
| 2011/0124973 A1 | 5/2011 | Ross |
| 2011/0137267 A1 | 6/2011 | Phillips et al. |
| 2011/0282160 A1 | 11/2011 | Bhadri et al. |
| 2011/0313383 A1 | 12/2011 | Hofstetter et al. |
| 2011/0319719 A1 | 12/2011 | O'Prey et al. |
| 2012/0022334 A1 | 1/2012 | Piskun |
| 2012/0041269 A1 | 2/2012 | Copeland et al. |
| 2012/0203069 A1 | 8/2012 | Hannaford et al. |
| 2012/0209078 A1 | 8/2012 | Pribanic et al. |
| 2012/0245423 A1 | 9/2012 | Rodrigues |
| 2012/0245425 A1 | 9/2012 | Okoniewski |
| 2012/0289785 A1 | 11/2012 | Albrecht et al. |
| 2012/0296170 A1 | 11/2012 | Wilkins et al. |
| 2012/0322783 A1 | 12/2012 | Klein |
| 2013/0030252 A1 | 1/2013 | Kaul |
| 2013/0150681 A1 | 6/2013 | O'Prey et al. |
| 2013/0178709 A1* | 7/2013 | Suh .................. A61B 17/0293 600/205 |
| 2013/0178710 A1 | 7/2013 | Suh et al. |
| 2013/0184535 A1 | 7/2013 | Suh et al. |
| 2013/0194375 A1 | 8/2013 | Michrowski et al. |
| 2014/0017335 A1 | 1/2014 | Dimov et al. |
| 2014/0046123 A1 | 2/2014 | Connors et al. |

(56) References Cited

U.S. PATENT DOCUMENTS

| | | |
|---|---|---|
| 2014/0066704 A1 | 3/2014 | Blumenkranz et al. |
| 2014/0114138 A1 | 4/2014 | Fedorov et al. |
| 2014/0316210 A1 | 10/2014 | Koehler et al. |
| 2014/0343366 A1 | 11/2014 | Coe et al. |
| 2015/0142049 A1 | 5/2015 | Delgado et al. |
| 2015/0238073 A1 | 8/2015 | Charles et al. |
| 2015/0272565 A1 | 10/2015 | Suh et al. |
| 2015/0335322 A1 | 11/2015 | Galbierz et al. |
| 2016/0242751 A1 | 8/2016 | Bonadio et al. |
| 2016/0338730 A1 | 11/2016 | Koehler et al. |
| 2017/0128059 A1 | 5/2017 | Coe et al. |
| 2019/0090902 A1 | 3/2019 | Koehler et al. |
| 2019/0231335 A1 | 8/2019 | Suh et al. |

FOREIGN PATENT DOCUMENTS

| | | |
|---|---|---|
| DE | 736480 C | 6/1943 |
| DE | 20112861 U1 | 12/2002 |
| EP | 1609429 A2 | 12/2005 |
| JP | 2005506144 A | 3/2005 |
| JP | 2006142037 A | 6/2006 |
| WO | WO-9102466 A1 | 3/1991 |
| WO | WO-03034908 A2 | 5/2003 |
| WO | WO-2010097477 A2 | 9/2010 |
| WO | WO-2010107454 A1 | 9/2010 |
| WO | WO-2011026124 A1 | 3/2011 |
| WO | WO-2013106347 A1 | 7/2013 |
| WO | WO-2014151954 A2 | 9/2014 |
| WO | WO-2014153473 A2 | 9/2014 |
| WO | WO-2019094502 A1 | 5/2019 |

OTHER PUBLICATIONS

"Beth Israel Lahey Health Winchester Hospital, Colectomy-Open Surgery" website https://www.winchesterhospital.org/health-library/article?id=100936#, access Sep. 29, 2019, PDF (Year: 2019).
Cheadle, W.G., Risk Factors for Surgical Site Infection, Surgical Infections 7(s1):s7-s11, 2006.
Co-pending U.S. Appl. No. 16/406,569, filed May 8, 2019.
European search report and opinion dated Jun. 29, 2015 for EP Application No. 13736414.7.
European search report and opinion dated Jul. 25, 2016 for EP Application No. 14769323.8.
European Search Report and Search Opinion dated Sep. 15, 2017 for European Patent Application No. 16193928.5.
Hopkins ABX Guide, Cefazolin Antibiotic, Website accessed Dec. 10, 2018, "C:\Users\tmatthews1\Documents\e-Red Folder\15344407\Cefazolin Antibiotic.html:"; copyright 2005-2017.
International search report and written opinion dated Sep. 5, 2014 for PCT/US2014/031366.
International search report and written opinion dated Oct. 3, 2014 for PCT/US2014/026723.
Japanese Office Action dated Nov. 29, 2016 for Japanese Application No. 2014-552254(STFRD1.002JP1) in 3 pages.
Lord, J., et al., Intraoperative Antibiotic Wound Lavage: An Attempt to Eliminate Postoperative Infection in Arterial and Clean General Surgical Procedures, Ann. Surg. 185(6):634, 1977.
Notice of allowance dated May 26, 2016 for U.S. Appl. No. 14/209,393.
Notice of Allowance dated May 29, 2018 for U.S. Appl. No. 15/186,141.
Notice of Allowance dated Jun. 8, 2016 for U.S. Appl. No. 13/736,888.
Notice of Allowance dated Jun. 20, 2017 for U.S. Appl. No. 14/739,484.
Notice of Allowance dated Dec. 6, 2016 for U.S. Appl. No. 15/194,787.
Office action dated Jan. 26, 2016 for U.S. Appl. No. 14/209,393.
Office action dated Mar. 10, 2016 for U.S. Appl. No. 13/736,888.
Office Action dated Mar. 7, 2016 for U.S. Appl. No. 13/736,904.
Office Action dated May 17, 2016 for U.S. Appl. No. 14/220,928.
Office Action dated May 20, 2015 for U.S. Appl. No. 13/736,904.
Office action dated Jul. 20, 2015 for U.S. Appl. No. 13/736,888.
Office Action dated Jul. 26, 2016 for U.S. Appl. No. 13/736,904.
Office Action dated Aug. 24, 2016 for U.S. Appl. No. 14/739,484.
Office Action dated Sep. 15, 2017 for U.S. Appl. No. 14/220,928.
Office action dated Sep. 27, 2016 for U.S. Appl. No. 15/194,787.
Office action dated Oct. 17, 2014 for U.S. Appl. No. 13/736,875.
Office action dated Nov. 20, 2014 for U.S. Appl. No. 13/736,904.
Office Action dated Dec. 28, 2016 for U.S. Appl. No. 14/220,928.
PCT/US18/59675 Search Report & Written Opinion dated Jan. 7, 2019.
PCT/US2013/020701 Search Report & Written Opinion dated Mar. 12, 2013.
U.S. Appl. No. 14/220,928 Notice of Allowance dated Feb. 8, 2019.
U.S. Appl. No. 13/736,875 Notice of Allowance dated Jun. 1, 2015.
U.S. Appl. No. 14/220,928 Office Action dated Jul. 13, 2018.
U.S. Appl. No. 15/186,141 Office Action dated Apr. 7, 2017.
U.S. Appl. No. 15/344,407 Office Action dated Dec. 17, 2018.
U.S. Appl. No. 15/344,407 Office Action dated Oct. 3, 2019.
U.S. Appl. No. 15/442,090 Notice of Allowance dated Jan. 19, 2018.
U.S. Appl. No. 16/121,484 Office Action dated May 28, 2020.
U.S. Appl. No. 15/957,381 Office Action dated Oct. 3, 2019.
U.S. Appl. No. 16/121,484 Notice of Allowance dated Jan. 29, 2021.
U.S. Appl. No. 16/121,484 Office Action dated Dec. 8, 2020.

* cited by examiner

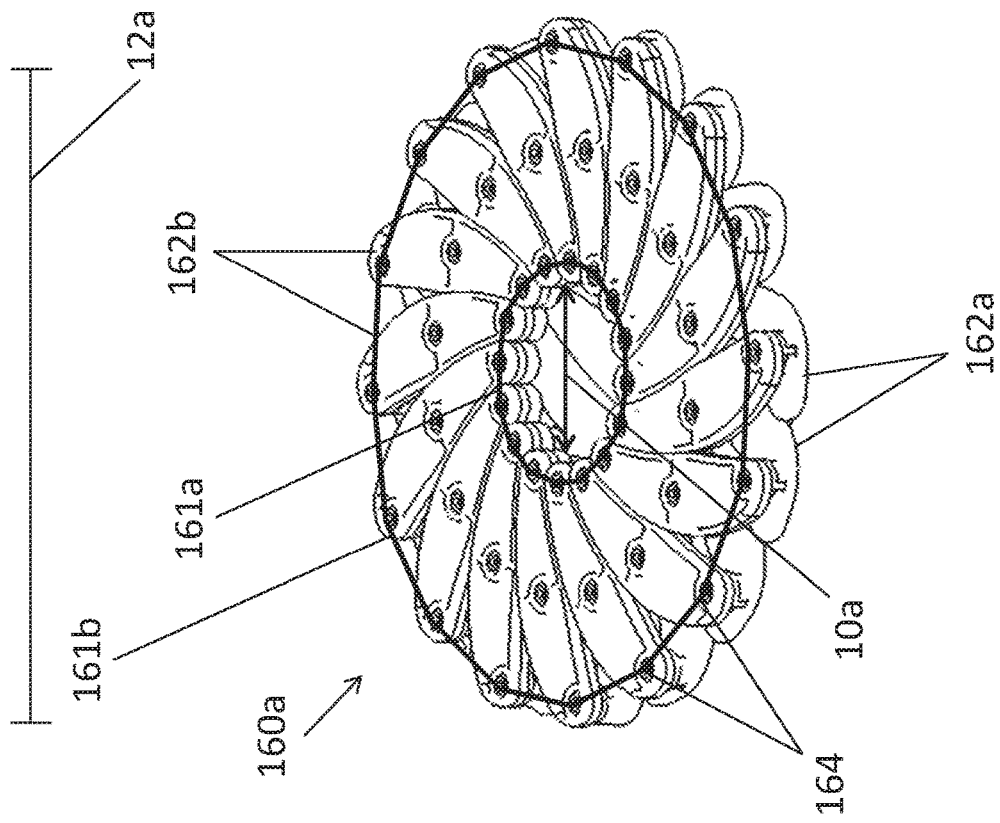
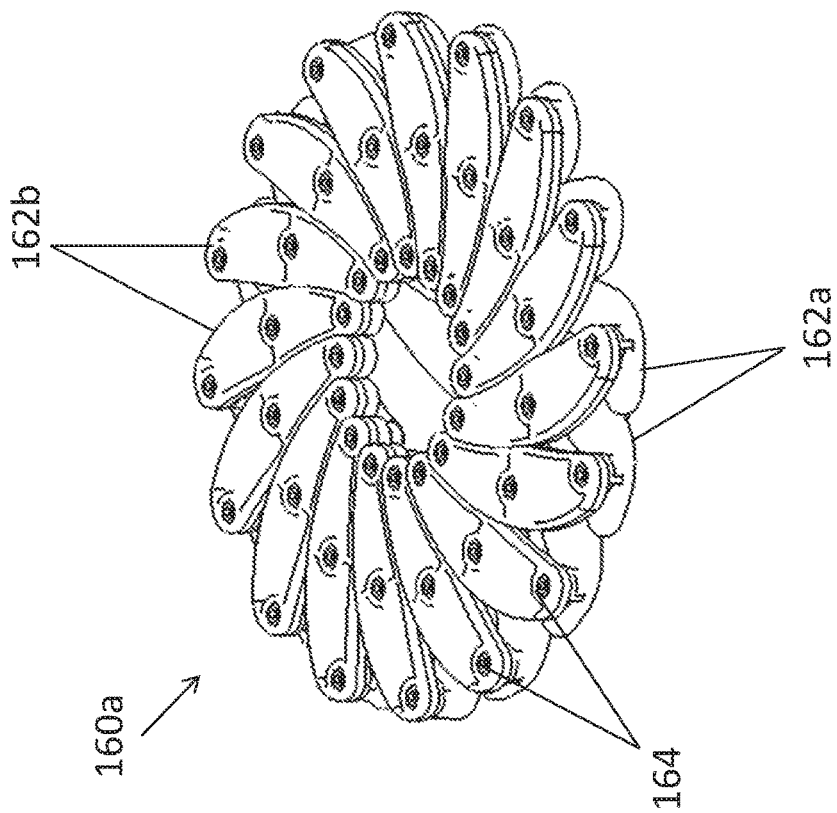
FIG. 17B
FIG. 17A

METHODS AND APPARATUS FOR PREVENTION OF SURGICAL SITE INFECTION

CROSS-REFERENCE

This application is a continuation of International Patent Application No. PCT/US2018/059675, filed on Nov. 7, 2018, entitled "Methods and Apparatus for Prevention of Surgical Site Infection", which claims the benefit of U.S. Provisional Application No. 62/582,765, filed on Nov. 7, 2017, entitled "Methods and Apparatus for Prevention of Surgical Site Infection", the entire contents of which are incorporated herein by reference.

This application is related to U.S. patent application Ser. No. 13/736,904, filed on Jan. 8, 2013, entitled "Expandable Tissue Retraction Devices"; U.S. Pat. No. 9,393,005, issued Jul. 19, 2016, entitled "Systems for the Prevention of Surgical Site Infections"; U.S. Pat. No. 9,084,594, issued Jul. 21, 2015, entitled "Methods for the Prevention of Surgical Site Infections"; U.S. Pat. No. 9,402,612, issued Aug. 2, 2016, entitled "Methods and Devices for the Prevention of Incisional Surgical Site Infections"; U.S. patent application Ser. No. 14/220,928, filed Mar. 20, 2014, entitled "Methods and Apparatus for Reducing the Risk of Surgical Site Infections"; U.S. Patent Application No. 62/488,105, filed Apr. 21, 2017, entitled "Methods and Apparatus for the Prevention of Surgical Site Infection"; U.S. Patent Application No. 62/501,877, filed May 5, 2017, entitled "Methods and Devices for Preventing Infections During Vascular Access"; U.S. Pat. No. 9,788,823, issued Oct. 17, 2017, entitled "Methods for the Prevention of Surgical Site Infections"; U.S. Pat. No. 10,085,735, issued Oct. 2, 2018, entitled "Systems for the Prevention of Surgical Site Infections"; U.S. patent application Ser. No. 16/121,484, filed Sep. 4, 2018, entitled "Systems for the Prevention of Surgical Site Infections"; U.S. Pat. No. 9,610,096, issued Apr. 4, 0217, entitled "Methods and Devices for the Prevention of Incisional Surgical Site Infections"; U.S. Pat. No. 9,974,563, issued May 22, 2018, entitled "Methods and Devices for the Prevention of Incisional Surgical Site Infections"; U.S. patent application Ser. No. 15/957,381, filed Apr. 19, 2018, entitled "Methods and Devices for the Prevention of Incisional Surgical Site Infections"; and U.S. patent application Ser. No. 15/344,407, filed Nov. 4, 2016, entitled "Methods and Apparatus for Prevention of Surgical Site Infections", the entire disclosures of which are incorporated herein by reference.

BACKGROUND OF THE INVENTION

Formerly known as "wound infection," surgical site infection (SSI) is generally defined by the Centers for Disease Control and Prevention (CDC) as an infection in the area of the surgical incision that occurs within 30 days of an operation. The CDC further subdivides SSI into two groups. The first group includes superficial and deep "incisional" SSI (ISSI). The second group includes "organ/space" SSI. These two groups appear to be somewhat different phenomena with respect to etiology, physiology, pathogenesis, clinical presentation, and treatment. Of note, the term "wound infection," as currently used in the medical colloquium, refers to and is more compatible with ISSI, as opposed to organ/space SSI.

ISSI affects approximately 3-4% of the more than 30 million operations performed in the U.S. each year. Although the state of current medical care has minimized the mortality associated with ISSI, the morbidity and associated costs to the healthcare system remain significant. On average, ISSI extends the length of an inpatient hospital stay by 9 days, as well as introduces the added necessity and costs of outpatient wound management, which can reach upwards of 10,000-45,000 U.S. dollars per patient. Estimates of the aggregate annual burden to the U.S. healthcare system exceed five billion U.S. dollars.

The diagnosis of SSI is usually made by a physician and is usually based on the clinical finding of various signs and symptoms of infection at the incisional site, such as pain, tenderness, swelling, redness, warmth, and purulent drainage. Various ancillary tests, such as microbial cultures or radiographic exams (e.g., computed tomography scans), can aid in the diagnosis. The length of treatment can extend for weeks or even months.

Obese patients are particularly vulnerable to developing wound infections, with a two to three fold increased risk relative to the overall population. This is at least partially due to the poor vascularization of subcutaneous fat, reducing the delivery of prophylactic intravenous (IV) antibiotics to the incision site. Furthermore, subcutaneous fat is an excellent media for the incubation of bacterial infection. With increasing rates of obesity worldwide, this will only further compound the problem of ISSI.

Another risk factor for the development of ISSI is the type of surgical procedure performed. For example, colorectal surgeries are associated with a baseline infection rate of 15-20%. This is a result of the contaminated nature of the procedure, as fecal contents are often released into the operative field when colon, small bowel, or rectum is cut. Furthermore, colorectal surgery involves the manipulation and removal of large organs (e.g. the colon), and consequently, large incisions are often required to perform the procedures. ISSI risk is directly correlated with the size of surgical incision used to perform the case. These risks are further compounded when combined with other risk factors such as obesity. For example, the rates of wound infections in obese patients undergoing colorectal surgery increase to upwards of 33%, representing a major burden to the healthcare system in terms of the quality and cost of services.

Prior surgical instruments and methods have been developed with the aim of reducing wound infections. Some solutions have addressed the issue by implanting degradable sponges in the incision to combat the development of wound infections post-operatively. However, this approach led to increases in wound infection rates, as the immune system reacts poorly to the implant because the implant is a "foreign body."

Surgeons have previously irrigated the incision or wound margins with fluids such as saline and/or antibiotics, but the practice has proved to be disruptive to surgical progress, difficult to implement and standardize in surgical practices, and consumes valuable time, increasing patient risk and increasing operative costs. It would therefore be desirable to provide for easier application and/or removal of fluids during the surgical procedure.

Barrier wound protectors have also been employed to prevent the egress of bacteria into the incision, but this is merely a passive approach, and considering the barrier protection must be removed to complete the operation, the incision is inevitably exposed to the infectious contents contained within the surgical field. Additionally, wound protectors may be difficult to manipulate, especially when positioned in the surgical field. A further drawback is that the barrier can also trap bacteria onto the wound surface, allowing bacteria to proliferate in the wound space.

Considering the significant morbidity and cost associated with SSI, it may be desirable to provide a way to reduce the occurrence of SSI that is superior to the limitations of currently available commercial devices.

In addition to the challenges mentioned previously, in select situations, a key aspect of surgery involves obtaining adequate surgical "exposure," or alternatively, adequate visualization and access to target anatomical landmarks and structures to be operated upon. To achieve proper exposure, surgeons can use a variety of surgical retractors generally configured to maximize the opening of the incision and create space within the operative region (e.g. chest, abdomen, orbit, neck, and groin) to facilitate the completion of the surgical procedure.

One surgical retractor used in abdominal surgery involves a top ring, bottom ring, and flexible tubular sheath disposed between the top and bottom rings. In numerous embodiments, manipulation of the top ring in a variety of ways (e.g., by rolling the sheath around the top ring) is sometimes effective to shorten the sheath length and retract the edges of the incision. In many cases, such surgical retractors incorporate barrier wound protection, the potential disadvantages of which have already been described.

The potential drawbacks of surgical retractors described in currently available commercial devices are numerous. They can be difficult to use, often requiring additional time and the manual application of forces that may be difficult for surgeons to apply in an operative setting. They may require more than one person to operate, decreasing focus on the operative field, increasing operative time and personnel costs. In addition, due to the unpredictable nature of a surgical operation, the initial incision size may not be ideal, thus requiring lengthening during the course of the procedure. Many commercially available surgical retractors do not allow for an increase in incision size with the device in situ. Moreover, currently available commercial surgical retractors may employ a design requiring a variety of sizes to accommodate the wide range of incision sizes encountered during surgery. As a result, hospitals may have to stock a range of device sizes, and often multiple devices are used in a single procedure as the size of the incision may be increased. Using multiple devices may result in increased healthcare costs, surgery duration, and infections. It would therefore be desirable to provide a device which is easily deployable and/or adjustable.

SUMMARY OF THE INVENTION

It would therefore be desirable to provide improved surgical retractors which address at least some of the possible shortcomings of existing devices. Moreover, it would also be desirable if improved surgical retractors helped to reduce the incidence of SSI. At least some of these objectives are met by the exemplary embodiments described below. Not necessarily all such aspects or advantages are achieved by any particular embodiment. Thus, various embodiments may be carried out in a manner that achieves or optimizes one advantage or group of advantages taught herein without necessarily achieving other aspects or advantages as may also be taught or suggested herein. For example, some embodiments reduce SSI but do not necessarily provide access to structures upon which a physician needs to operate. Several of the embodiments improve upon prior art retractors by transforming the retractors into systems that reduce SSI. Several embodiments provide access to structures upon which a physician needs to operate but do not necessarily reduce SSI.

As noted previously, it may be advantageous to incorporate the combined functions of fluid delivery and fluid removal into a retraction device configured to reduce the risk of SSI. Proposed embodiments of such a device may provide fluidic functions that are generally disposed along or near a pliable membrane, and that are configured to provide barrier wound protection (preventing direct contamination of the wound edges) and retraction of the surgical would to permit visualization and access to the surgical site.

While these devices are promising, in certain circumstances, they can suffer from a few minor drawbacks including: (1) the necessity of cumbersome fluid delivery and fluid removal tubes placed within or about the wound margins (which may be prone to kinking in these tight spaces); (2) the unpredictable/uncontrolled locations of the fluid delivery and fluid removal elements, potentially leading to fluid delivery outside of the wound (either intra-abdominally or on the skin), which is undesirable; (3) the additional or separate component requirements for constructing the fluid delivery and/or fluid removal components, increasing manufacturing cost and/or difficulty.

Therefore, it would be desirable to provide improved surgical devices, systems, and methods that address SSI. Such devices and methods of use preferably are easier to use, optimize fluid management within the surgical wound, and reduce manufacturing costs and complexity. At least some of these objectives will be met by the embodiments disclosed below.

The present invention generally relates to medical devices, systems, and methods, and more particularly relates to methods and apparatus used to facilitate access to a surgical site and/or prevention of surgical site infection.

An aspect of the present disclosure provides for a surgical access device adapted to facilitate access to a surgical site within a body of a patient through an incision in the body comprising a first retention member, a second retention member, and a pliable membrane extending therebetween. The second retention member is configured to lie in a plane above the incision. The second retention member is configured to expand in the plane from a collapsed configuration to an expanded configuration. The second retention member comprises at least three linkages pivotably coupled to one another such that actuation of the at least three linkages causes the at least three linkages to pivot relative to one another thereby radially expanding or collapsing the second retention member. The pliable membrane is configured to engage and expand the incision to facilitate access to the surgical site when the second retention member is in the expanded configuration.

Optionally, the device further may comprise a locking mechanism coupled to one or more inner pivots of the second retention member. Alternatively or in combination, the locking mechanism may be coupled to one or more outer pivots of the second retention member. Alternatively or in combination, the locking mechanism may be coupled to one or more middle pivots of the second retention member. The locking mechanism may comprise one or more posts and a locking plate with one or more engagement features shaped to correspond to the one or more posts. Alternatively or in combination, the locking mechanism may comprise a bar slidably disposed within a window of an arm.

Optionally, the device may further comprise a locking mechanism coupled to one or more inner pivots, one or more outer pivots, one or more middle pivots, or any combination thereof of the second retention member.

Optionally, the second retention member may comprise a smooth outer perimeter. The three or more linkages of the second retention member may be configured to overlap in the expanded configuration.

Optionally, the second retention member may comprise one or more intermediate configurations between the collapsed configuration and the expanded configuration. The second retention member may comprise an infinite number of intermediate configurations between the collapsed configuration and the expanded configuration.

Optionally, the pliable membrane may comprise a fluid delivery region disposed near the first retention member. The fluid delivery region may comprise a continuous base near the first retention member and a plurality of fingers extending towards the second retention member. Alternatively or in combination, the fluid delivery region may be positioned within the pliable membrane so as to prevent fluid from spilling out of the incision. Alternatively or in combination, the fluid delivery region may comprise a foam manifold.

Optionally, the first retention member may comprise a lumen and a plurality of holes in fluid communication with the lumen.

Optionally, the first retention member may comprise a D-shaped cross-section. An inferior end of the pliable membrane may be coupled to a bottom perimeter or an outer perimeter of the first retention member.

Optionally, the first retention member may be coupled to an inferior end of the pliable membrane in order to form a trough therebetween.

Another aspect of the present disclosure provides for a surgical access system adapted to facilitate access to a surgical site within a body of a patient through an incision in the body comprising a first retention member configured for placement within the body at or near the surgical site, a second retention member configured for placement outside the body, and a pliable membrane extending between the first retention member and the second retention member. An inferior portion of the pliable membrane near the first retention member comprises a fluid delivery region in fluid communication with a fluid delivery member. The fluid delivery region comprises at least one perforation therein to allow fluid introduced into the fluid delivery region via the fluid delivery member to exit the surgical access system.

Optionally, the second retention member may lie in a plane above the incision and is configured to expand from a collapsed configuration to an expanded configuration in the plane.

Optionally, the fluid delivery region may comprise a continuous base near the first retention member and a plurality of fingers extending towards the second retention member. Each of the plurality of fingers may comprise at least one perforation configured to allow fluid to flow therefrom.

Optionally, the fluid delivery region may be positioned within the pliable membrane so as to prevent fluid from spilling out of the incision.

Optionally, the pliable membrane may comprise an inner layer and an outer layer. The fluid delivery region may comprise a foam manifold sealed between the inner layer and outer layer to form a space therebetween. Alternatively or in combination, the inner layer may comprise an impermeable material and the outer layer comprises a permeable material.

Optionally, the system may further comprise the fluid delivery member. The fluid delivery member may be coupled to the fluid delivery region adjacent the first retention member such fluid provided by the fluid delivery member fills the fluid delivery region in a bottom-up manner.

Optionally, the system may further comprise a fluid removal member. The first retention member may comprise a lumen in fluid communication with the fluid removal member and a plurality of holes in fluid communication with the lumen.

Another aspect of the present disclosure provides for a method for retracting tissue of a surgical site of a body comprising: inserting at least a portion of a surgical access device into an incision, wherein the surgical access device comprises a first retention member, a second retention member, and a pliable membrane coupled between the first retention member and the second retention member; advancing the first retention member into the body through the incision; placing the second retention member outside the body; retracting the tissue using the pliable membrane; and delivering fluid from the pliable membrane to the incision.

Optionally, the pliable membrane may comprise a fluid delivery region disposed near the first retention member. Delivering fluid from the pliable membrane to the incision may comprise delivering fluid from the fluid delivery region to the incision. The fluid delivery region may comprise a continuous base near the first retention member and a plurality of fingers extending towards the second retention member. Each of the plurality of fingers may comprise at least one perforation configured to allow fluid to flow therefrom. Delivering fluid from the fluid delivery region to the incision may comprise delivering fluid from the at least one perforation of each of the plurality of fingers to the incision.

Optionally, the fluid delivery region may be positioned within the pliable membrane so as to prevent fluid from spilling out of the incision. Delivering fluid from the pliable membrane to the incision may occur without spilling the fluid out of the incision and into the surgical site.

Optionally, the method may comprise suctioning at least a portion of the fluid into the surgical access device and removing the portion from the body. The first retention member may comprise a lumen and a plurality of holes in fluid communication with the lumen. Suctioning at least a portion of the fluid into the surgical access device may comprise suctioning at least a portion of the fluid into the lumen via the plurality of holes.

Optionally, the second retention member may lie in a plane above the incision and may be configured to expand from a collapsed configuration to an expanded configuration in the plane. Retracting the tissue with the pliable membrane may comprise expanding the second retention member from the collapsed configuration to the expanded configuration to tension the pliable membrane against the incision. Alternatively or in combination, retracting the tissue with the pliable membrane may comprise expanding the second retention member from the collapsed configuration to an intermediate configuration between the collapsed configuration and the expanded configuration to tension the pliable membrane against the incision.

Optionally, the method may further comprise locking the second retention member in the expanded configuration with a locking mechanism coupled to the second retention member.

Optionally, the method may further comprise locking the second retention member in the intermediate configuration with a locking mechanism coupled to the second retention member.

Optionally, the fluid may comprise an antibiotic fluid or a saline solution.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 17A-17B show isometric bottom views of the superior retention member of FIG. 15, in accordance with embodiments;

DETAILED DESCRIPTION OF THE INVENTION

Figure 1:
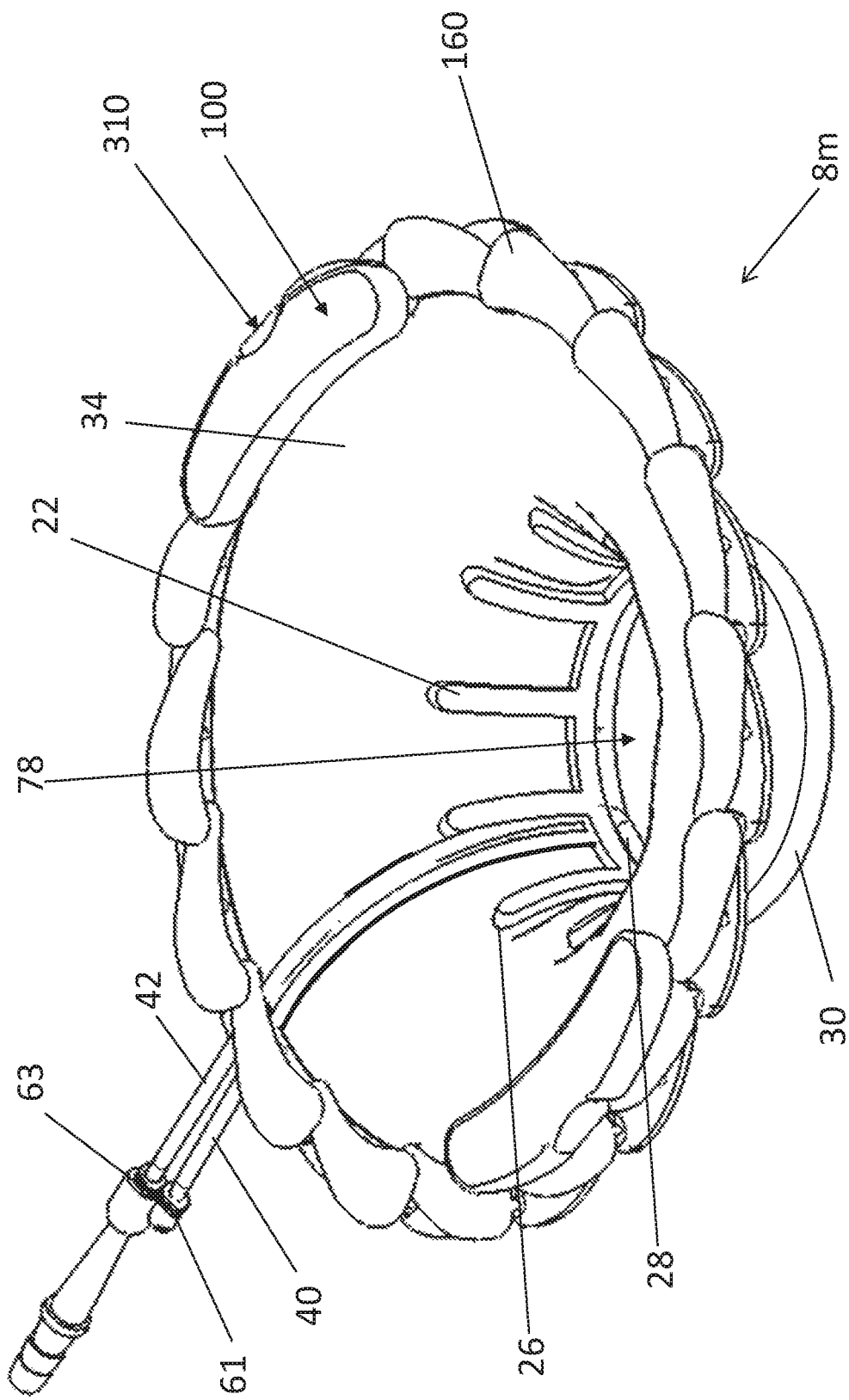
FIG. 1 shows an isometric top view of an exemplary surgical access device, in accordance with embodiments.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments, however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The present disclosure will be described in relation to the deployment of the device or treatment of a wound during abdominal surgery. However, one of skill in the art will appreciate that this is not intended to be limiting and the devices and methods disclosed herein may be used in other anatomical areas and in other surgical procedures. Anatomical areas may, for example, include joint compartments, limb compartments, the thoracic cavity, the stomach, the colon, the rectum, the small intestine, the pancreas, the abdominal cavity, superficial incisions, the skin, natural body orifices, the breast, the uterus, the brain calvarium, the neck, the back or spine, or any other anatomical area known to one or ordinary skill in the art. Procedures may, for example, include joint replacement, arthroplasty, bone fixation, coronary artery bypass grafting, lobectomy, colorectal surgery, small intestine surgery, bariatric surgery, stomach surgery, pancreatic surgery, skin cancer removal, diabetic ulcer treatment, pressure ulcer treatment, mastectomy, hysterectomy, C-section, thyroid surgery, or other surgical procedures which may leave a wound and thus the potential for developing a surgical site as known to one of ordinary skill in the art.

As noted previously, it may be advantageous to incorporate the combined functions of fluid delivery and fluid removal into a retraction device configured to reduce the risk of surgical site infections. Proposed embodiments of such a device may provide fluidic functions that are generally disposed along or near a pliable membrane, and that are configured to provide barrier wound protection (preventing direct contamination of the wound edges) and retraction of the surgical wound to permit visualization and access to the surgical site. U.S. Pat. Nos. 9,393,005 and 10,085,734 and U.S. patent application Ser. Nos. 16/121,484 and 13/736,904 disclose further details about such a device, the entire contents of which are incorporated herein by reference. Methods of using such a device are also disclosed in U.S. Pat. Nos. 9,084,594 and 9,788,823 and U.S. patent application Ser. No. 15/344,407, the entire contents of which are incorporated herein by reference. Additional disclosure about various features which may be used in such a device are disclosed in U.S. Pat. Nos. 9,402,612, 9,974,564, and 9,610,096 and U.S. patent application Ser. Nos. 15/597,381 and 15/344,407, the entire contents of which are incorporated herein by reference. While these embodiments are preferred due to their ability to accommodate a range of incision sizes, their ability to increase the size of the incision without removing the retraction device from the surgical field, and their speed of use, among other benefits, it may be beneficial to implement fluid delivery and optionally fluid evacuation with other commercially available retractors. One such exemplary commercial retractor includes a dual ring wound retractor design described in U.S. patent application Ser. Nos. 12/873,115, and 12/119,414; U.S. Pat. Nos. 5,524,464, 7,238,154, 6,254,533, 6,814,078, 6,382,211, 8,021,296, and 8,012,088, among others. Generally, these devices are comprised of a cylindrical sheath disposed between a top and bottom ring. Shortening of the cylindrical sheath is generally effective to retract the wound opening, thereby permitting completion of a surgical procedure therethrough. It may be beneficial to combine fluid delivery and optionally fluid evacuation features with these devices to provide the advantages previously discussed above.

A preferred embodiment of a surgical device utilizes an integrated pliable membrane design that provides a barrier for wound protection and that may directly incorporate fluid delivery and removal in a single assembly. The surgical device may include any combination of features described herein to provide for wound retraction, wound protection, fluid delivery, and/or fluid removal.

Figure 2:
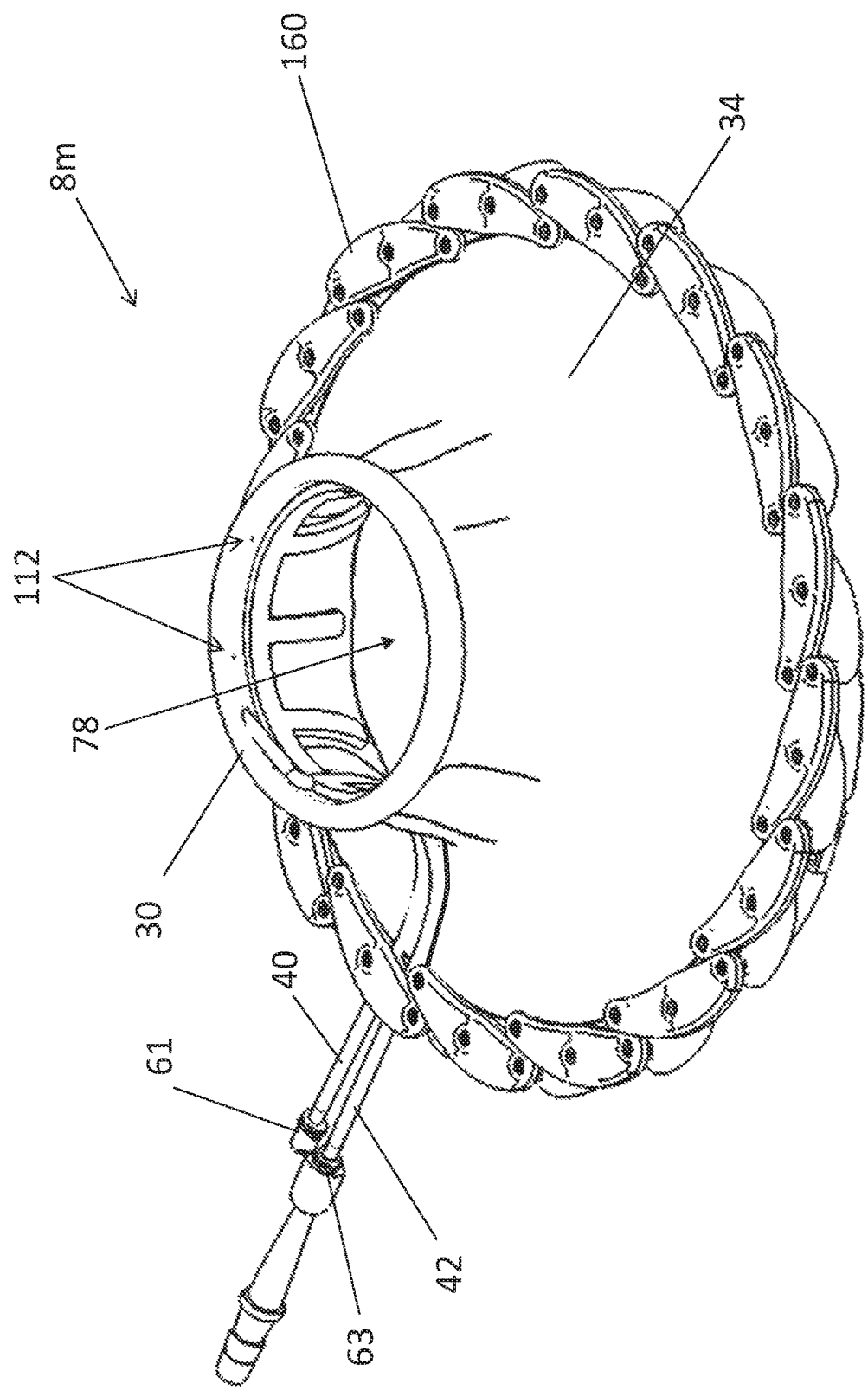
FIG. 2 shows an isometric bottom view of the surgical access device of FIG. 1, in accordance with embodiments.

FIG. 1 shows an isometric top view of an exemplary surgical access device 8*m*. FIG. 2 shows an isometric bottom view of the surgical access device 8*m*. The surgical device 8*m* may comprise an expanding linkage structure 160 (also referred to herein as a retraction ring, superior retention member, expandable retention member, or second retention member), a pliable membrane 34, and a retention ring 30 (also referred to as an inferior retention member or first retention member). The pliable membrane 34 may extend between the first retention member 30 and the second retention member 160. The pliable membrane 34 may comprise a tubular membrane having a substantially cylindrical or frustoconical shape with a central channel 78 defined therein by the inner wall of the pliable membrane 34. The central channel 78 may be open so as to facilitate access to the surgical site.

The surgical device 8*m* may, optionally, further comprise a locking mechanism 310, for example the locking plate mechanism 300 described in FIGS. 22-26 or the sliding bar mechanism 340 described in FIGS. 27-32. The locking mechanism 310 may be used to selectively constrain the expanding linkage structure 160 in a desired configuration as described herein. The locking mechanism 310 may prevent collapse of the expandable retention member 160 when not engaged by a user as described herein. Engagement and release of the locking mechanism 310 may allow the user to collapse the retention member 160 radially inward or expand the retention member 160 radially outward. Radially inward collapse of the retention member 160 may reduce tension on the pliable membrane 34 and allow the surgical access device 8*m* to be removed or adjusted. Radial collapse of the expanding linkage structure 160 may provide a smooth closure motion which may reduce splashing of bodily fluids thereby reducing contamination. Radially outward expansion of the retention member 160 may increase tension on the pliable membrane 34 and cause the pliable membrane 34 to engage and expand an incision or wound as described herein. The pliable membrane 34 and/or the retention member 160 of the surgical device 8m may be expanded or collapsed in a single, contiguous motion. The pliable membrane 34 and/or the retention member 160 of the surgical device 8m may be expanded or collapsed in a step-wise motion.

The locking mechanism 310 may be disposed inside a handle 100. In some instances, more than one locking mechanism 310 and more than one handle 100 may be affixed to the expandable retention member 160. For example, the expandable retention member 160 may comprise two locking mechanisms 310 inside two handles 100 symmetrically disposed on the expandable retention member 160. In some instances, providing two handles 100 with two locking mechanisms 310 therein may provide the user with improved control of expansion and collapse of the expandable retention member 160. Alternatively or in combination, the dual handle 100 configuration may help to prevent canting of the expandable retention member 160 by reducing off-axis loading applied by the user.

Figure 6:
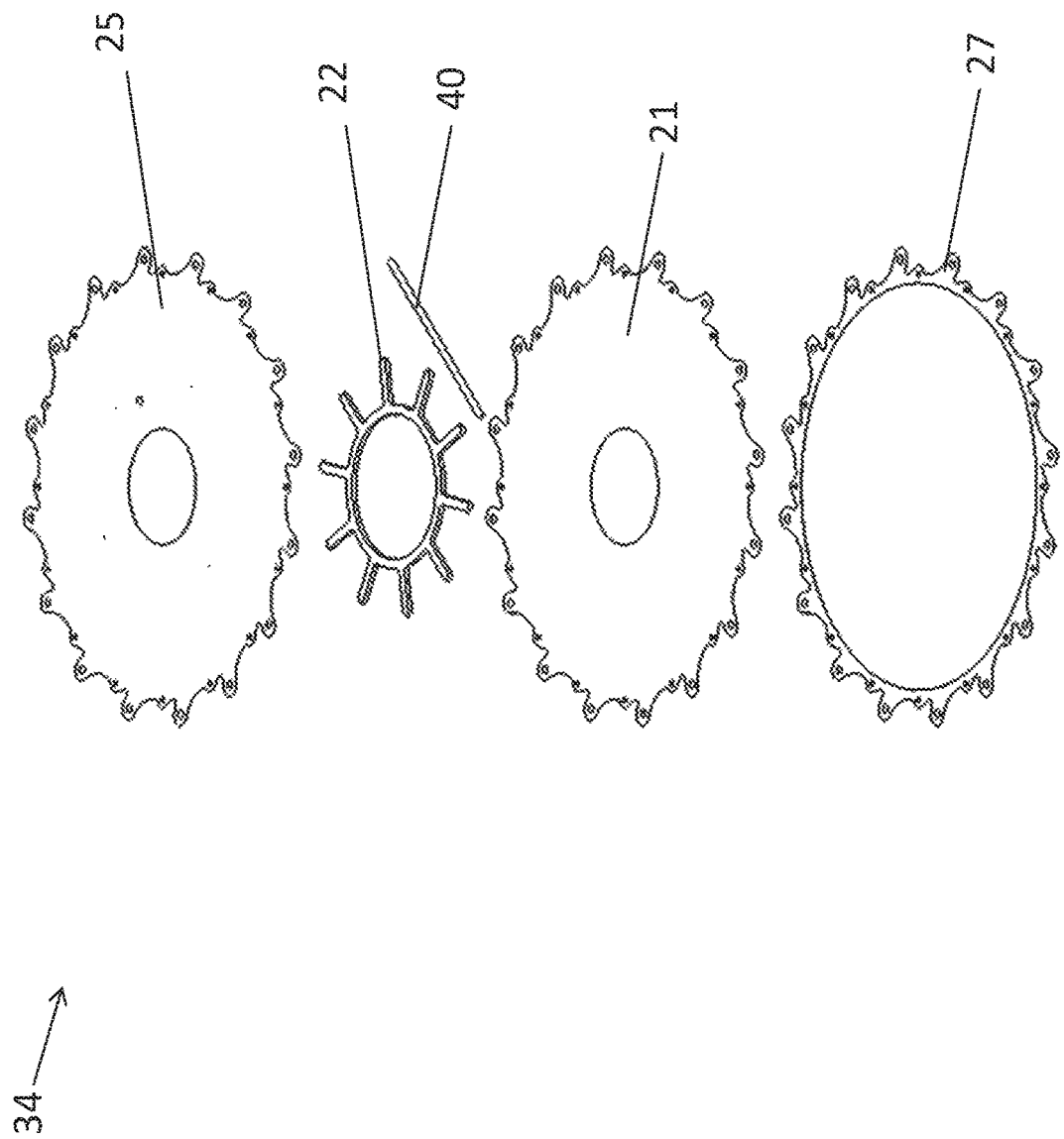
FIG. 6 shows an exploded view of an exemplary planar pliable membrane, in accordance with embodiments.

The surgical device 8m may, optionally, further comprise fluid delivery as described herein. For example, a fluid delivery member 40 may be coupled to the pliable membrane 34 so as to provide fluid to the surgical site via perforations in the pliable membrane 34 as described herein. The fluid delivery member 40 may be coupled to a fluid source via a fluid delivery connector 61, for example a luer lock fitting. The pliable membrane 34 may comprise a fluid delivery region (for example fluid delivery region 60 described herein) between an inner layer (for example impermeable layer 21) and an outer layer (for example permeable layer 25) of the pliable membrane 34 in fluid communication with the fluid delivery member 40. The fluid delivery region may be formed around a foam manifold 22 disposed within the pliable membrane 34. In some instances, the foam manifold 22 may be shaped like a "sunburst" when in its planar configuration (as shown in FIG. 6). When in its tubular configuration, the foam manifold 22 may comprise a continuous base portion 28 forming the "sun" coupled near the inferior end of the pliable membrane 34 and fingers 26 extending upwards therefrom and forming the "rays". Each of the fingers 26 may comprise one or more perforations in the outer layer of the pliable membrane 34 which allow fluid to be delivered from the fluid delivery region to the target surgical site as described herein.

Alternatively or in combination, the surgical device 8m may further comprise fluid removal as described herein. For example, a fluid removal member 42 may be coupled to one or more of the pliable membrane 34 or the inferior retention member 30 so as to remove fluid from the surgical site. In some embodiments, the fluid removal member 42 may be coupled to a hollow inferior retention member 30 as described in FIG. 11. The fluid removal member 42 may be in fluid communication with a lumen of the inferior retention member 30. The fluid removal member 42 may be coupled to a suction device via a fluid removal connector 63, such as a barbed connector. The hollow inferior retention member 30 may comprise one or more fluid removal holes 112 disposed along an inner circumference of the retention member 30 which allow fluid to enter the lumen of the inferior retention member 30 from the surgical site as described herein.

In many instances, it may be beneficial to provide a surgical device 8m which may be operated by a single user. Other wound protection devices often require two or more people to operate as tension is provided by evenly rolling a membrane around a retention ring. The surgical device 8m may be configured such that the user may operate the device with one hand or both hands. Operation of the surgical device 8m may include expanding the device 8m, collapsing the device 8m, irrigating the wound, removing fluid, or any combination thereof.

The surgical device or any of its components may have any of the features described herein or in the following patents and applications: U.S. Pat. Nos. 9,393,005, 9,084, 594, 9,402,612, 9,788,823, 9,610,096, 9,974,564, 10,085, 735 and U.S. patent application Ser. Nos. 13/736,904, 14/220,928, 62/488,105, 62/501,877, 15/344,407, 15/957, 381, and 16/121,484; the entire contents of which are incorporated herein by reference, in any combination of features.

Figure 3:
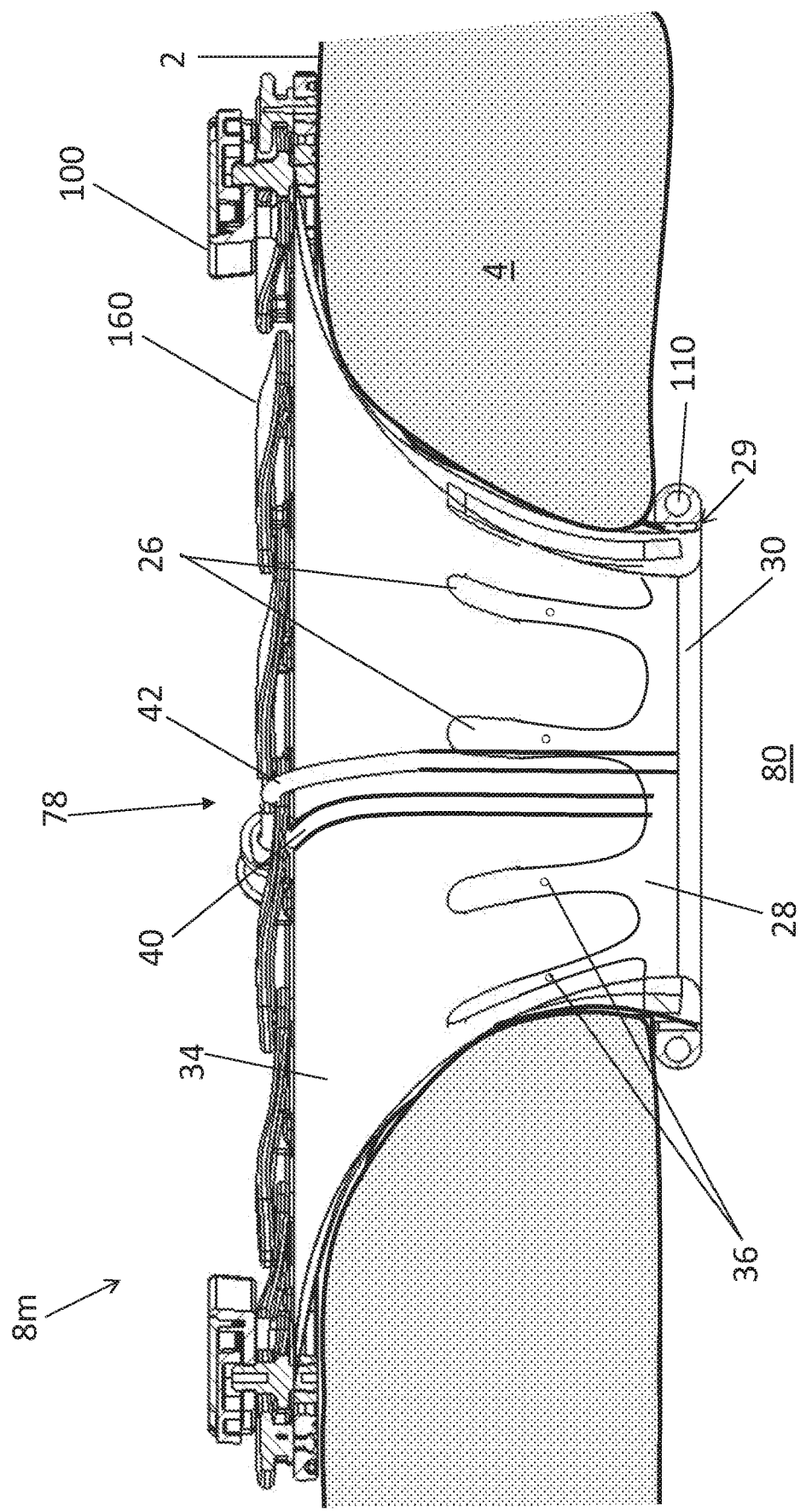
FIG. 3 shows a cross-sectional view of the surgical access device of FIG. 1 disposed in an incision, in accordance with embodiments.
Figure 4:
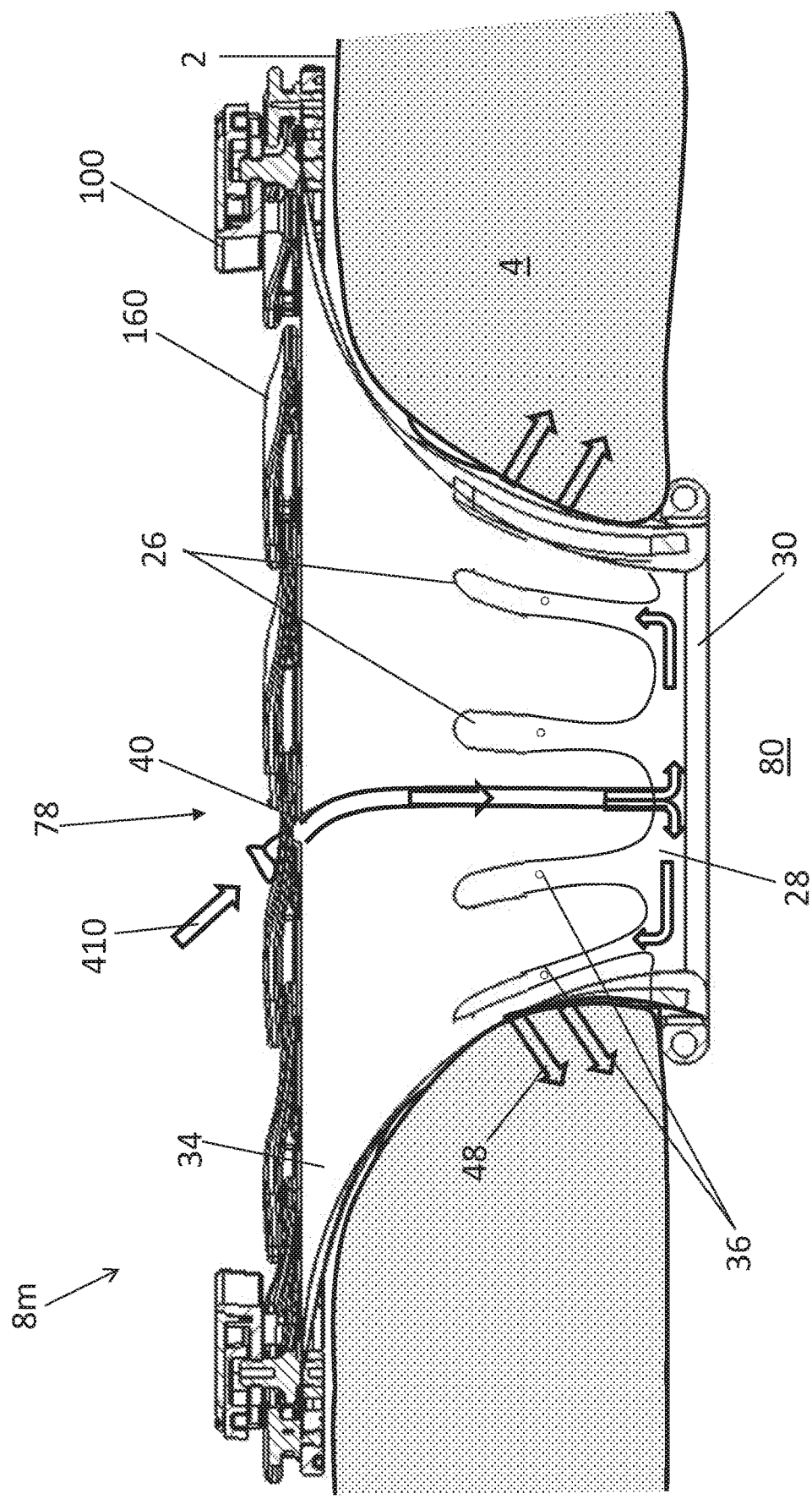
FIG. 4 shows a cross-sectional view of another surgical access device disposed in an incision, in accordance with embodiments.
Figure 5:
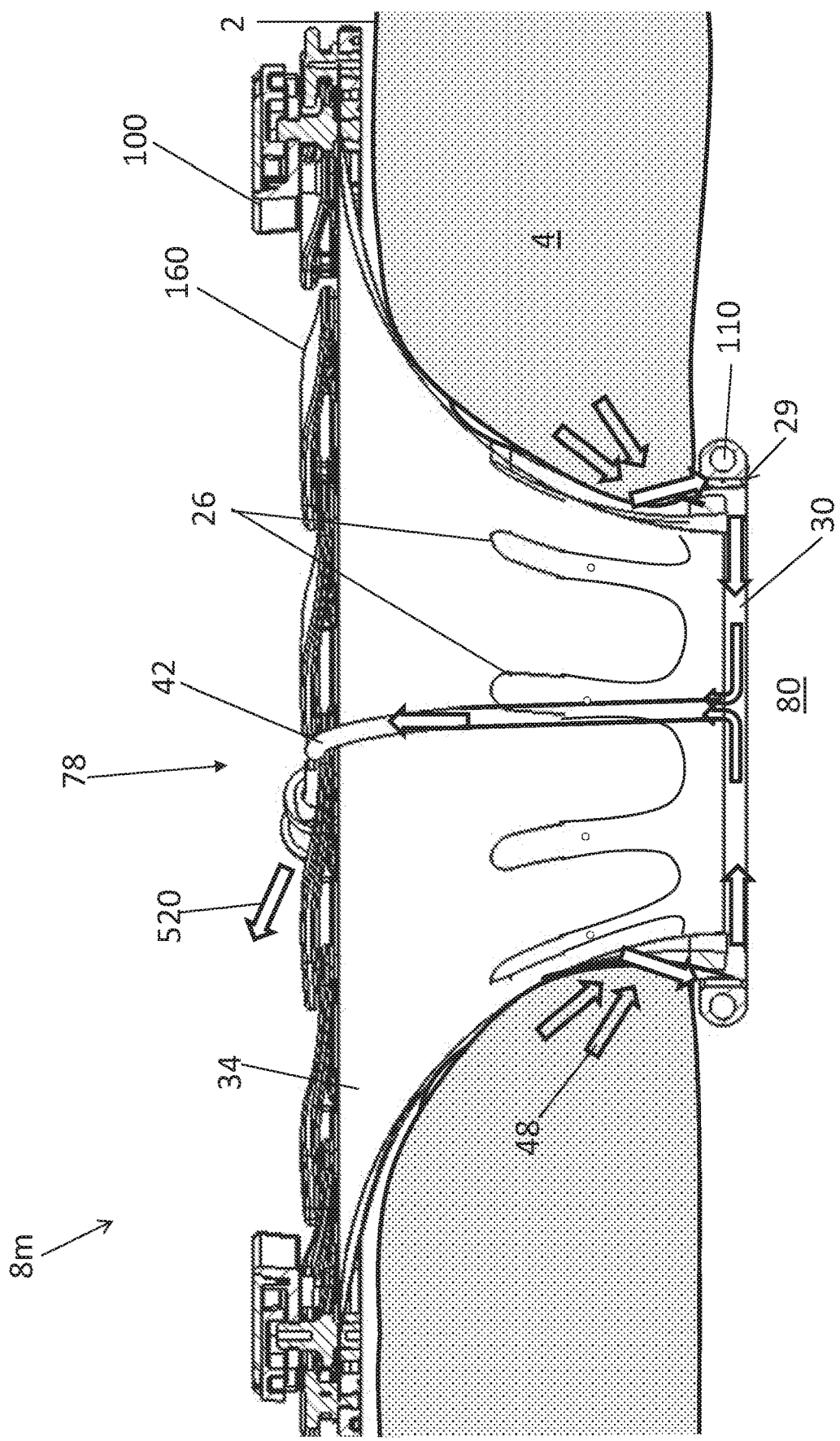
FIG. 5 shows a cross-sectional view of yet another surgical access device disposed in an incision, in accordance with embodiments.

FIGS. 3-5 show cross-sectional views of the surgical access device 8m disposed in an incision 4. The surgical access device 8m may comprise a first retention member 30, a second retention member 160, and a pliable membrane 34 therebetween as described herein. The surgical access device 8m may optionally comprise a fluid delivery member 40 and/or a fluid removal member 42 fluidly coupled thereto as described herein. FIG. 3 shows a surgical device 8m comprising both fluid delivery and fluid removal functions in a single device. The fluid delivery function of the device 8m is described in detail with relation to FIG. 4. The fluid removal function of the device 8m is described in detail with relation to FIG. 5.

The surgical access device 8m may provide a path through the skin 2 and wound 4 (for example subcutaneous fat and/or muscle) to facilitate access to a target site 80. The first retention member 30 may comprise a resilient, deformable material in order to facilitate advancement of the first retention member 30 through the incision or wound 4 and into the patient's body. The first retention member 30 may be elastically deformable such that it may be squeezed into a smaller compressed configuration for insertion into the body and, upon release of the compressive force, resiliently return to its original shape within the patient's body. The second retention member 160 may comprise a plurality of pivotably coupled linkages and may be configured to be placed outside of the patient's body. The second retention member 160 may lie in a plane above the patient's skin when the surgical device 8m is inserted into the wound 4. Expansion of the second retention member 160 in the plane while the first retention member 30 and pliable membrane 34 are disposed in the body of the patient may tension the pliable membrane 34 against the walls of the incision or wound 4. The pliable membrane 34 may be sufficiently tough or strong (e.g. rigid) so as to expand the incision or wound 4 to provide access to the surgical site 80 upon further expansion of the second retention member 160 and increased tension applied to the pliable membrane 34. Expansion of the pliable membrane 34 may expand the central channel 78 running therethrough and through which the user may access the surgical site 80. The central channel 78 may remain patent (i.e. open) in both the expanded configuration and the collapsed configuration of the second retention member 160, and in any intermediate state therebetween.

In some instances, the second retention member 160 may lie approximately in a plane above the patient's skin during placement and/or during expansion. For example, the pliable membrane 34 may experience non-uniform force from the incision which may cause the second retention member 160 to buckle away from the plane above the patient's skin during placement and/or during expansion. Such buckling may, for example, be due in part to gaps between posts of the linkages. In such cases, the second retention member 160 may be configured to maintain one or more angles, at any point along the second retention member 160, of no more than about 30° away from the desired plane, for example no more than about 10° above or below the plane above the patient's skin. In some cases, parts of the second retention member 160 may buckle away from the plane at a first angle while other parts may rest at a second, different angle, such that the outer edges forms define a sinusoidal curve with respect to the flat plane above the patient's skin, the points of the outer edges defining a curved surface.

In many cases, the central channel 78 running through the pliable membrane 34 and providing access to the surgical site 80 may remain open for the duration of the surgical procedure. In some embodiments, it may be beneficial to seal the wound 4 and prevent access to the surgical site 80 during surgery without removing the surgical device 8m from the wound 4, for example to temporarily seal the site 80 against gas and/or liquids. The surgical device 8m may be configured such that rotation of the expanding linkage structure 160 relative to the first retention member 30, without release of the locking mechanism 310, causes the pliable membrane 34 to twist between the expanding linkage structure 160 and the retention ring 30 to effectively seal the central channel 78. The device 8m may be configured such that the fluid removal and/or suction functions of the device still function when a zero seal is created by twisting the expanding linkage structure 160 relative to the retention ring 30.

The surgical device 8m may be used to provide retraction of a surgical wound or incision 4 for surgical access as well as irrigation and suction. In some embodiments, the surgical device 8m may be configured to provide retraction without fluid delivery or removal. In some embodiments, the surgical access device 8m may be configured to provide fluid delivery and fluid removal without retraction.

FIG. 4 highlights the fluid delivery function of the surgical device 8m. The surgical device 8m may comprise fluid delivery as described herein. For example, a fluid delivery member 40 may be coupled to the pliable membrane 34 so as to provide fluid to the surgical site via perforations 36 in the pliable membrane 34. The fluid delivery member 40 may be coupled to a fluid source via a fluid delivery connector 61, for example a luer lock fitting.

The pliable membrane 34 may comprise a fluid delivery region (for example fluid delivery region 60 described herein) between an inner layer (for example impermeable layer 21) and an outer layer (for example permeable layer 25) of the pliable membrane 34 in fluid communication with the fluid delivery member 40. The fluid delivery region may be formed around a foam manifold 22 disposed within the pliable membrane 34. In some instances, the foam manifold 22 may be shaped like a "sunburst" when in its planar configuration (as shown in FIG. 6). When in its tubular configuration, the foam manifold 22 may comprise a continuous base portion 28 forming the "sun" coupled near the inferior end of the pliable membrane 34 and fingers 26 extending upwards therefrom and forming the "rays". Each of the fingers 26 may comprise one or more perforations 36 in the outer layer of the pliable membrane 34 which allow fluid to be delivered from the fluid delivery region to the target surgical site as described herein.

The fluid delivery member 40, base portion 28, and fingers 26 may form a part of a fluid delivery pathway 410 which is illustrated here by arrows. The fluid 48 may be introduced into the fluid delivery region of the pliable membrane 34 comprising the sunburst-shaped continuous base portion 28 with fingers 26 extending upward therefrom by the fluid delivery member 40. The fluid delivery member 40 may be coupled at or near the base of the pliable membrane 34 so as to fill the fluid delivery region from the bottom-upwards. Filling the fluid delivery region from the bottom-up, instead of from the top-down, may result in better circumferential distribution of the fluid 48 within the fluid delivery region. Alternatively or in combination, filling from the bottom-up may mitigate the impact of wrinkling within the pliable membrane on the filing and delivery ability of the fluid delivery region by first delivering the fluid 48 into a taut bottom region instead of a potentially-wrinkled top portion of the pliable membrane 34. Furthermore, filling the fluid delivery region from the bottom-up may prevent or reduce the effects of pinching within the fluid delivery region which may otherwise prevent proper even distribution of the fluid 48 within the region. Fluid 48 may first fill the base portion 28 of the fluid delivery region before traveling upwards into the fingers 26. Upon reaching the perforations 36 and application of sufficient pressure, the fluid 48 may exit the pliable membrane 34 and be delivered to the wound tissue margin 4 therethrough.

The fluid delivery region may, for example, comprise a single continuous region within the pliable membrane 34 such that there are no folds or seams therein which may inhibit fluid flow therein. The fluid delivery region may be disposed within a portion of the pliable membrane. For example, the fluid delivery region may be disposed between an inner layer and an outer layer of the pliable membrane 34 near the inferior end of the pliable membrane 34 as described herein. By limiting the fluid delivery region to a portion of the pliable membrane 34, the volume of fluid 48 necessary to fill the fluid delivery region and reach the perforations 36 may be reduced. Additionally, proper selection of the location of the fluid delivery region, and in particular the location of perforations 36, may result in finer control of the location of fluid delivery to the wound 4 and thus a reduced risk of fluid delivery to unwanted tissue locations (for example to the skin 2 above the wound 4 or directly into the surgical site 80.

Each finger 26 may comprise one or more perforations 36. For example, each finger 26 may comprise a single perforation 36. Each of the perforations 36 may be disposed at or about the same height above the first retention member 30 in order to provide uniform fluid delivery as described herein. The height of the perforations 36 may vary based on the length of the incision 4 and the thickness of the patient's subcutaneous tissue. The perforations 36 may, for example, be located about ¼" to about 4" above the first retention member 30 so as to prevent fluid delivery to skin 2 or directly into target site 80, for example about ½", about ¾", about 1", about 1¼", about 1½", about 1¾", about 2", about 2¼", about 2½", about 2¾", about 3", about 3¼", about 3½", or about 3¾" above the first retention member 30. Alternatively or in combination, each of the perforations 36 may be sized and shaped similarly to one another in order to minimize differences in fluid resistance between the fingers 26 for improved delivery. The perforations 36 may, for example, have a diameter from about 0.005 to about 0.040 inches, for example about 0.010 inches, about 0.015 inches, about 0.020 inches, about 0.025 inches, about 0.030 inches, or about 0.035 inches. Alternatively or in combination, the perforations 36 may, for example, be created by piercing the material and not making a hole. Minimizing the size of the perforations 36 may help to release fluid pressure evenly around the circumference of the fluid delivery region. The foam manifold 22 disposed within the fluid delivery region may also help to minimize fluidic resistance along the fluid delivery path 410.

The fluid 48 may be delivered to the wound tissue margin 4 in order to irrigate the wound 4 and/or prevent the wound 4 from drying. Fluid 48 may be delivered to the wound margins 4 in order to reduce tissue desiccation. Reduction of tissue desiccation or drying may reduce the time required for the wound to heal after surgery. Fluid delivery, alone or in combination with sealing of the wound tissue by the pliable membrane 34 as described herein, may reduce or prevent tissue desiccation and/or replace any moisture lost from the tissue during surgery. Alternatively or in combination, fluid 48 may be delivered to the wound tissue 4 in order to treat the tissue with a therapeutic agent. The fluid 48 may, for example, comprise saline, antibiotics, or other therapeutic agents. Alternatively or in combination, the fluid delivery function of the surgical device 8*m* may be used for the cleansing of the wound surface by clearing away debris such as fat, bacteria, or other particles. Continuous delivery of a fluid 48 to the wound surface may cause a continuous flow across the wound surface that could wash debris, bacteria, or particles off of the wound surface and into the abdominal cavity or away from the surgical site via an optional fluid removal function.

Wound irrigation (i.e. fluid delivery) may be initiated by the user by manually triggering fluid delivery (e.g. by connecting the fluid source to the pliable membrane or by starting fluid flow on a pre-connected fluid source) or it may be initiated automatically (e.g. in response to the device being locked in an expanded position, etc.).

FIG. 5 highlights the fluid removal function of the surgical device 8*m*. The surgical access device 8*m* may optionally comprise a fluid removal member 42 fluidly coupled thereto as described herein. The fluid removal function of the surgical device 8*m* may be used to remove fluid 48 and debris from the surgical site and reduce the accumulation of debris, bacteria, or other particles in the abdominal cavity.

The fluid removal member 42 may form a part of a fluid removal pathway 520 which is illustrated here by arrows. The fluid 48 may enter the fluid removal pathway 520 after being delivered to the wound 4 by the pliable membrane 34 as described herein. Fluid 48 may flow down the wound margins 4 towards the first retention member 30. A trough 29 between the first retention member 30 and the pliable membrane 34 may collect the fluid 48 after it has exited the pliable membrane 34 and irrigated the wound 4 and prevent it from entering the surgical site 80. Fluid removal holes (such as holes 112 shown in FIG. 11) may be disposed along the internal edge of the first retention member 30 and in fluid communication with the trough 29 and a lumen 110 within the first retention member 30. The fluid 48 may flow from the trough 29 into the lumen 110 via the holes and then from the lumen 110 into the fluid removal member 42 and out of the surgical access device 8*m*.

FIG. 6 shows an exploded view of the pliable membrane 34. The pliable membrane 34 may comprise several layers of material laminated together. The pliable membrane 34 may include a base layer 21 (also referred to herein as an inner layer) such as an impermeable layer, a foam manifold 22, an outer layer 25 such as a (semi-)permeable layer, and/or a reinforcement layer 27. Assembly of the layers may form an integrated pliable membrane design that overcomes at least some of the challenges described herein.

The pliable membrane 34 may be configured to provide for fluid delivery to the wound space or surgical site. Fluid delivery may be provided by one or more perforations in the outer layer 25 and one or more channels or spaces defined between the outer layer 25 and the inner layer 21. Such channels or spaces may, for example, define a fluid delivery region as described herein. The fluid delivery member 40 may be coupled to the foam manifold 22 and enclosed between the outer layer 25 and the inner layer 21. Providing the fluid delivery member 40 within the pliable membrane 34 structure may reduce the number of moving parts inserted into the incision and improve usability of the surgical access device. In some instances, the fluid delivery member 40 may comprise a fluid delivery tube or conduit having a fluid outlet disposed at the base of the fluid delivery region. Alternatively or in combination, the fluid delivery member 40 may comprise a channel formed between the outer layer 25 and the inner layer 21 without additional materials or structures therebetween.

The outer layer 25 may comprise a permeable, or semi-permeable, material in order to facilitate fluid movement from the fluid delivery region to the wound 4. The outer layer 25 may have perforations (for example perforations 36 as shown in FIGS. 3-5) defining fluid exit locations which permit fluid delivery to the wound, delivered via the fluid delivery member 40 in connection with an externally pressured fluid source.

The inner layer 21 may comprise an impermeable material in order to prevent fluid from moving from the fluid delivery region to the central channel 78 and obscuring the surgical field. In some instances, the impermeable layer 21 may comprise one or more holes therein configured to facilitate manufacturing and shipping of the assembled pliable membrane 34 prior to use. The holes may be placed such that the impermeable layer 21 remains impermeable to fluid at the fluid delivery region and no fluid flows into the central channel 78 during use.

The layers of the pliable membrane 34 may, for example, be sealed together using heat sealing, RF welding, or other methods of attachment which will be known to one of ordinary skill in the art. The inner layer 21 and the outer layer 25 may be welded together so as to capture the foam manifold layer 22 therebetween and form the fluid delivery region.

The foam manifold layer 22 may be comprised of reticulated (open-cell) thermoplastic polyurethane (TPU) or polyethylene foam, and may be approximately 0.125" thick. The reinforcement layer 27 may be comprised of 0.006" thick TPU. The other two layers 21 and 25 of the design may be comprised of 0.003" thick TPU.

In some instances, one or more fluidly independent channels (or chambers) may be defined between the outer layer 25 and the inner layer 21 and configured to provide a plurality of locations for fluid delivery.

Additional details about the pliable membrane and how it may be manufactured and used for fluid delivery, fluid removal, and wound retraction are disclosed in U.S. Pat. Nos. 9,402,612, 9,974,564, and 9,610,096 and U.S. patent application Ser. No. 15/957,381; the entire contents of which are incorporated herein by reference.

Figure 7:
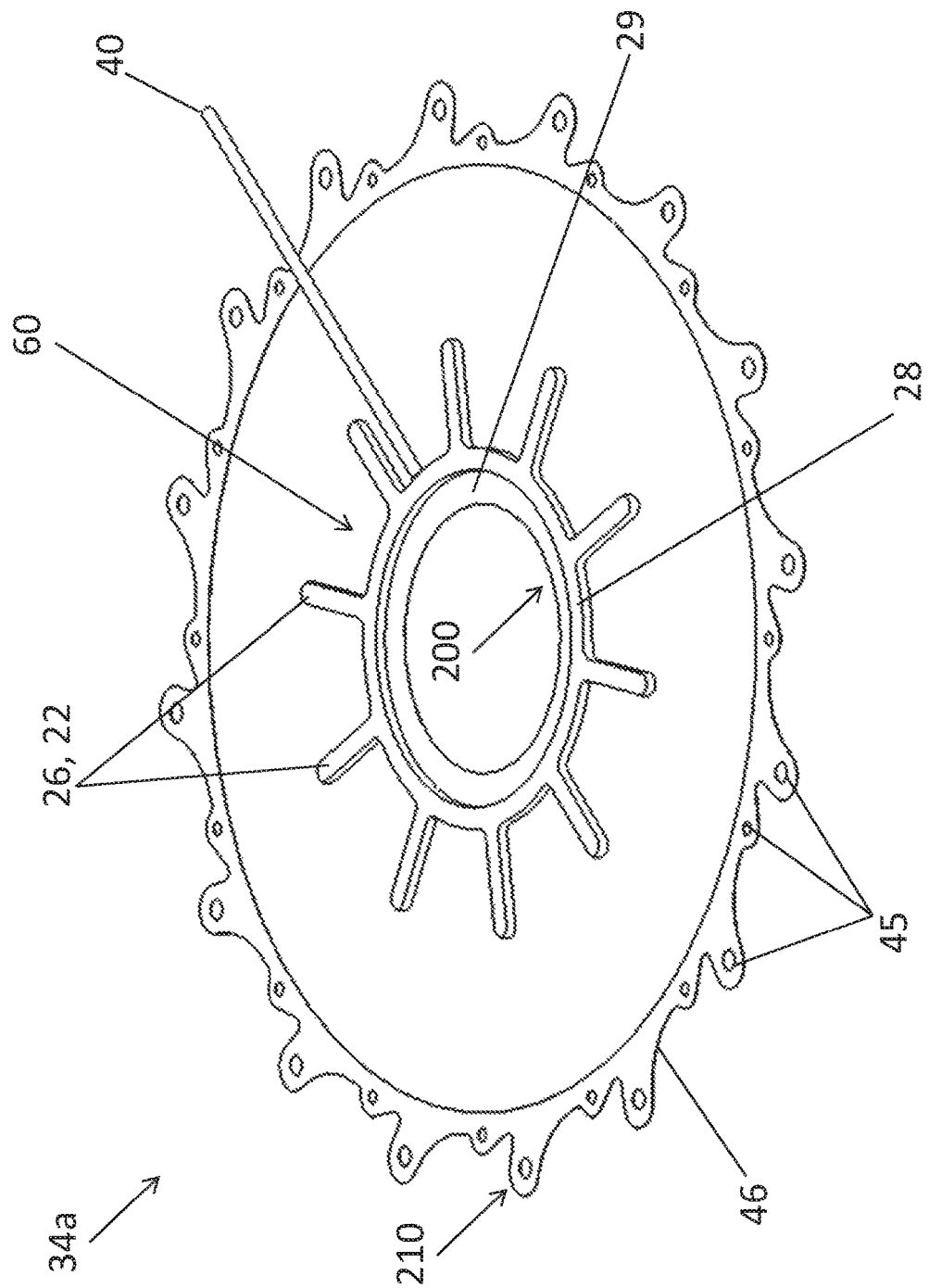
FIG. 7 shows an isometric view of the pliable membrane of FIG. 6, in accordance with embodiments.
Figure 8:
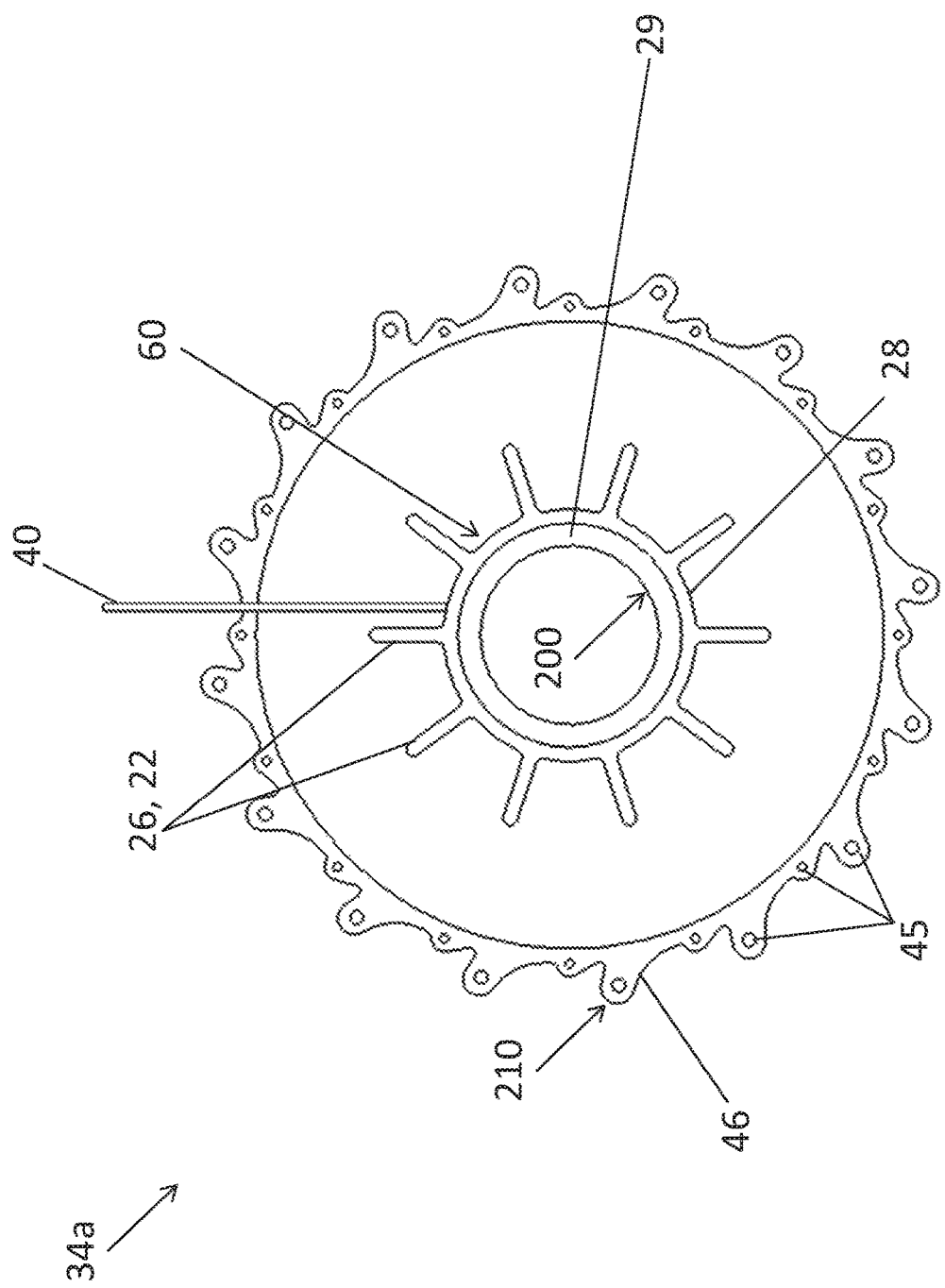
FIG. 8 shows a plan view of the pliable membrane of FIG. 6, in accordance with embodiments.
Figure 9:
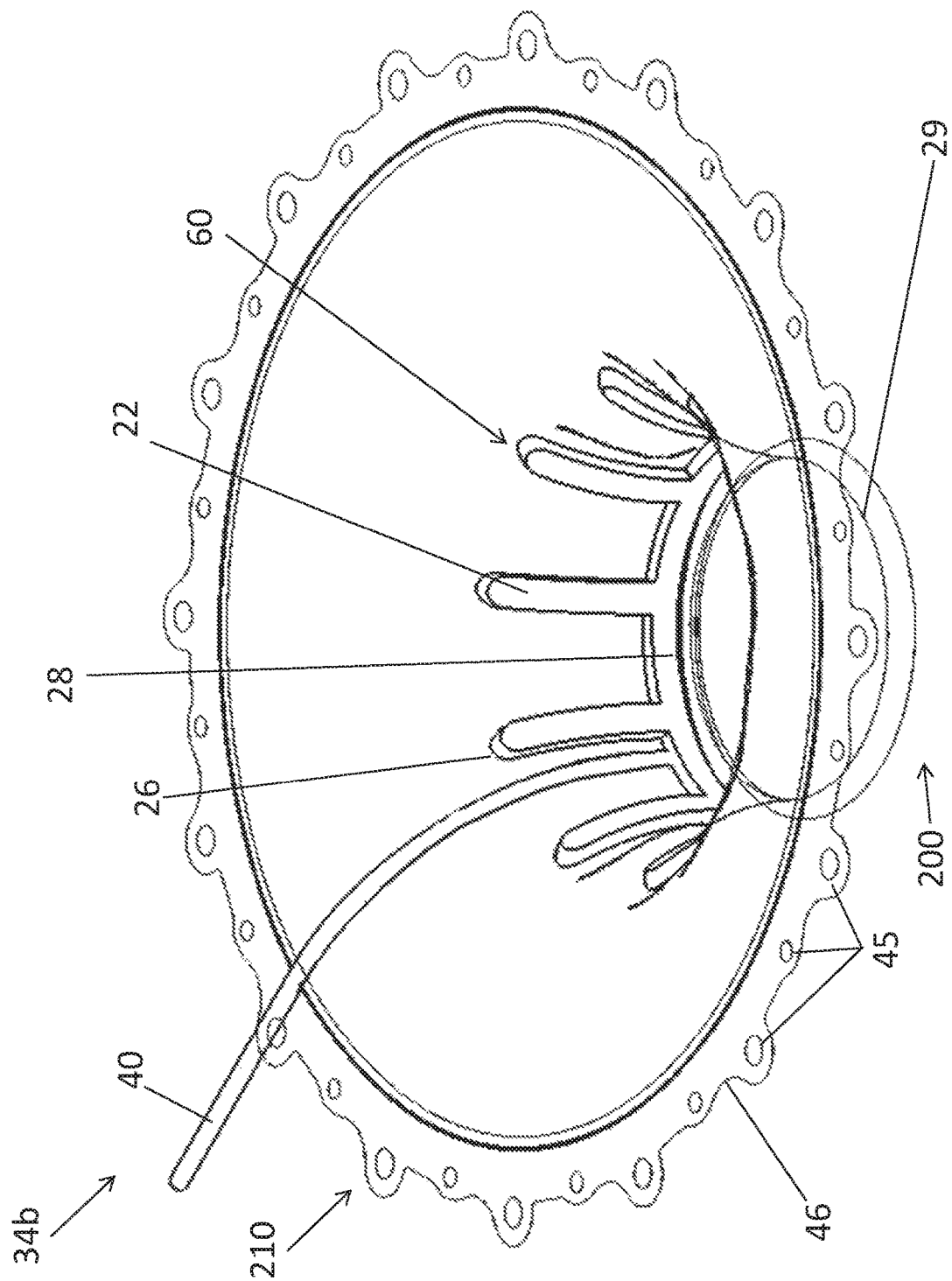
FIG. 9 shows an isometric view of the pliable membrane of FIG. 6 in its tubular form, in accordance with embodiments.

FIG. 7 shows an isometric view of the pliable membrane 34 in its planar configuration 34*a*. FIG. 8 shows a plan view of the pliable membrane 34 in its planar configuration 34*a*. FIG. 9 shows an isometric view of the pliable membrane 34 in its tubular configuration 34*b*. The pliable membrane 34 may be constructed on a flat plane as shown in FIGS. 6-8. If will be appreciated that the assembly described in FIGS. 7-8 can be constructed into a generally cylindrical or frustoconical assembly (as shown in FIG. 9) by pulling the superior end 210 of the pliable membrane 34 up and away from the inferior end 200 of the pliable membrane 34. Pulling the two ends 200, 210 away from each other may result in a generally cylindrical or frustoconical shape 34*b* as shown in FIG. 9. A resiliently deformable retention ring (for example first retention member 30 as described herein) may be sealed about the perimeter of the inferior end 200 of the structure as described herein. The pliable membrane 34 may be sealed to the deformable retention ring so as to form a trough 29 between the outer edge of the pliable membrane and the retention ring as described herein. The trough 29 may be formed by welding the pliable membrane 34 onto the bottom or outer perimeter of the deformable retention ring and wrapping the pliable membrane 34 around and inside the ring. The deformable retention ring may be sufficiently strong and/or biased towards a particular configuration so as to resist inversion when tension is applied to the pliable membrane 34.

The pliable membrane assembly 34 may include several integrated features including a scalloped edge or perimeter 46 on its superior end 210 with holes 45 disposed adjacent the edge 46, a fluid delivery region 60, and/or fluid delivery member 40. In some instances, a tubing pathway (not shown) may be provided within the pliable membrane 34 in order to guide a fluid removal member (for example fluid removal member 42 described herein) to the inferior retention member (for example inferior retention member 30 described herein).

Holes 45 may optionally be reinforced by a reinforcement layer (for example reinforcement layer 27 shown in FIG. 6) of the pliable membrane 34 in order to prevent the holes 45 from tearing when tension is applied to the pliable membrane 34 by the expandable retention member.

The pliable membrane 34 may be constructed as a single planar piece in order to avoid having to connect edges together in order to form the desired tubular (e.g. conical or frustoconical) shape. By constructing the pliable membrane 36 without folding or sealing the edges together, the pliable membrane 34 may provide a continuous fluid delivery region 60 which is uninterrupted by welding or sealing and thus has less resistance to fluid flow therein.

The fluid delivery region 60 may be defined by the enclosed space created between the outer layer 25 and the inner layer 21 when these components are sealed around the foam manifold 22. The foam manifold 22 may help to maintain the patency of the fluid delivery region 60 during fluid delivery to the tissue. In some instances, the fluid delivery region 60 may not comprise the foam manifold 22 and may instead simply be the enclosed space between the outer layer 25 and the inner layer 21. The fluid delivery region 60 may be fluidly coupled to an external pressure source via a fluid delivery member 40. Perforations in the fluid delivery region 60 may provide fluid communication between the external fluid source and the surgical site via the space within the pliable membrane 34 defined by the fluid delivery region 60 as described herein. The perforations may be created in the outer layer 25 via laser-drilling, pin-rolling, microfracturing/microtearing, or other suitable processes which will be known to one of ordinary skill in the art.

The location of the fluid delivery region 60 may be selected to as to optimize fluid delivery to the surgical site. If placed too low (e.g. towards the bottom ring of the surgical device described herein), the fluid may be delivered intra-abdominally. If placed too high, the fluid may undesirably be delivered to the skin surface. The fluid delivery region 60 may, for example, be approximately 1"-2" in width and disposed in a location 104 within about 4" of the bottom ring of the device, for example about 1¼" above the bottom ring. It will be understood by one of ordinary skill in the art that the fluid delivery region 60 may be positioned within the pliable membrane 34 at a desired location depending on patient body habitus and intended incision size.

The geometry design of the foam manifold may be balanced. The foam manifold 22 may, for example, have a "sunburst" pattern with a continuous base region 28 and fingers or rays 26 extending superiorly therefrom, for example as shown in FIG. 8. The fingers 26 may comprise one or more perforations in the pliable membrane 34 to facilitate fluid delivery to the tissue. In order to balance the level of fluid delivery provided at each location along the perimeter of the pliable membrane 34, it may be desirable to balance or equalize the fluidic resistance between the fluid delivery connection and each point of fluid egress (for example each perforation) along the perimeter of the pliable membrane 34. As fluidic resistance is proportional to conduit length, this can be accomplished by choosing the position of fingers 26 such that the fluidic resistance, R, is minimized for all points along the perimeter of the pliable membrane 34 and the difference between the maximum R ($R_{max}$) and minimum R ($R_{min}$) along the perimeter of the pliable membrane 34 is also minimized, with:

$$\frac{1}{R} = k \left[ \frac{1}{L_1} + \frac{1}{L_2} + \frac{1}{L_3} \cdots \frac{1}{L_n} \right]$$

where k is a constant that depends on the geometry and material composition of the foam manifold 22 and $L_1$, $L_2$, $L_3$, . . . , $L_n$ are the lengths of each the individual paths connecting the fluid delivery connection to a particular point along the fluid delivery region (for example perforation 36). Minimizing the variable resistance between path lengths to the perforations 36 disposed on fingers 26 may help to provide the wound with more even fluid pressure and delivery along its margins as described herein.

Figure 10:
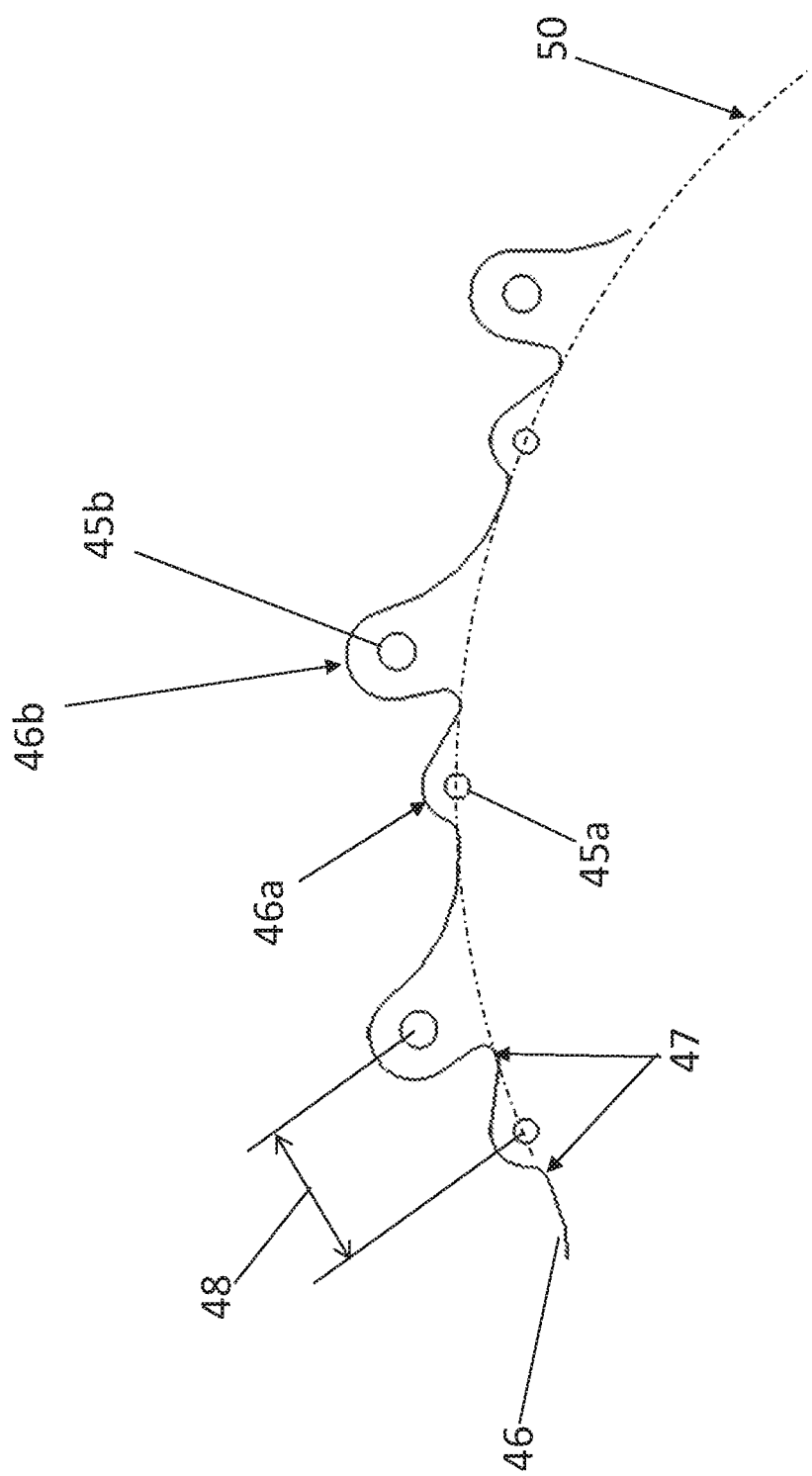
FIG. 10 shows a plan view of the upper edge of the pliable membrane of FIG. 6 highlighting the connector hole geometry, in accordance with embodiments.
Figure 14:
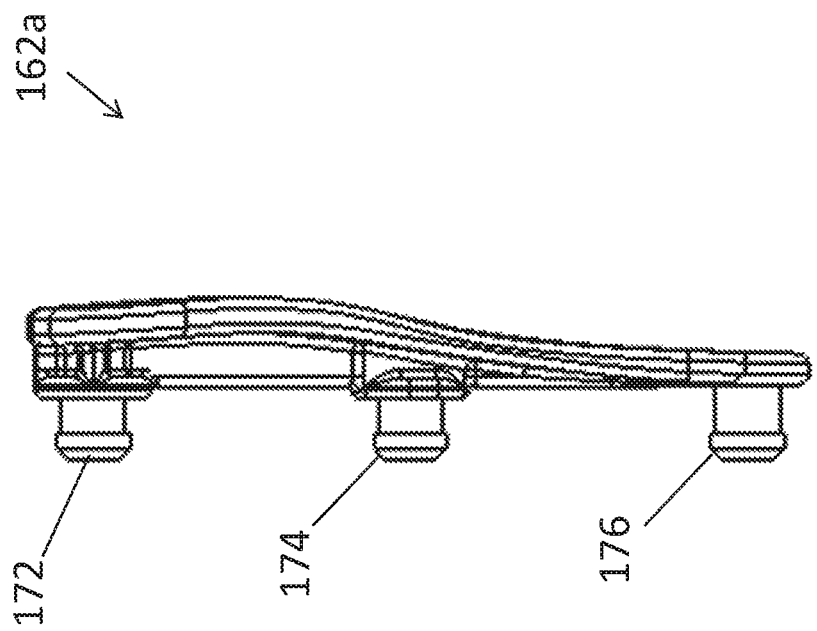
FIG. 14 shows a side view of the linkage of FIG. 13, in accordance with embodiments.
Figure 13:
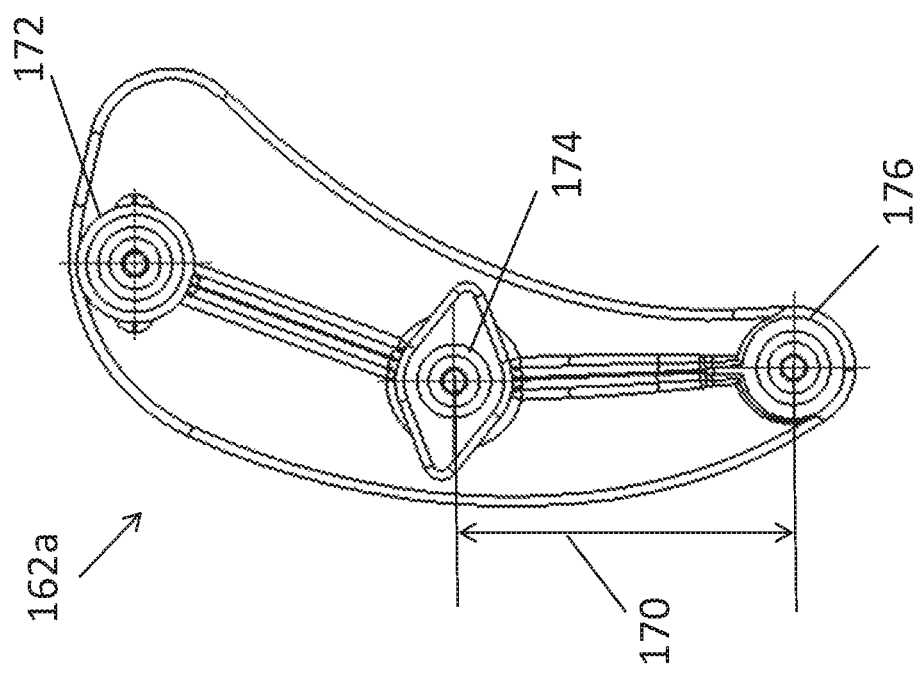
FIG. 13 shows a plan bottom view of an exemplary linkage, in accordance with embodiments.

FIG. 10 shows a plan view of the upper edge 46 of the pliable membrane 34 highlighting the connector hole 45 geometry. The pliable membrane 34 may comprise a plurality of holes 45 near the superior (upper) perimeter 46 of the pliable membrane 34. The holes 45 may be sized to be assembled around post features incorporated into the links comprising the retraction ring design described herein. The holes 45 may be configured to engage innermost and middle posts (for example 174 and 176, respectively, as shown in FIGS. 13-14) of the top linkages to couple the pliable membrane 34 to the expanding linkage structure. The inner and middle posts may, for example, be sized and shaped to fit within the holes 45. The perimeter 46 may, for example, be made up of alternating inner loops 46*a* and outer loops 46*b* separated by valleys 47 and comprising inner holes 45*a* and outer holes 45*b*, respectively. For example, an inner hole 45*a* may be sized and shaped to engage the innermost post of a top linkage while outer hole 45*b* may be sized and shaped to engage the middle post of the top linkage. The bottom linkages may then be coupled to the posts of the top linkages in order to create pivots (for example pivot 162 as described herein) around the holes 45 of the pliable membrane. The distance 48 between an inner hole 45*a* and an adjacent outer hole 45*b* may be greater than or equal to a distance between an inner post and an middle post of a top linkage (for example distance 170 as shown in FIG. 13).

Alternatively or in combination, the bottom linkages may comprise one or more posts as described herein and the top linkages may be coupled to the posts of the bottom linkages to create pivots.

The perimeter 46 of the pliable membrane 34 may be scalloped (as shown), elliptical, triangular, rectangular, square, polygonal, or asymmetrical as desired or known to one of ordinary skill in the art. The pliable membrane 34 may be coupled to the expanding linkage structure described herein so as to avoid having or reduce the amount of pliable membrane 34 between the linkages which may impair movement of the expanding linkage structure. The scalloped edge 46 of the pliable membrane may be biased to one side (i.e. asymmetrical) such that the pliable membrane 34 folds and unfolds in a predictable manner when the expandable retention member is collapsed and expanded, respectively.

Attachment of the pliable membrane 34 at or near the inner perimeter of the expanding linkage structure may apply symmetric (i.e. uniform) or near symmetric tension to the pliable membrane 34. Uniform tension along the pliable membrane 34 may allow the pliable membrane 34 to symmetrically radially expand as the expanding linkage structure is symmetrically radially expanded. Symmetric radial expansion of the pliable membrane 34 may provide for uniform expansion of the wound.

The inner loops 46a may be disposed along an arc 50 comprising a radius. The radius of the inner loop arc 50 may be maximized in order to provide as much material as necessary in order to create the desired pleats and valleys 49 between the loops 46a, 46b. The radius of the inner loop arc 50 may be tangent to or below the inner loops 45a.

Figure 11:
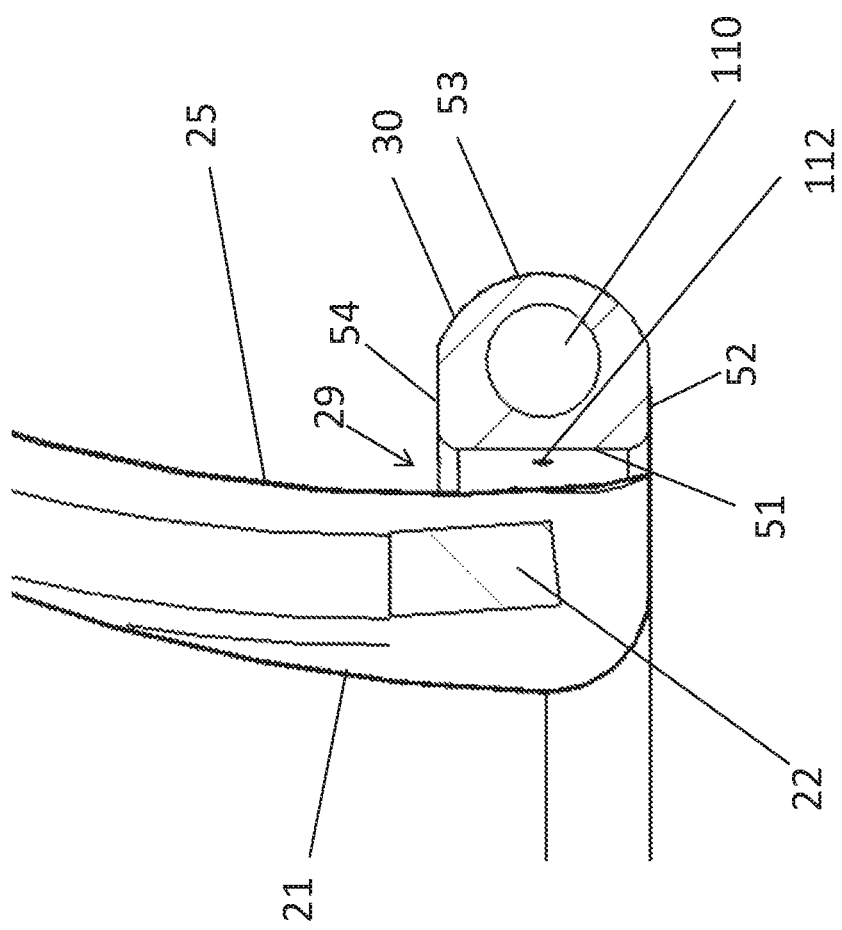
FIG. 11 shows a cross-sectional view of an exemplary inferior retention member with fluid removal ports and lumen, in accordance with embodiments.

FIG. 11 shows a cross-sectional view of an exemplary inferior retention member 30 with fluid removal ports 112 and lumen 110. The inferior retention member 30 may comprise a resiliently deformable retention member as described herein. The deformable ring 30 may be configured to be placed preferably intra-abdominally during use, and may have any number of sizes as desired by one of ordinary skill in the art. The deformable ring 30 may be sized to prevent the ring from popping out of the wound for example.

The inferior retention member 30 may be sealed about the perimeter of the inferior end of the pliable membrane 34 as described herein. The inferior retention member 30 may have a cross-section which is circular, elliptical, triangular, rectangular, square, polygonal, or asymmetrical. For example, the inferior retention member 30 may have a D-shaped cross-section as shown, with a flat inner surface 51, a flat bottom surface 52, a curved outer surface 53, and a flat top surface 54. The inner surface 51 may define an inner perimeter of the inferior retention member 30. The bottom surface 52 may define a bottom perimeter of the inferior retention member 30. The outer surface 53 may define an outer perimeter of the inferior retention member 30. The top surface 54 may define a top perimeter of the inferior retention member 30. The inferior end of the pliable membrane 34 may be sealed onto the inner perimeter, bottom perimeter, outer perimeter, or top perimeter of the inferior retention ring 30.

The inferior retention member 30 and the pliable membrane 34 may be attached so as to form a trough 29 therebetween. The trough 29 may be located between the outer layer 25 of the pliable membrane 34 and an inner circumference of the inferior retention member 30, for example an inner circumference defined by the flat inner edge of a D-shaped inferior retention member 30. The opening to the trough 29 may be located at or above the inferior retention member 30 in order to collect fluid therein and prevent fluid from flowing past the inferior retention member 30 and entering the surgical site/abdominal cavity. The inferior retention member 30 may be a hollow retention member comprising a lumen 110 running therethrough.

Holes 112 on the inner circumference of the retention member 30 may be in fluid communication with the lumen to facilitate fluid removal from the trough 29 (and thus from the surgical site) through the lumen 110 via connection to an external vacuum or suction source as described herein. Fluid removal from holes 112 may occur at a location above the base of the retention member 30.

The size and number of holes 112 may be jointly determined to achieve transmission of external vacuum or suction to each hole 112 around the entire inner circumference of inferior retention member 30. The external vacuum or suction source may provide a pressure differential across holes 112 between the lumen 110 of interior retention member 30 and the surgical site (which may be at ambient pressure). Due to the holes 112 having slightly different distances to the external vacuum or suction source based on where they are located on inferior retention member 30, the resistance of each hole 112 to flow due to this pressure differential is preferably high enough to ensure that each hole 112 experiences a sufficiently high pressure differential to facilitate fluid removal through that hole 112.

The inferior retention member 30 may comprise a number of holes 112 within a range of about 1 hole to about 20 holes, for example within a range of about 1 hole to about 10 holes. Holes 112 may be patterned around the inner circumference of the inferior retention member 30 such that the holes 112 are evenly spaced thereon. Alternately or in combination, the holes 112 may not be evenly spaced about the inner circumference of the inferior retention member 30.

The holes 112 may have a diameter within a range of about 0.005" to about 0.050", for example within a range of about 0.010" to about 0.035". The inferior retention member 30 may comprise a plurality of holes 112 which have the same diameter. Alternatively or in combination, the inferior retention member 30 may comprise a plurality of holes 112 with different diameters.

In an exemplary embodiment, the inferior retention member 30 may comprise a number of holes 112 within a range of about 1 to about 10 holes with hole diameters within a range of about 0.010" to about 0.035".

Figure 12:
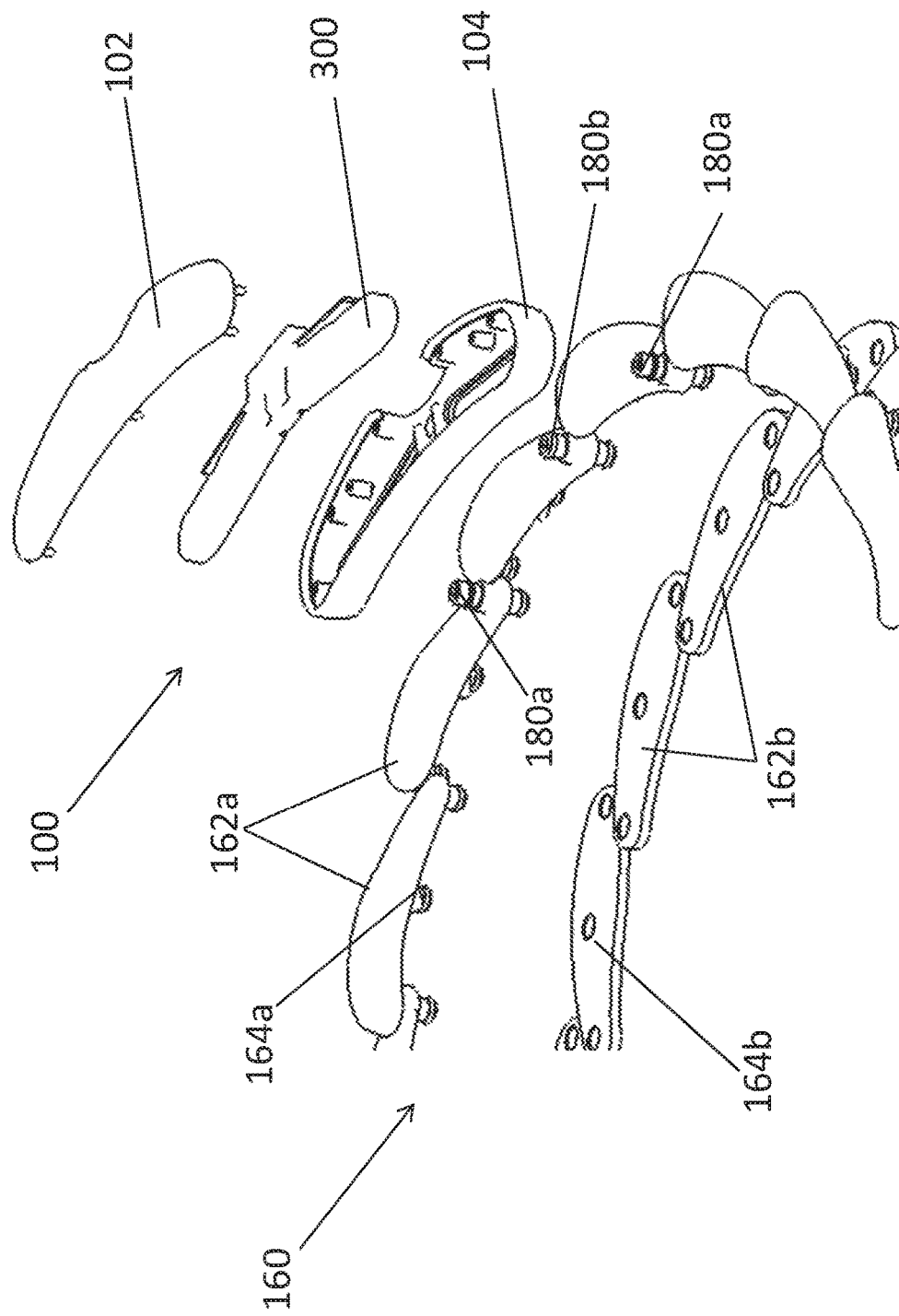
FIG. 12 shows an exploded view of an exemplary superior retention member and locking mechanism, in accordance with embodiments.

FIG. 12 shows an exploded view of an exemplary superior retention member 160 and locking mechanism 310. The expanding linkage structure 160 may comprise a plurality of interconnected linkages 162. The linkages 162 may, for example, comprise a plurality of top linkages 162a and a plurality of bottom linkages 162b. The linkages 162a, 162b may be coupled to one another other by pivots 164 formed by the insertion of posts 164a on the top linkages 162a into holes 164b in the bottom linkages 162b. The posts 164a and holes 164b forming pivots 164 may be removably coupled or attached so as to prevent disengagement. The post 164a and hole 164b are just one possible mechanism for generating a pivot 164. It will be understood by one of ordinary skill in the art that any number of mechanisms may be used to pivotably couple the top linkage 164a and bottom linkage 164b.

The linkages 162a, 162b may rotate about the pivots in order to radially expand or collapse the expanding linkage structure 160. The linkages 162a, 162b may be coupled to one another in order to mechanically couple rotation of the top linkage 162a with rotation of the bottom linkages 162b. As shown here, each top linkage 162a may be coupled to three bottom linkages 162b at pivots 164, and each bottom linkage 162b may be coupled to three top linkages 162a at pivots 164 in an overlapping scissor-like pattern. Rotation of the linkages 162a, 162b about the pivots 164 may radially expand the expanding linkage structure 160 through circumferentially outward movement of the linkages as described herein. Actuation of the linkages 162a, 162b may cause the linkages 162a, 162b to pivot relative to one another thereby radially expanding or collapsing the expanding linkage structure 160. Actuation of the linkages 162a, 162b may pivot radially outward in order to expand in a plane above the wound. Each of the linkages 162 may rotate with respect to each other such that all of the pivots 164 translate in the plane during expansion and collapse of the expandable retention member 160. Each of the pivots 164 may radially expand in the plane away from the central axis of the structure during expansion and radially collapse in the plane towards the central axis of the structure during collapse of the expandable retention member 160.

The expanding linkage structure 160 may comprise a locking mechanism 310, for example a locking plate 300 (as described in FIGS. 22-26), disposed within a handle 100. The handle may comprise a top 102 and a bottom 104 which may be shaped to hold the locking plate 300. The locking mechanism and handle may be attached to an attachment post 180b on a first top linkage 162a and to two locking mechanism engagement posts 180a on one or more top linkage 162a near (e.g. adjacent) the first top linkage 162a.

The expanding linkage structure 160 may comprise a plurality of linkages 162. The expanding linkage structure 160 may, for example, comprise at least three linkages 162. In some embodiments, the expanding linkage structure 160 may comprise at least four linkages 162. In some embodiments, the expanding linkage structure 160 may comprise at least ten linkages 162. In some embodiments, the expanding linkage structure 160 may comprise at least 32 linkages 162. In some embodiments, the expanding linkage structure 160 may comprise at least 40 linkages 162. It will be apparent to one of ordinary skill in the art that the expandable retention member 160 may comprise any number of linkages 162 as desired.

FIG. 13 shows a plan bottom view of an exemplary top linkage 162a. FIG. 14 shows a side view of the linkage 162a. The linkage 162a may comprise an outer post 172, a middle post 174 and an inner post 176 disposed on an underside thereof. The posts 172, 174, 176 may be coupled to correspondingly-shaped holes in bottom linkages as described herein in order to form pivots as described herein. The pliable membrane 34 may comprise a scalloped edge as shown in FIG. 10 with holes 45 configured to be coupled to the expanding linkage structure as the innermost and middle posts 174, 176 (and thus pivots) as described herein. The inner loop 46a may be captured around the inner post 176 and the outer loop 46b may be captured around the middle post 174 underneath the wing-like top linkage 162a. The inner post 176 and the middle post 174 may be disposed at a distance 170 away from each other. Distance 170 may be less than or equal to the distance between an inner hole and an adjacent outer hole of the pliable membrane (for example distance 48 as shown in FIG. 10).

Figure 15:
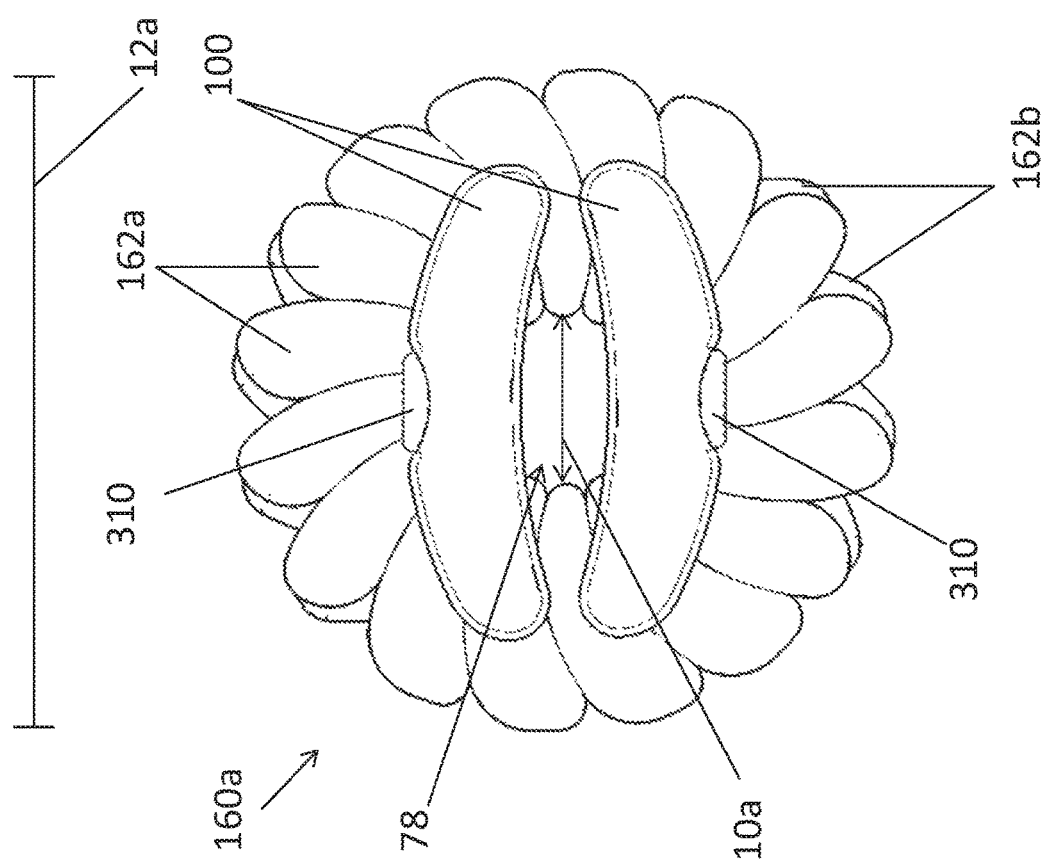
FIG. 15 shows a plan view of the superior retention member of FIG. 12 in a fully collapsed configuration, in accordance with embodiments.
Figure 16:
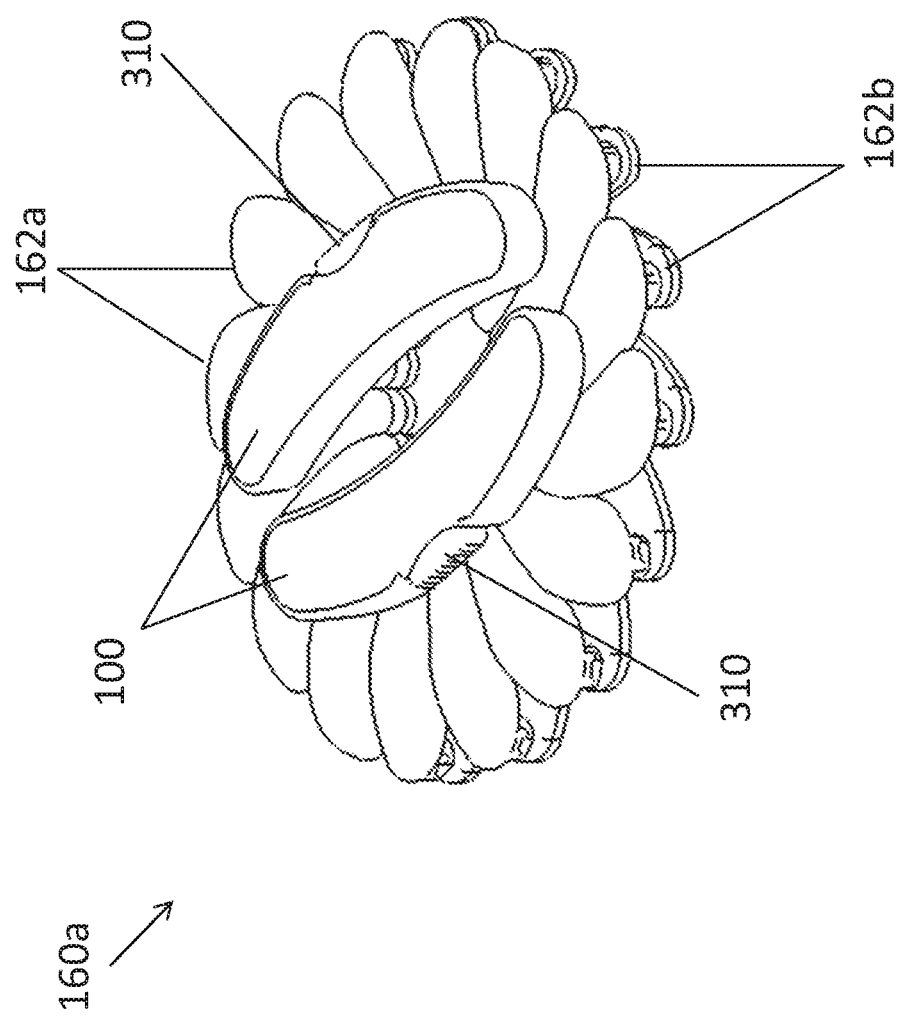
FIG. 16 shows an isometric top view of the superior retention member of FIG. 15, in accordance with embodiments.

FIG. 15 shows a plan view of the superior retention member 160 in a fully collapsed configuration 160a. FIG. 16 shows an isometric top view of the superior retention member 160 in a fully collapsed configuration 160a. FIGS. 17A-17B show isometric bottom views of the superior retention member 160 in a fully collapsed configuration 160a. The superior retention member 160 may comprise top linkages 162a coupled to bottom linkages 162b at pivots 164. The expanding linkage structure 160 may comprise locking mechanisms 310 disposed in handles 100 as described herein. Additionally, the inner pivots of the linkage structure 160 may comprise an inner profile 161 (as shown in FIG. 17B) defined by connecting the inner pivots, creating an equilateral geometric shape by using line segments or, alternatively, creating a circular shape by using a circle drawn through the center point of the inner pivots. In the fully collapsed configuration 160a, the distance across or the diameter of the inner profile 161a of the structure may be at a minimum distance 10a. The long edges of the top linkages 162a may be configured to contact or engage one another such that the top side of the expanding linkage structure 160 is substantially flat when in a collapsed configuration 160a.

The linkages 162a, 162b may rotate about the pivots 164 in order to radially expand or collapse the expanding linkage structure 160 as described herein. The linkages 162a, 162b may be coupled to one another in order to mechanically couple rotation of the top linkage 162a with rotation of the bottom linkages 162b. Rotation of the linkages 162a, 162b about the pivots 164 may expand the expanding linkage structure 160 through circumferentially outward movement of the linkages as described herein. The pivots 164 may expand at the same rate as one another. Actuation of the linkages 162a, 162b may cause the linkages 162a, 162b to pivot relative to one another thereby radially expanding or collapsing the expanding linkage structure 160. Each of the linkages 162 may rotate with respect to each other such that all of the pivots 164 translate in the plane during expansion and collapse of the expandable retention member 160.

The expanding linkage structure 160 may comprise an inner perimeter (e.g. circumference) which defines the inner edges of the expanding linkage structure 160 and an outer perimeter (e.g. circumference) which defines the outer edges of the expanding linkage structure 160. The inner and outer perimeters (and/or profiles 161a, 161b) of the expanding linkage structure 160 may be circular, elliptical, triangular, rectangular, square, polygonal, or asymmetrical. The inner and outer perimeters (and/or profiles 161a, 161b) of the expanding linkage structure 160 may be relatively smooth (for example as shown in FIG. 19 where the outer perimeter is approximately circular).

The inner and outer perimeters (and/or profiles 161a, 161b) of the expanding linkage structure 160 may comprise one or more axes of symmetry with respect to the incision (that is, a line drawn around the inner or outer perimeter of the expanding linkage structure 160 may define a shape which is generally symmetrical along at least two axes). For example, the inner and outer perimeters (and/or profiles 161a, 161b) of a circular expanding linkage structure 160 may have a plurality of axes of symmetry with respect to the incision. The inner and outer perimeters (and/or profiles 161a, 161b) may be symmetric in at least a parallel and a perpendicular axis with respect to the incision. By providing multiple axes of symmetry with respect to the incision, the device may provide improved flexibility in positioning and use compared to retraction devices within a single access of symmetry. The device may, for example, be usable in multiple orientations with respect to the incision, in multiple surgical locations, and with multiple surgeon preferences.

Figure 19:
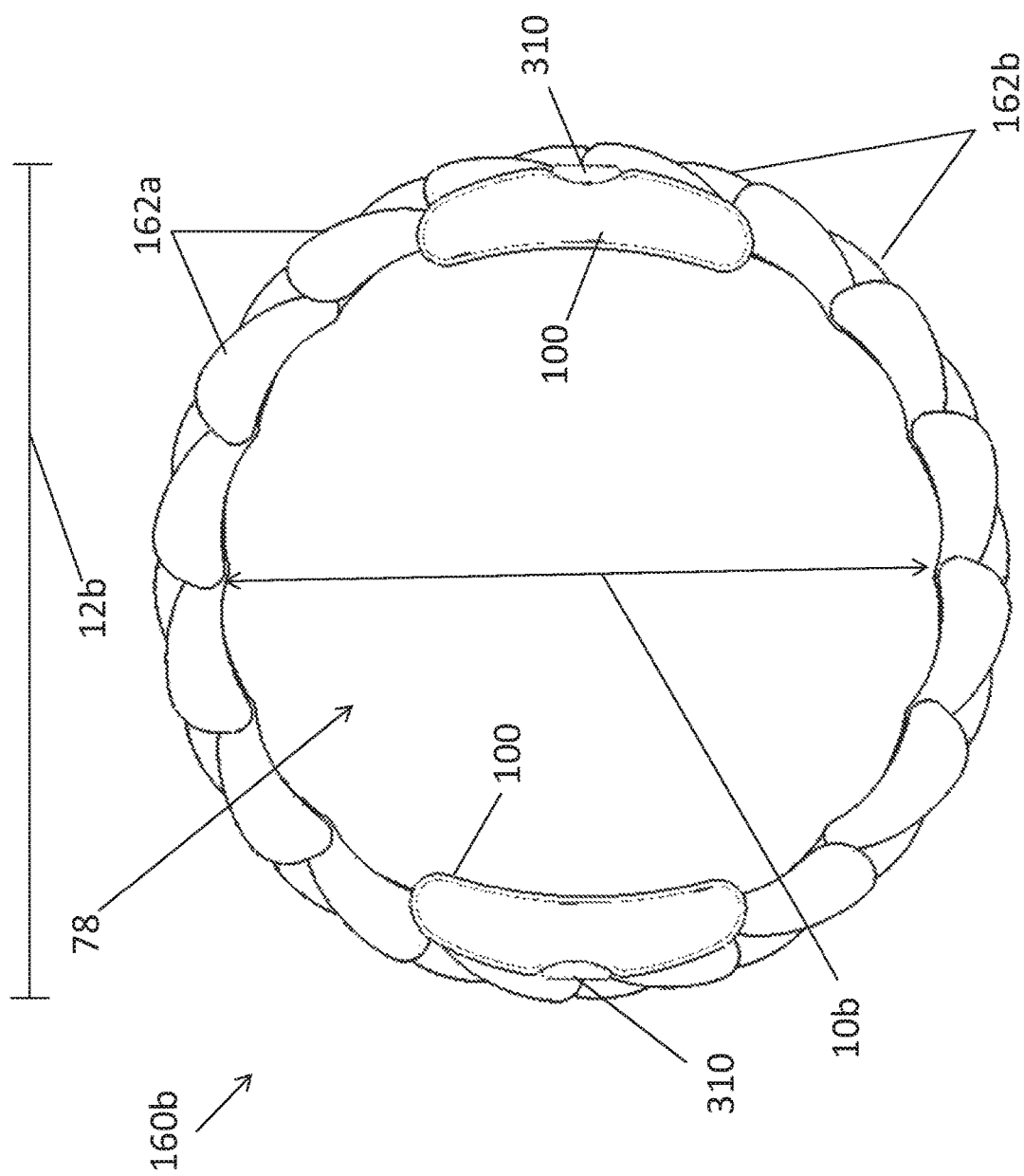
FIG. 19 shows a plan view of the superior retention member of FIG. 12 in a fully expanded configuration, in accordance with embodiments.

The inner perimeter or profile 161a may be expanded from a first collapsed maximum dimension (e.g. diameter or effective diameter) 10a or to a first expanded maximum dimension (e.g. distance 10b shown in FIG. 19). The first expanded maximum dimension may be greater than the first collapsed maximum dimension. The outer perimeter or profile 161b may be expanded from a second collapsed maximum dimension 12a to a second expanded maximum dimension (e.g. distance 12b shown in FIG. 19). The second expanded maximum dimension may be greater than the second collapsed maximum dimension. The expanding linkage structure 160 may be configured such that the maximum dimensions of the inner and outer perimeters or profiles 161a, 161b expand with a 1:1 ratio. The expanding linkage structure 160 may be configured such that the maximum dimensions of the inner and outer perimeters or profiles 161a, 161b expand with a ratio greater than 1:1. The expanding linkage structure 160 may be configured such that the maximum dimensions of the inner and outer perimeters or profiles 161a, 161b expand with a ratio less than 1:1. The linkages may be pivotably connected as described herein. Alternatively or in combination, one or more of the linkages may be slideably connected.

Figure 18:
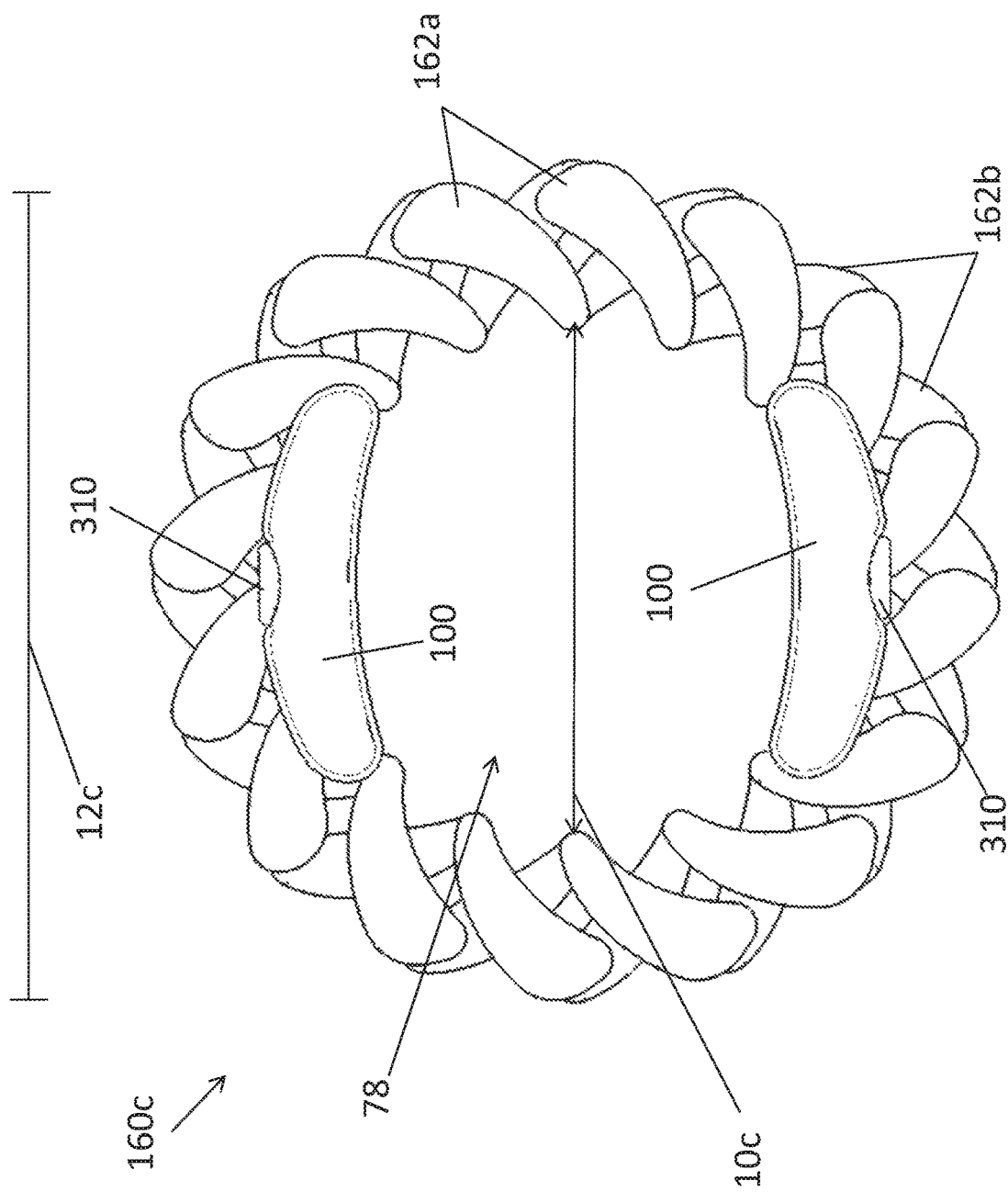
FIG. 18 shows a plan view of the superior retention member of FIG. 12 in an intermediate configuration, in accordance with embodiments.

FIG. 18 shows a plan view of the superior retention member 160 in an intermediate configuration 160c. The superior retention member 160 may comprise top linkages 162a coupled to bottom linkages 162b at pivots as described herein. The expanding linkage structure 160 may comprise locking mechanisms 310 disposed in handles 100 as described herein. After expansion to the intermediate configuration 160c, the long edges of the top linkages 162a may be out of contact with one another such that the top side of the expanding linkage structure 160 comprises gaps. In the intermediate configuration 160c, the inner profile may be at an intermediate length 10c. Intermediate length 10c may be greater than collapsed length 10a shown in FIG. 15 but less than expanded length 10b show in FIG. 19. In the intermediate configuration 160c, the outer profile of the structure 160 may have a dimension across 12c which is greater than the collapsed dimension 12a shown in FIG. 15 but less than the expanded dimension 12b shown in FIG. 19.

Due to the fact that the wound size will vary based on the procedure being performed, patient anatomy, and other factors, it could be beneficial for the structure 160 to be able to selectively maintain one of a plurality of unique intermediate states 160c defined by the effective inner diameter 10c. This plurality of intermediate states 160c may have any number of states such as between one and thirty unique states, two and twenty unique states, three and fifteen unique states, four and twelve unique states, five and ten unique states, or six and eight unique states. Additionally, it may be advantageous to have an infinite number of unique states 160c that can be selectively maintained.

Figure 20:
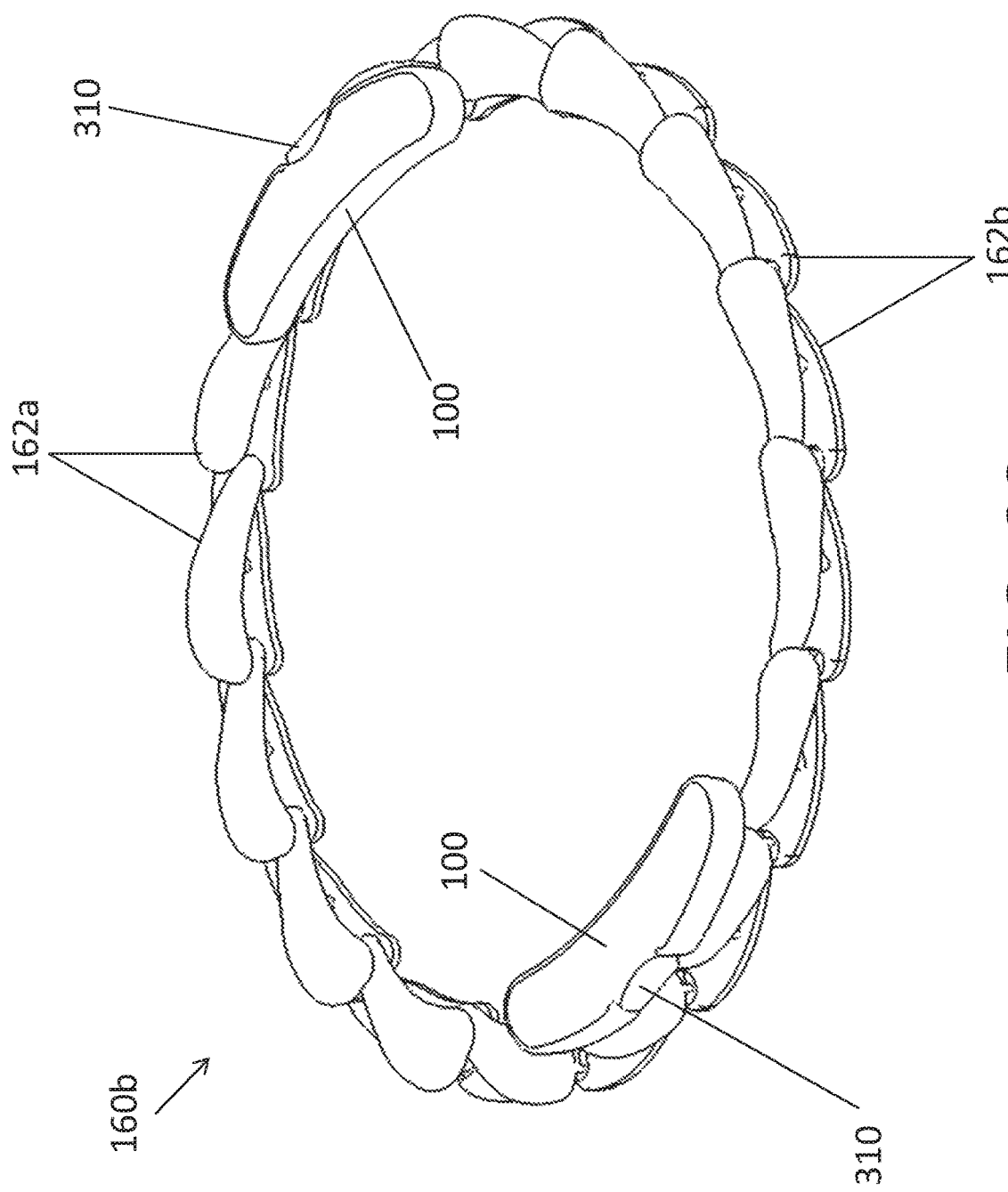
FIG. 20 shows an isometric top view of the superior retention member of FIG. 19, in accordance with embodiments.
Figure 21:
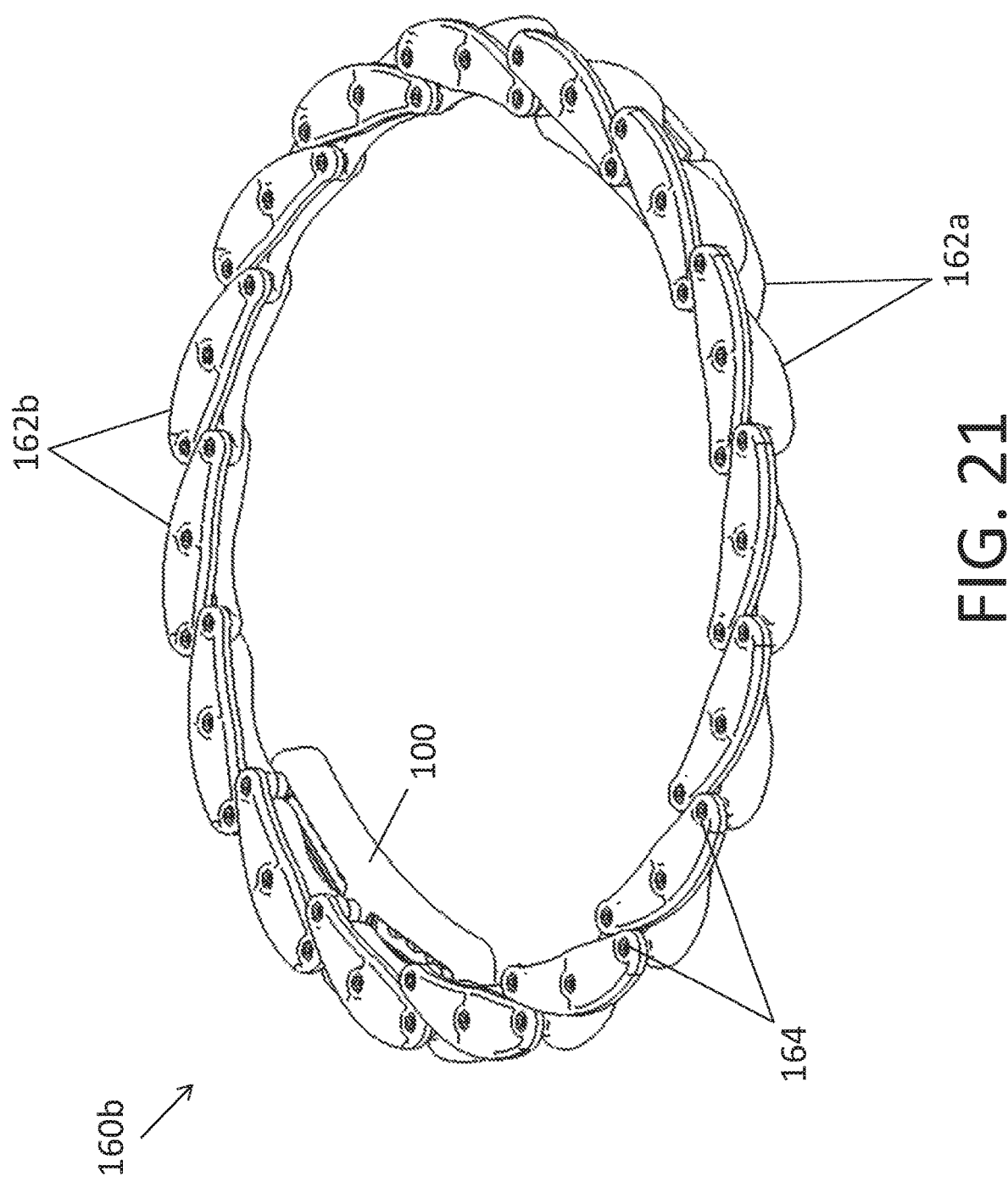
FIG. 21 shows an isometric bottom view of the superior retention member of FIG. 19, in accordance with embodiments.

FIG. 19 shows a plan view of the superior retention member 160 in a fully expanded configuration 160b. FIG. 20 shows an isometric top view of the superior retention member 160 in a fully expanded configuration 160b. FIG. 21 shows an isometric bottom view of the superior retention member 160 in a fully expanded configuration 160b. The superior retention member 160 may comprise top linkages 162a coupled to bottom linkages 162b at pivots 164. The expanding linkage structure 160 may comprise locking mechanisms 310 disposed in handles 100 as described herein. In the fully expanded configuration 160c, the inner profile may be at a maximum distance 10b (e.g. approximately the diameter of the central channel 78).

The top linkages 162a may be configured so as to overlap one another in the expanded configuration 160b in order to prevent sutures or other surgical implements from getting caught between the linkages when the second retention member 160 is expanded. The bottom linkages 162b may be configured to contact or engage one another in the expanded configuration 160b in order to prevent the pivots 164 from overlapping. The linkages 162 may be configured so as to have a minimum spacing between any two pivots in the fully expanded configuration 160b.

Not all of the expandable retention member 160 elements in FIGS. 12-21 are labeled in order to make the illustration less cluttered and easier to see. For example, not all of the pivots 164, which are represented by circles, are labeled. Some of the pivots 164 are hidden by linkages 162, 162a, 162b. Not all of the posts 164a and holes 164b which make up pivots 164 are labeled. Not all of the linkages 162, 162a, 162b are labeled.

In at least some instances, it could be advantageous to maintain a selected configuration of the expanding linkage structure 160. The device may, for example, be self-retaining. FIGS. 22-26 show a locking mechanism 310 comprising a locking plate 300 coupled to a handle backing 104 and the expanding linkage structure 160 which may be used to maintain an intermediate configuration and/or fully expanded configuration of the expanding linkage structure 160. FIGS. 27-32 show a locking mechanism 310 comprising a sliding bar mechanism 340 coupled to the expanding linkage structure 160 which may be used to maintain an infinite number of intermediate configurations and/or fully expanded configuration of the expanding linkage structure 160.

The distance between two posts may increase from a minimum distance in the collapsed state 160a to a maximum distance in the expanded state 160b. Additionally, the angle between two adjacent linkages may increase from a minimum angle in the collapsed state 160a to maximum angle in the expanded state 160b. This fact is also true for any two linkages whose relative angle changes as the expanding linkage structure 160 changes states—the angle will only increase or decrease from a collapsed state 160a to an expanded state 160b. Therefore, a mechanism (for example locking mechanism 310) to maintain a distance between any two points on different linkages or an angle between linkages of the retention ring 160 in an intermediate state 160c may be used.

Figure 22:
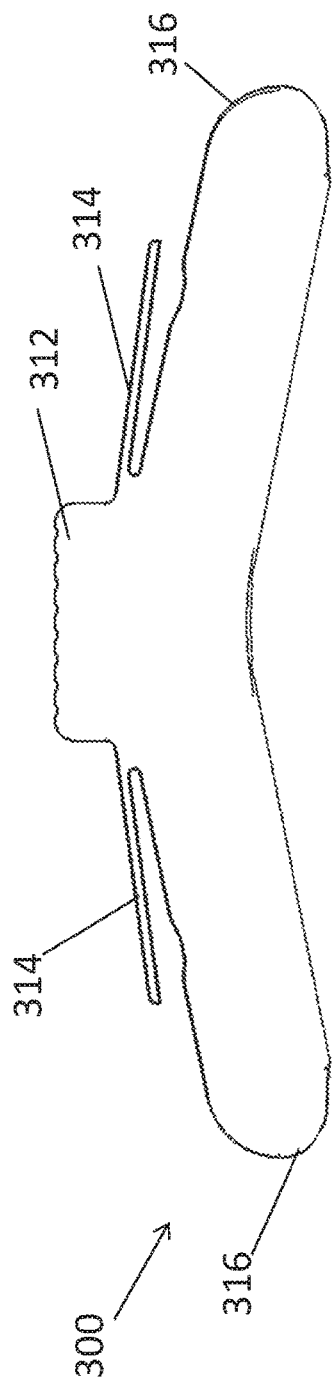
FIG. 22 shows a top plan view of an exemplary locking plate, in accordance with embodiments.
Figure 23:
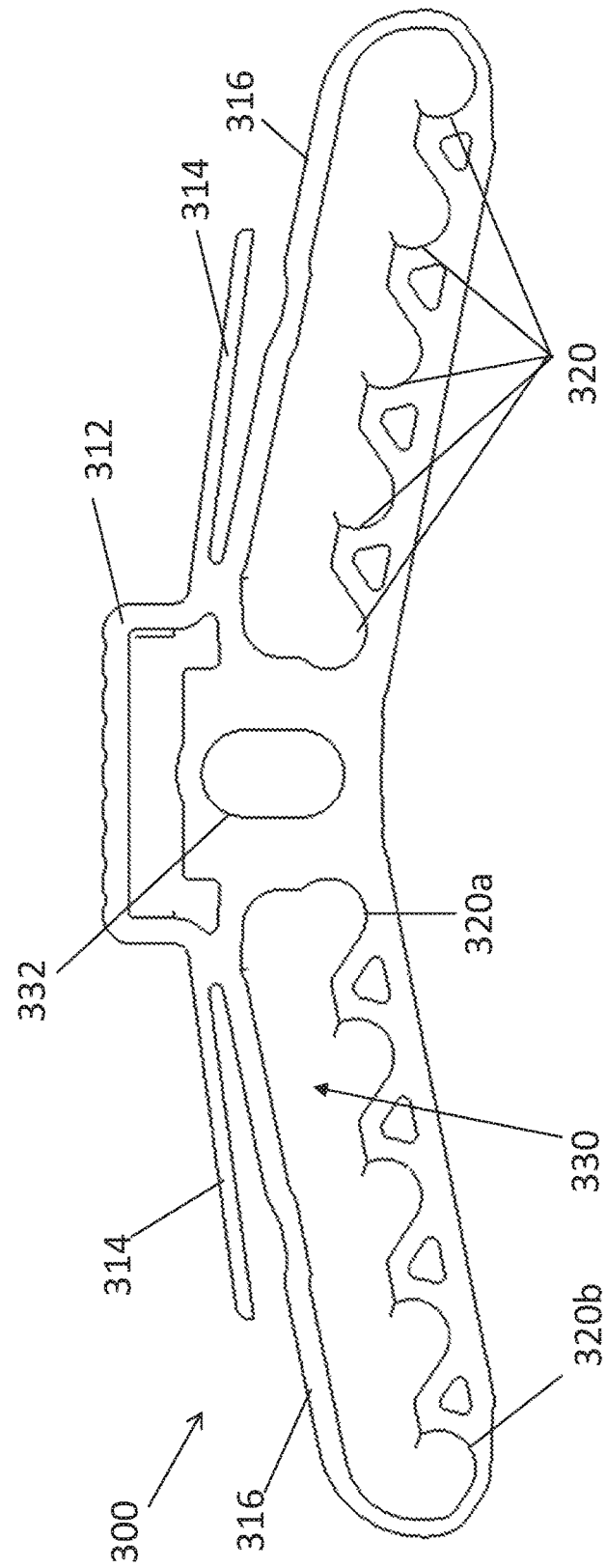
FIG. 23 shows bottom plan view of the locking plate of FIG. 22, in accordance with embodiments.

FIGS. 22 and 23 show an exemplary locking mechanism 310 comprising a locking plate 300. FIG. 22 shows a top plan view (as seen from a user's perspective) of the locking plate 300. FIG. 22 shows a bottom view (as seen from a user's perspective) of the locking plate 300. The locking plate 300 may be coupled to an expanding linkage structure and disposed within handle as described herein (for example as shown in FIG. 12).

The locking plate 300 may comprise a v-like shape with arms 316 extending away from a central region which is coupled to the handle backing and expandable retention member (for example via attachment post 180b as shown in FIGS. 12 and 24-26). Each arm 316 of the locking plate 300 may comprise one or more engagement features 320 configured to capture one or more engagement posts disposed on the expandable retention member (for example posts 180a as shown in FIGS. 12 and 24-26). The locking plate 300 may, for example, comprise at least two engagement features 320 per arm 316, an innermost engagement feature 320a and an outermost engagement feature 320b. The innermost engagement feature 320a may capture the engagement post of the expandable retention member 160 when the retention member 160 is in its fully collapsed configuration (for example collapsed configuration 160a shown in FIGS. 15-17B). The outermost engagement feature 320b may capture the engagement post of the expandable retention member 160 when the retention member 160 is in its fully expanded configuration (for example collapsed configuration 160b shown in FIGS. 19-21). In many embodiments, one or more additional engagement features 320 may be disposed between the innermost and outermost engagement features 320a, 320b in order to maintain the expandable retention member 160 in one or more intermediate expansion configurations (for example intermediate configuration 160c shown in FIG. 18). It will be understood by one of ordinary skill in the art that the locking plate 300 may comprise any number of engagement features 320 desired in order to secure the expanding linkage structure 160 in any number of intermediate configurations 160c. The locking plate 300 may further comprise a slot 330 in each arm through which an engagement post of the expandable retention member 160 may traverse as it expands or collapses.

The engagement features 320 may be shaped so as to prevent the engagement post from entering the slot 330 when a collapsing (i.e. radially inward) force is applied to the expandable retention member 160 and prevent collapse of the expandable retention member 160. A button or user interface 312 may be configured to allow the user to release the engagement post from the engagement feature 320 into slot 330, where it may then traverse freely while the button is pressed in order to collapse or expand the expandable retention member 160. A spring arm 314 may be provided on the locking plate 300 in order to bias the locking plate towards a locked position after the user has released the button 312.

The engagement features 320 may be shaped so as to allow the engagement post to enter the slot 330 when an expanding (i.e. radially outward) force is applied to the expandable retention member 160 to allow easy expansion of the expandable retention member 160, even when the button 312 is un-depressed.

Alternatively, the engagement features 320 may be shaped so as to prevent the engagement post from entering the slot 330 when an expanding (i.e. radially outward) force is applied to the expandable retention member 160 in order to prevent expansion of the expandable retention ring 160 without active engagement of the button 312 by the user.

Figure 24:
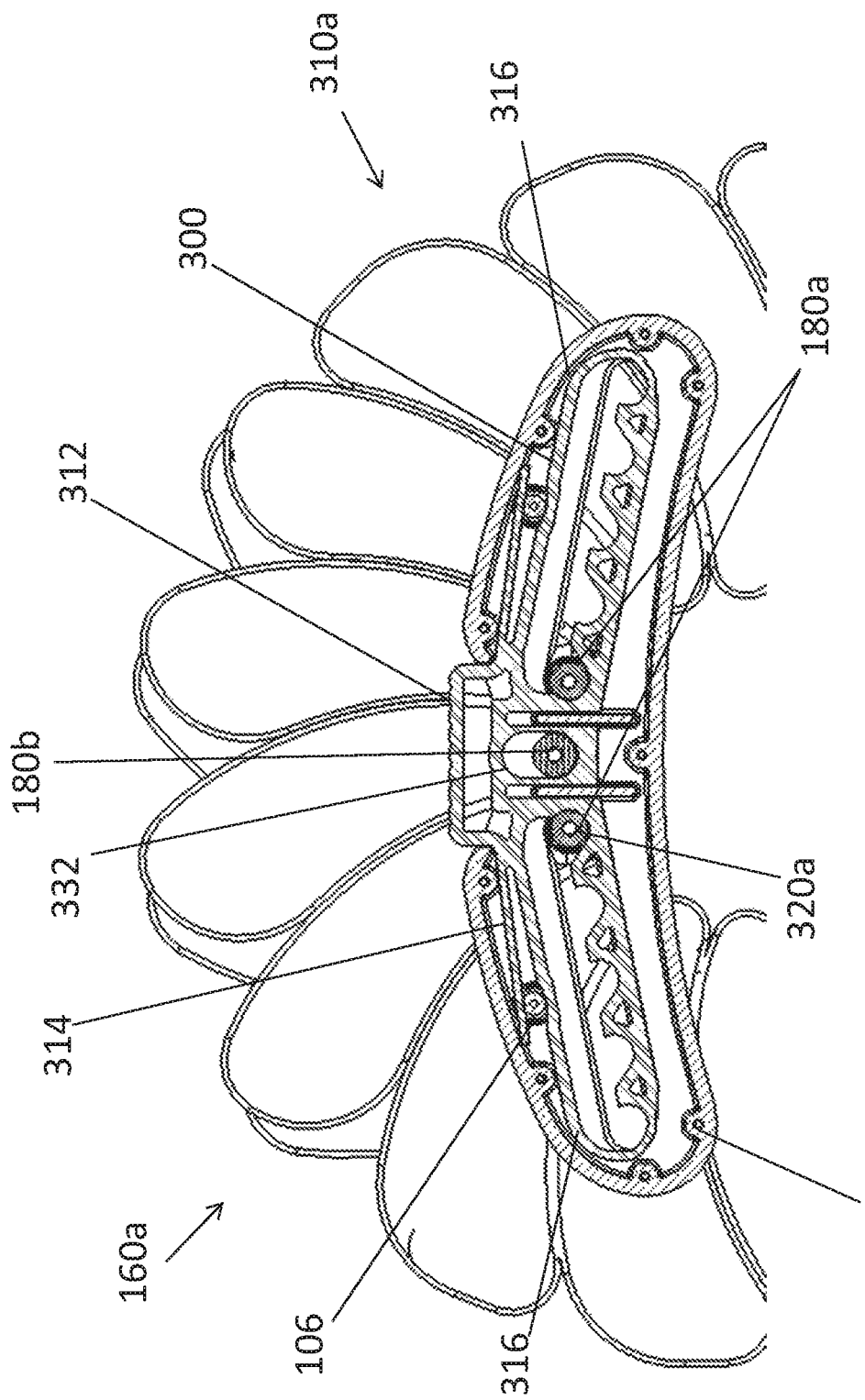
FIG. 24 shows a partial cross-sectional view of a locking mechanism comprising the locking plate of FIG. 22 coupled to an expandable superior retention member in its fully collapsed configuration, in accordance with embodiments.
Figure 25:
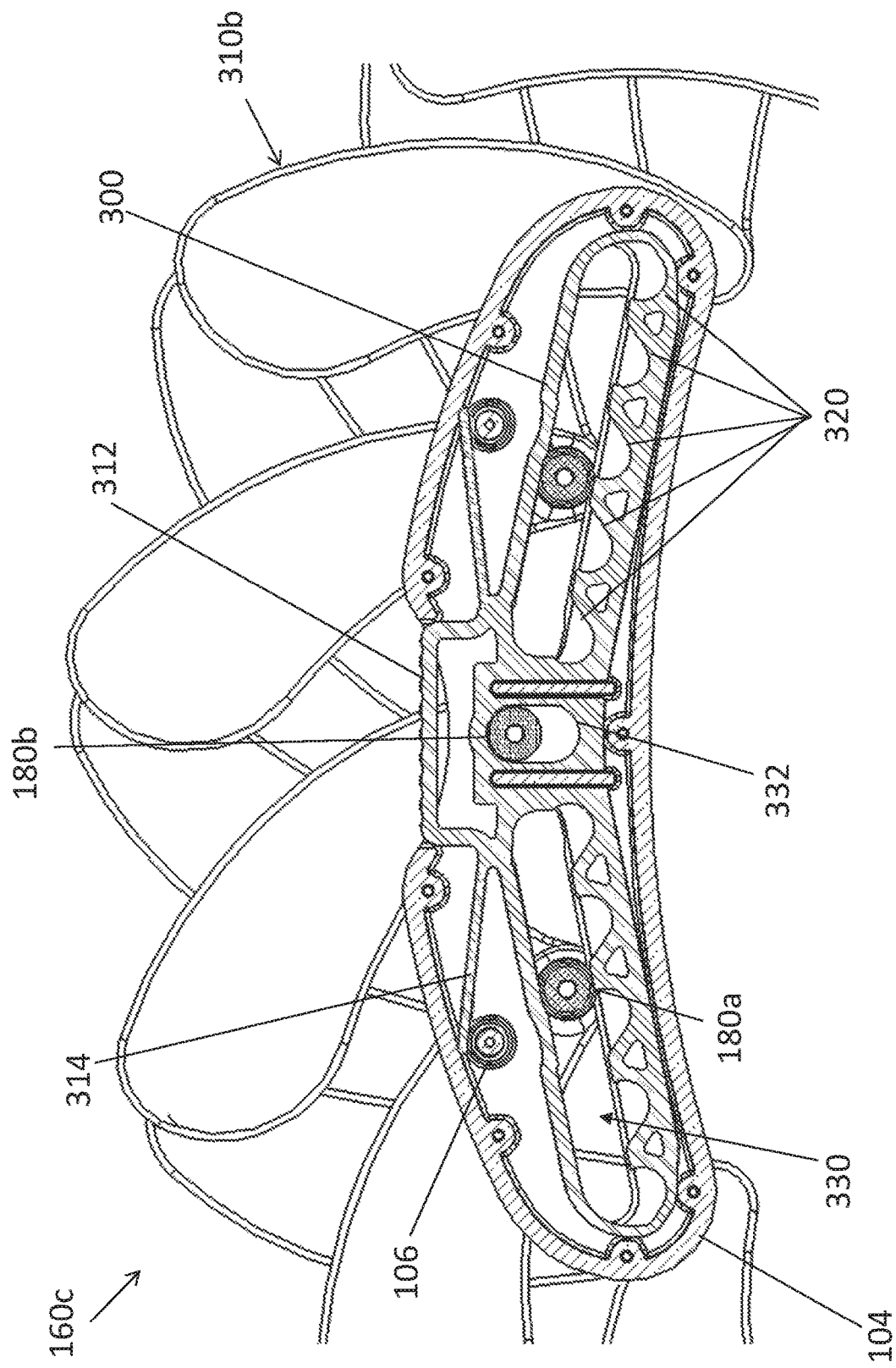
FIG. 25 shows a partial cross-sectional view of the locking mechanism of FIG. 24 with locking plate depressed to allow for expansion or collapse of the expandable superior retention member, in accordance with embodiments.
Figure 26:
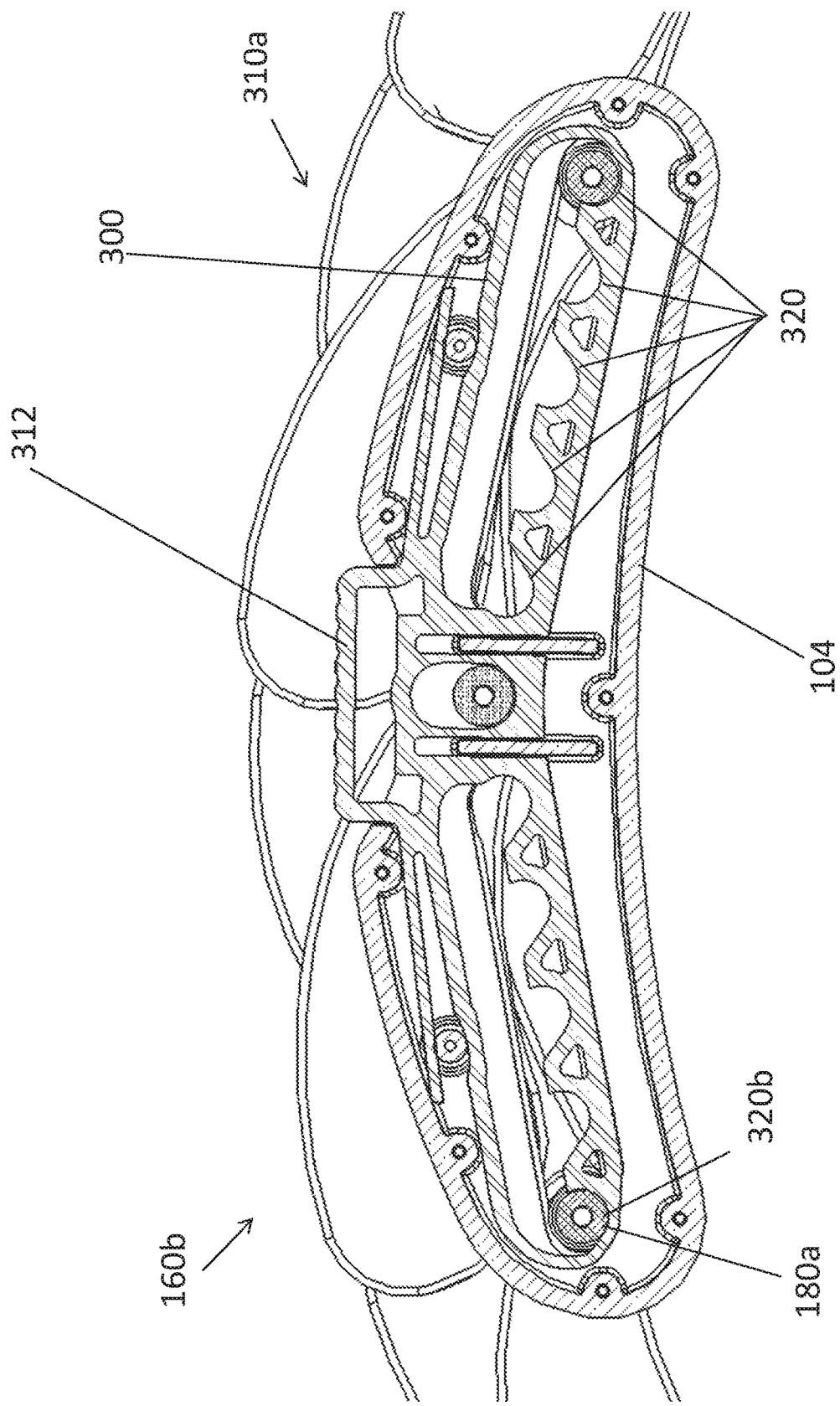
FIG. 26 shows a partial cross-sectional view of the locking mechanism of FIG. 24 with the expandable superior retention member in its fully expanded configuration, in accordance with embodiments.

FIGS. 24-26 show the locking mechanism 310 comprising a locking plate 300 coupled to the expandable superior retention member 160 in various states of collapse/expansion. Each of the linkages may rotate with respect to one another and all of the pivots may translate within a plane as described herein. By constraining at least one post coupled to a linkage, all linkages of the expandable retention member 160 may be constrained. The locking mechanism 300 may be disposed within the outer perimeter or outer profile of the expandable retention member, for example coupled to posts disposed along the inner perimeter or inner profile as shown.

The locking mechanism 310 may be coupled to one or more posts disposed on the top linkages of the expandable superior retention member 160 in order to selectively maintain a desired state of the expandable retention member 160 as described herein. The locking mechanism 310 may be coupled to one or more posts disposed along the inner edge of the top linkages, for example at one or more inner pivots. Alternatively or in combination, the locking mechanism 310 may be coupled to one or more posts disposed along the outer edge of the top linkages, for example at one or more outer pivots. Alternatively or in combination, the locking mechanism 310 may be coupled to one or more posts disposed between the inner and outer edges of the top linkages, for example at one or more middle pivots. The locking mechanism 310 may be coupled to any combination of inner, middle, or outer posts on adjacent or non-adjacent linkages, providing that the top linkages 162a are not coupled to a same bottom linkage 162b, as desired by one of ordinary skill in the art.

For example, the locking mechanism 310 may be coupled to one or more posts 180a, 180b disposed along the inner edge of the top linkages in order to selectively maintain a desired state of the expandable retention member 160 as described herein. By coupling the locking mechanism 310 to the inner edge, for example at one or more inner pivots, of the linkage structure 160 (instead of an outer or middle edge), the mechanism may effectively "pull" the linkage structure closed from the inside during collapse (instead of "pushing" as with an outer attachment point) which may prevent binding of the linkage structure 160 and/or pliable membrane attached thereto. Additionally, less force may be required to collapse the linkage structure 160 with the locking mechanism 310 coupled in such a configuration.

In some instances, one or more pivots or posts thereof may be configured to extend through and above the top linkages in order to facilitate coupling of the locking mechanism 310 to the expandable retention member 160. Alternatively or in combination, one or more additional posts or pins may be disposed on top of the linkages in order to facilitate coupling of the locking mechanism 310 to the expandable retention member 160.

FIG. 24 shows a partial cross-sectional view of a locking mechanism 310 comprising the locking plate 300 coupled to an expandable superior retention member 160 in its fully collapsed configuration 160a. Attachment post 180b on the expandable retention member 160 may be coupled to an attachment slot 332 in the locking plate 300 in order to secure the locking mechanism 310 to the expandable retention member 160. A spring arm capture post 106 on the handle backing 104 may be disposed between the spring arm 314 and the locking plate arm 316. In the fully collapsed configuration 160a, engagement posts 180a may be disposed in the innermost engagement features 320a on each arm 316 of the locking plate 300. The locking plate 300 is shown in an un-depressed or neutral configuration 310a which may allow unimpeded expansion of the expandable retention member 160 but prevent collapse of the expandable retention member 160.

The expandable retention member 160 may be made up of a plurality of linkages as described herein. The linkages may be pivotably coupled to one another such that each linkage is rotationally constrained by the linkages next to it as described herein. Engagement of any one of the linkages with the locking mechanism 310, for example by capturing post 180a in engagement feature 320, may prevent the links from rotating within respect to one another and therefore selectively maintain the desire expansion state. While this embodiment shows three adjacent linkages engaging the locking mechanism 310, it will be apparent to one of ordinary skill in the art that non-adjacent linkages may also be used.

FIG. 25 shows a partial cross-sectional view of the locking mechanism 310 with locking plate 300 depressed to allow for expansion or collapse of the expandable superior retention member 160. The expandable superior retention member 160 is shown in an intermediate configuration 160c. The locking plate 300 is shown in a depressed configuration 310b which may allow unimpeded expansion or collapsed of the expandable retention member 160. Engagement posts 180a are shown between engagement features traversing the slot 330. In the intermediate configuration 160c, engagement posts 180a may be disposed in engagement features 320 on each arm 316 which lie between the innermost and outermost engagement features 320a, 320b of the locking plate 300 described herein.

While the majority of the body of the locking plate 300 may be depressed (i.e. moved downward) within the handle, the spring arm 314 may remain coupled to the spring arm capture post 106 near the top of the handle. The spring arm 314 may be captured by the capture post 106 and deflected when the user pushes the rest of the locking plate 300 down using the button 312. Upon release of the button 312 by the user, energy stored in the spring arm 314 may cause the spring arm 314 to pull the body of the locking plate 300 back up to return to its un-depressed state. Return to the un-depressed state may also pull the locking plate 300 into engagement with the locking posts 180*a* in order to maintain the desired amount of retraction.

FIG. 26 shows a partial cross-sectional view of the locking mechanism 310 with the expandable superior retention member 160 in its fully expanded configuration 160*b*. The locking plate 300 is shown in the un-depressed or neutral configuration 310*a*. In the fully collapsed configuration 160*b*, engagement posts 180*a* may be disposed in the outermost engagement features 320*b* on each arm 316 of the locking plate 300.

FIGS. 27-32 show the locking mechanism 310 comprising a sliding bar mechanism 340 coupled to the expandable superior retention member 160 in various states of collapse/expansion. Each of the linkages may rotate with respect to one another and all of the pivots may translate within a plane as described herein. By constraining at least two posts coupled to two separate linkages, all linkages of the expandable retention member 160 may be constrained. The locking mechanism 340 may be disposed within the outer perimeter of the expandable retention member, for example coupled to posts disposed along the inner perimeter and the outer perimeter as shown.

The locking mechanism 310 may be coupled to one or more posts disposed on the top linkages of the expandable superior retention member 160 in order to selectively maintain a desired state of the expandable retention member 160 as described herein. The locking mechanism 310 may be coupled to one or more posts disposed along the inner edge of the top linkages, for example at one or more inner pivots. Alternatively or in combination, the locking mechanism 310 may be coupled to one or more posts disposed along the outer edge of the top linkages, for example at one or more outer pivots. Alternatively or in combination, the locking mechanism 310 may be coupled to one or more posts disposed between the inner and outer edges of the top linkages, for example at one or more middle pivots. The locking mechanism 310 may be coupled to any combination of inner, middle, or outer posts on adjacent or non-adjacent linkages, providing that the top linkages 162*a* are not coupled to a same bottom linkage 162*b*, as desired by one of ordinary skill in the art.

For example, the locking mechanism 310 may be coupled to one or more posts 180*b* disposed along the inner edge of a top linkage 162*a* and one or more posts 180*b* disposed along the outer edge of an adjacent or non-adjacent top linkage 162*a*, providing that the top linkages 162*a* are not coupled to a same bottom linkage 162*b*, in order to selectively maintain a desired state of the expandable retention member 160 as described herein.

In some instances, one or more pivots or posts thereof may be configured to extend through and above the top linkages in order to facilitate coupling of the locking mechanism 310 to the expandable retention member 160. Alternatively or in combination, one or more additional posts or pins may be disposed on top of the linkages in order to facilitate coupling of the locking mechanism 310 to the expandable retention member 160.

Figure 27:
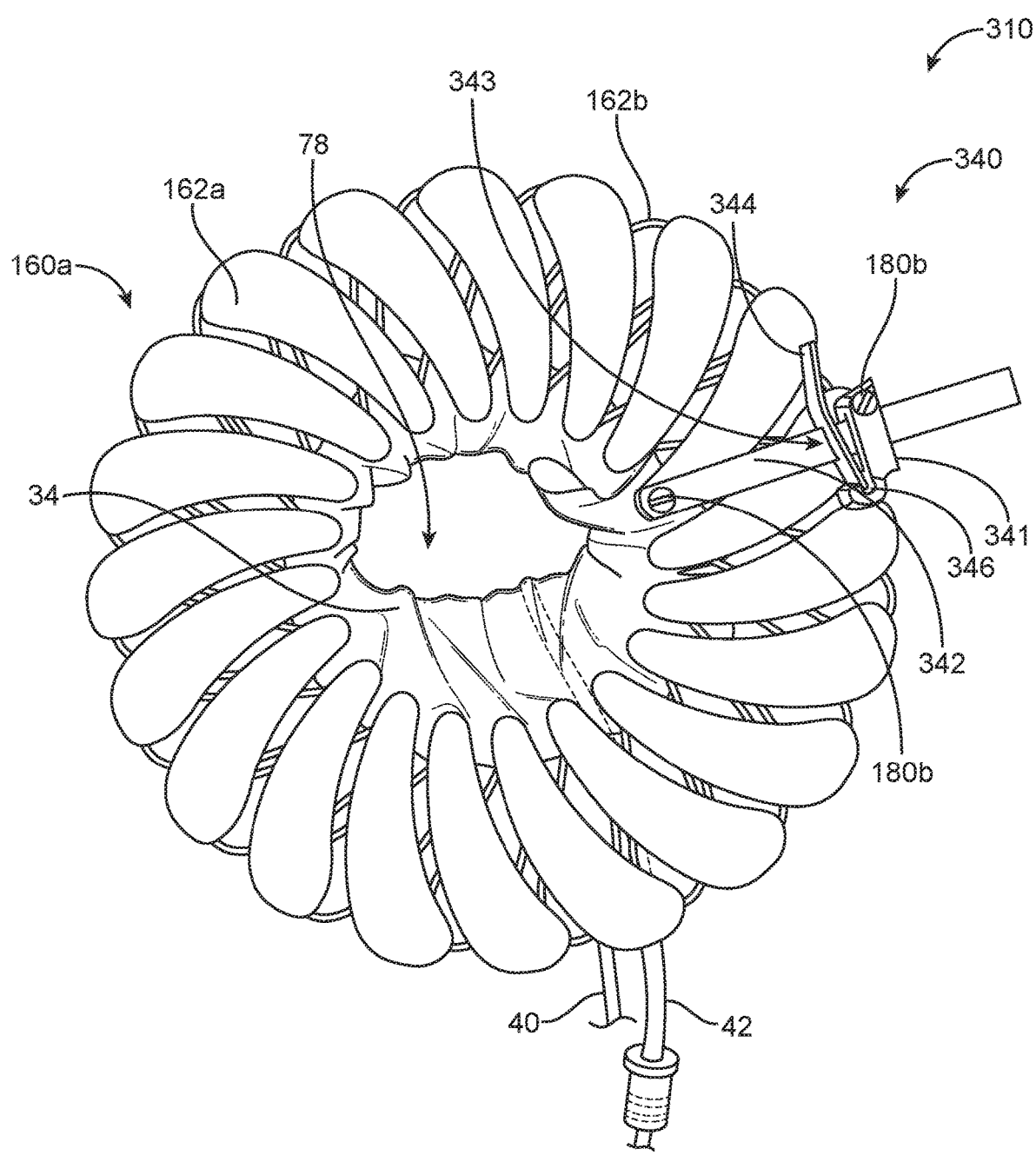
FIG. 27 shows a plan view of an exemplary locking mechanism comprising a sliding bar and coupled to an expandable superior retention member in it fully collapsed configuration, in accordance with embodiments.
Figure 28:
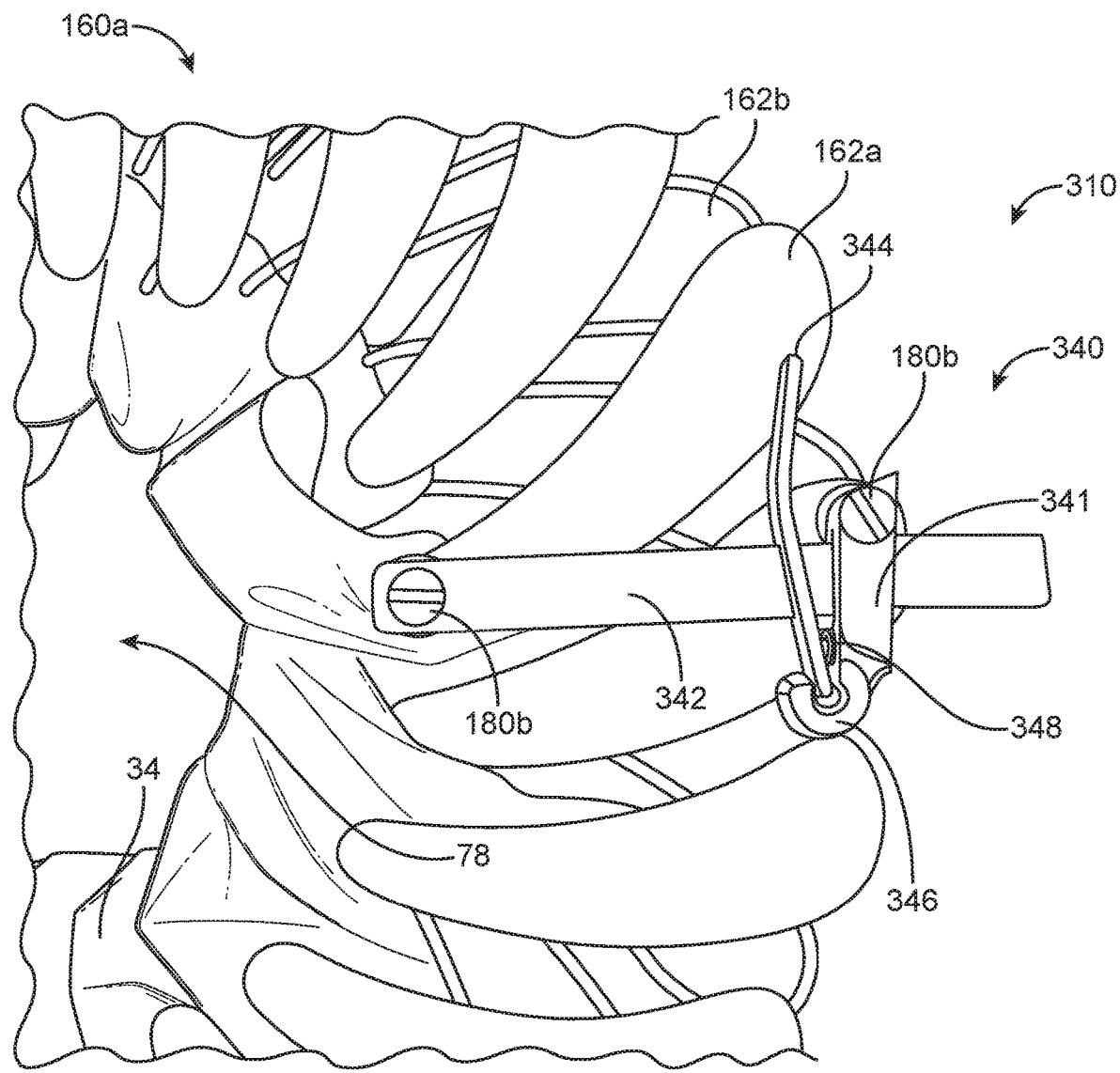
FIG. 28 shows an enlarged plan view of the locking mechanism of FIG. 27 with the expandable superior retention member in its fully collapsed configuration, in accordance with embodiments.

FIG. 27 shows a plan view of an exemplary locking mechanism 340 comprising a sliding bar 342 and coupled to an expandable superior retention member 160 in its fully collapsed configuration 160*a*. FIG. 28 shows an enlarged plan view of the locking mechanism of FIG. 27. The sliding bar locking mechanism 340 may be coupled to an expanding linkage structure 160 and disposed within a handle as described herein (for example as shown in FIG. 12). In the fully collapsed configuration 160*a*, the bar 342 may extend a minimum distance radially outward from the body 341 of the sliding bar locking mechanism 340.

The sliding bar locking mechanism 340 may comprise a bar 342 disposed within a window 343 of an arm 344. The sliding bar locking mechanism 340 may comprise one or more engagement features (not shown) configured to capture one or more engagement posts 180*b* disposed on the expandable retention member. The bar 342 may, for example, be coupled to an inner engagement post 180*b* and a body 341 of the mechanism 340 may be coupled to an outer engagement post 180*b*.

The arm 344 may be biased so as to prevent the bar 342 from sliding through the window 343 when a collapsing (i.e. radially inward) force is applied to the expandable retention member 160 and prevent collapse of the expandable retention member 160. A first end of the arm 344 may be pivotably coupled to the body 341 at a pivot point 346. A spring 348 may be disposed at or near the pivot point 346 in order to bias the arm 344 towards a locked position in which the arm 344 contacts and engages the bar 342 with an off-balance load to lock the bar 342 in place and prevent movement of the bar. The arm 344 may be configured to allow the user to release the bar 342 from the load of the arm 344 when compressed, which may remove the friction between the bar 342 and the arm 344, and the bar 342 may then traverse freely through the window 343 while the arm 344 is pressed in order to collapse or expand the expandable retention member 160. Upon release of the arm 344 by the user, energy stored in the spring 348 may cause the arm 344 to engage the bar 342 and lock it in place. Return to the un-depressed state may thus prevent the bar 342 from moving and maintain the desired amount of retraction. The arm 344 is shown in an un-depressed or neutral configuration which may allow unimpeded expansion of the expandable retention member 160 but prevent collapse of the expandable retention member 160.

In many instances, the arm 344 may be biased such that the expandable retention member 160 may be expanded without pressing on the arm 344. Alternatively, the arm 344 may be biased such that the expandable retention member 160 may only be opened if the arm 344 is pressed by the user.

Unlike the locking plate 300 shown in FIGS. 22-26, which feature discrete intermediate locking positions, the sliding bar locking mechanism 340 may be configured to lock the superior retention member 160 in an infinite number of intermediate configurations 160*c* between the collapsed configuration 160*a* and the expanded configuration 160*b*.

Figure 29:
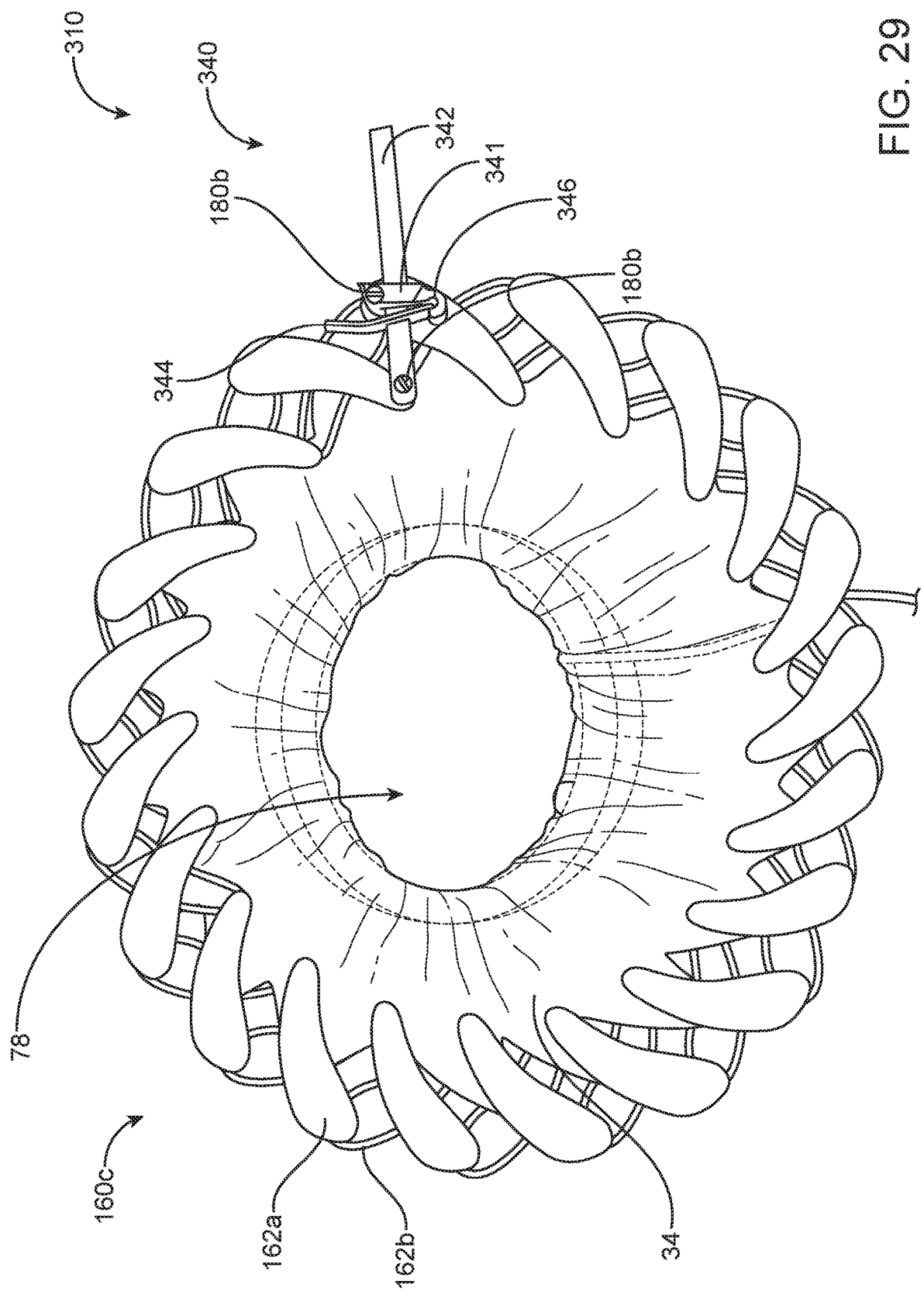
FIG. 29 shows a plan view of the locking mechanism of FIG. 27 with the expandable superior retention member in its intermediate configuration, in accordance with embodiments.
Figure 30:
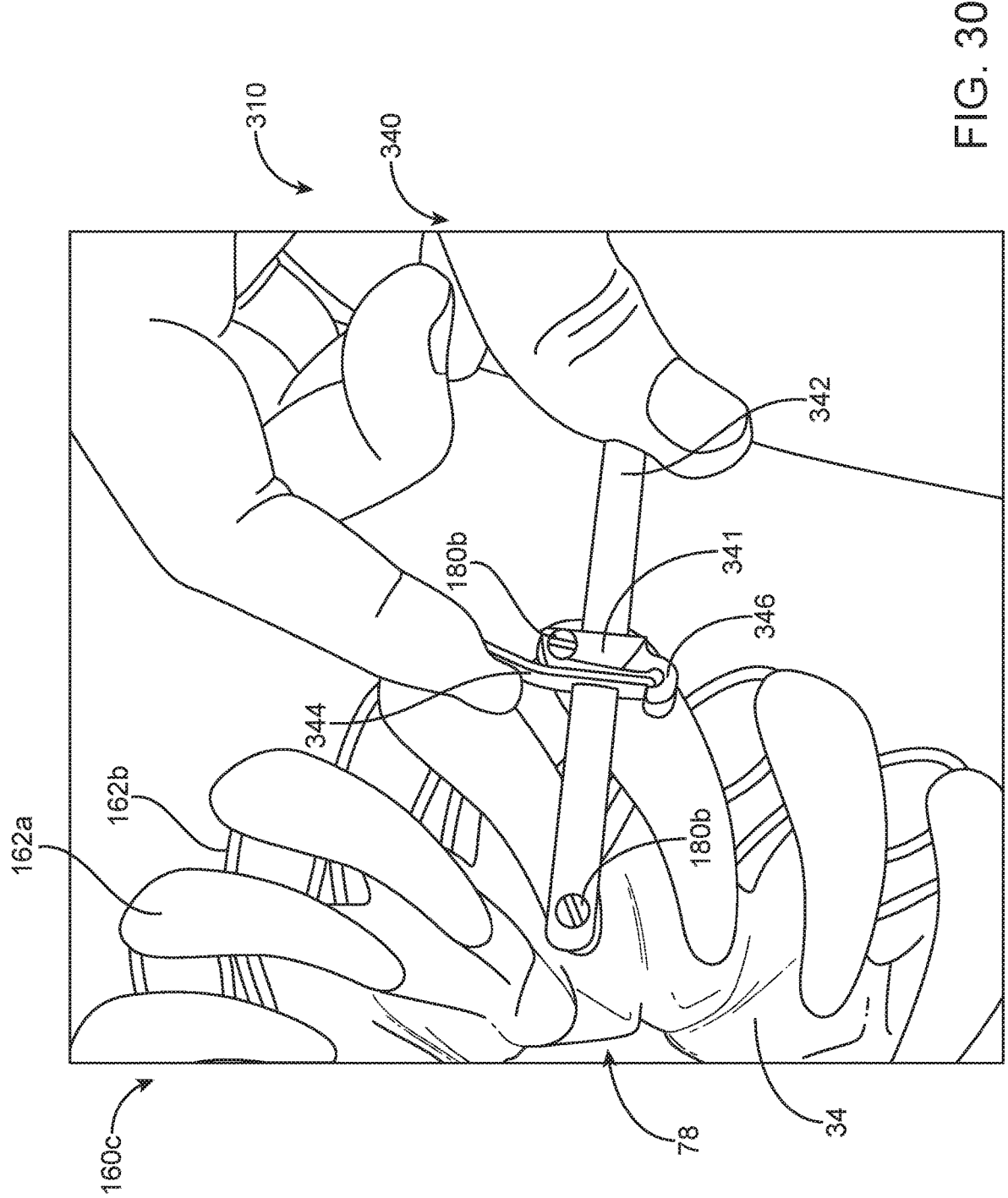
FIG. 30 shows an enlarged plan view of the locking mechanism of FIG. 27 with the expandable superior retention member in its intermediate configuration and the locking arm depressed to allow for expansion or collapse of the expandable superior retention member, in accordance with embodiments.

FIG. 29 shows a plan view of the locking mechanism 340 of FIG. 27 with the expandable superior retention member 160 in its intermediate configuration 160*c*. FIG. 30 shows an enlarged plan view of the locking mechanism 340 of FIG. 29 with the locking arm 344 depressed to allow for expansion or collapse of the expandable superior retention member 160. In the intermediate configuration 160*a*, the bar 342 may extend an intermediate distance radially outward from the body 341 of the sliding bar locking mechanism 340. The arm 344 is shown in a depressed configuration which may allow unimpeded expansion or collapsed of the expandable retention member 160.

The expandable retention member 160 may be made up of a plurality of linkages as described herein. The linkages may be pivotably coupled to one another such that each linkage is rotationally constrained by the linkages next to it as described herein. Engagement of any one of the linkages with the locking mechanism 310, for example by capturing post 180b by the bar 342 and/or body 341, may prevent the links from rotating within respect to one another and therefore selectively maintain the desire expansion state. While this embodiment shows two adjacent linkages engaging the locking mechanism 310, it will be apparent to one of ordinary skill in the art that non-adjacent linkages may also be used.

Figure 31:
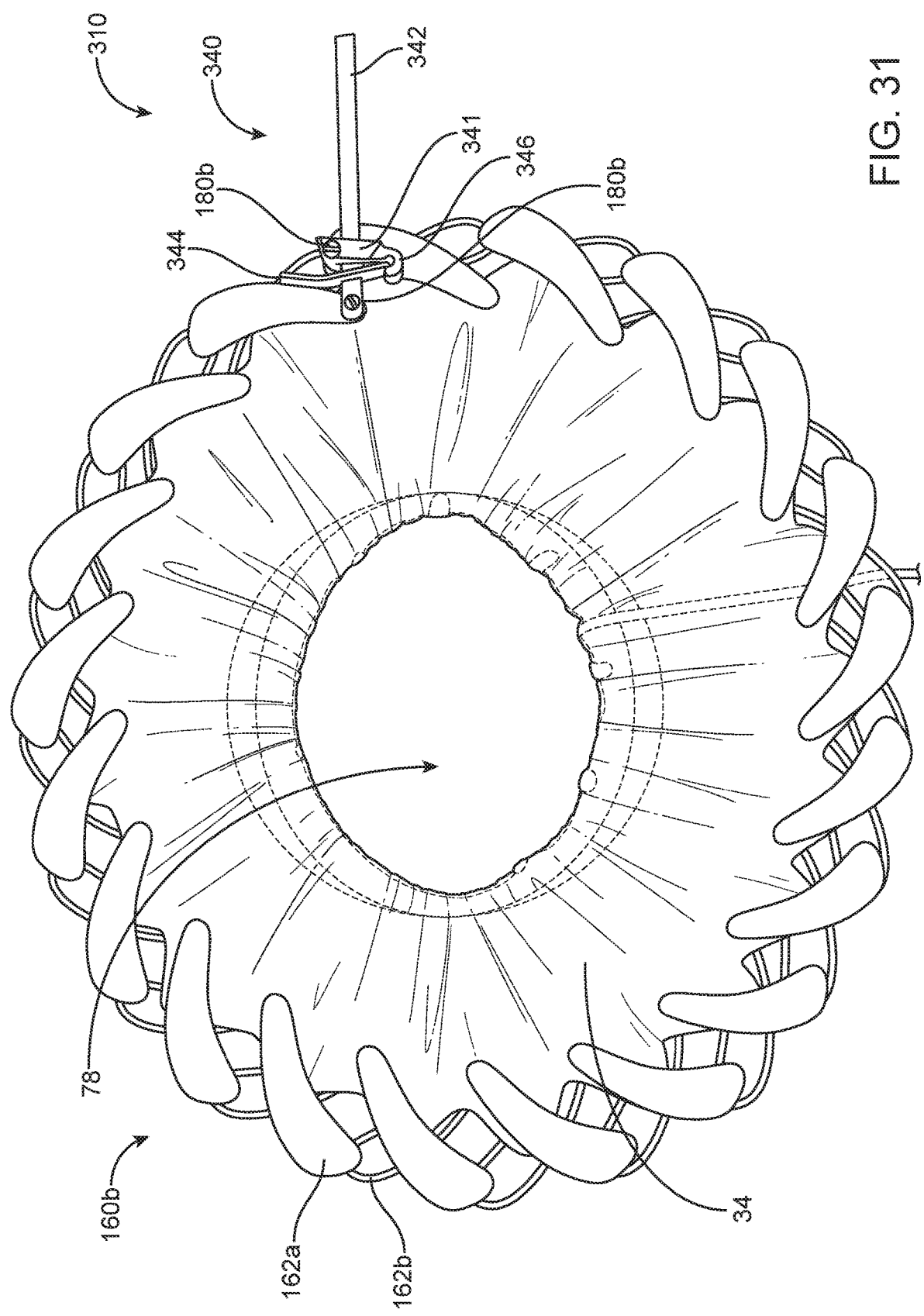
FIG. 31 shows a plan view of the locking mechanism of FIG. 27 with the expandable superior retention member in its fully expanded configuration, in accordance with embodiments.
Figure 32:
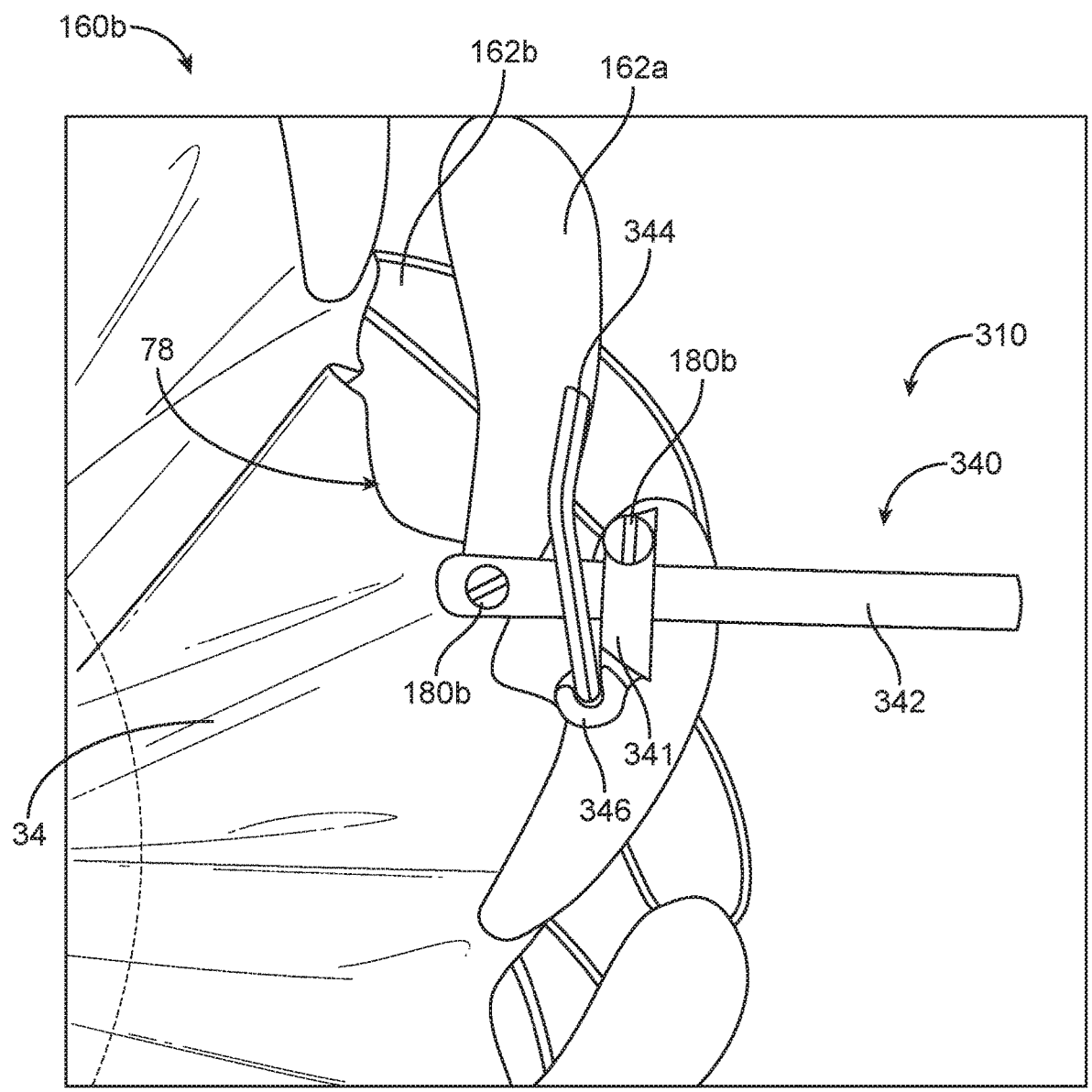
FIG. 32 shows an enlarged plan view of the locking mechanism of FIG. 27 with the expandable superior retention member in its fully expanded configuration, in accordance with embodiments.

FIG. 31 shows a plan view of the locking mechanism 340 of FIG. 27 with the expandable superior retention member 160 in its fully expanded configuration 160b. FIG. 32 shows an enlarged plan view of the locking mechanism 340 of FIG. 31. In the fully expanded configuration 160a, the bar 342 may extend a maximum distance radially outward from the body 341 of the sliding bar locking mechanism 340. The arm 344 is shown in an un-depressed or neutral configuration which may allow unimpeded expansion of the expandable retention member 160 but prevent collapse of the expandable retention member 160.

Additional details about the expanding linkage structure mechanisms and other locking mechanisms are disclosed in U.S. Pat. Nos. 9,402,612, 9,393,005, 9,084,594, 9,610,096, 9,788,823, 9,974,564, 10,085,735 and U.S. patent application Ser. Nos. 13/736,904, 15/957,381, and 16/121,484; the entire contents of which are incorporated herein by reference.

Additional details about the surgical device and how it may be used are disclosed in U.S. Pat. Nos. 9,393,005 9,084,594, 9,788,823, 10,085,735 and U.S. patent application Ser. Nos. 13/736,904, 15/344,407, and 16/121,484; the entire contents of which are incorporated herein by reference.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A surgical access system adapted to facilitate access to a surgical site within a body of a patient through an incision in the body, the surgical access system comprising:
   a first retention member configured for placement within the body at or near the surgical site;
   a second retention member configured for placement outside the body; and
   a pliable membrane extending between the first retention member and the second retention member, an inferior portion of the pliable membrane near the first retention member comprising a fluid delivery region in fluid communication with a fluid delivery member, wherein the fluid delivery region comprises at least one perforation therein to allow fluid introduced into the fluid delivery region via the fluid delivery member to exit the surgical access system,
   wherein the fluid delivery region comprises a continuous base near the first retention member and a plurality of fingers extending towards the second retention member.

2. The system of claim 1, wherein the second retention member lies in a plane above the incision and is configured to expand from a collapsed configuration to an expanded configuration in the plane.

3. The system of claim 1, wherein the fluid delivery region is positioned within the pliable membrane so as to prevent fluid from spilling out of the incision.

4. The system of claim 1, wherein the pliable membrane comprises an inner layer and an outer layer.

5. The system of claim 4, wherein the fluid delivery region comprises a foam manifold sealed between the inner layer and outer layer to form a space therebetween.

6. The system of claim 1, further comprising the fluid delivery member, wherein the fluid delivery member is coupled to the fluid delivery region adjacent the first retention member such fluid provided by the fluid delivery member fills the fluid delivery region in a bottom-up manner.

7. The system of claim 1, further comprising a fluid removal member, wherein the first retention member comprises a lumen in fluid communication with the fluid removal member and a plurality of holes in fluid communication with the lumen.

* * * * *